United States Patent
Guo et al.

(10) Patent No.: US 10,590,417 B2
(45) Date of Patent: Mar. 17, 2020

(54) RNA LIGAND-DISPLAYING EXOSOMES FOR SPECIFIC DELIVERY OF THERAPEUTICS TO CELL BY RNA NANOTECHNOLOGY

(71) Applicant: Ohio State Innovation Foundation, Columbus, OH (US)

(72) Inventors: Peixuan Guo, Dubin, OH (US); Fengmei Pi, Columbus, OH (US); Hui Li, San Francisco, CA (US); Shaoying Wang, Middlesex, NJ (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 16/152,911

(22) Filed: Oct. 5, 2018

(65) Prior Publication Data

US 2019/0024085 A1    Jan. 24, 2019

Related U.S. Application Data

(63) Continuation of application No. PCT/US2017/026165, filed on Apr. 5, 2017.

(60) Provisional application No. 62/319,104, filed on Apr. 6, 2016, provisional application No. 62/380,233, filed on Aug. 26, 2016.

(51) Int. Cl.
| | |
|---|---|
| *C12N 15/113* | (2010.01) |
| *A61K 9/127* | (2006.01) |
| *C12N 15/11* | (2006.01) |
| *A61K 9/51* | (2006.01) |
| *A61P 35/00* | (2006.01) |

(52) U.S. Cl.
CPC .......... *C12N 15/113* (2013.01); *A61K 9/1273* (2013.01); *A61K 9/51* (2013.01); *A61K 9/513* (2013.01); *A61P 35/00* (2018.01); *C12N 15/111* (2013.01); *C12N 2310/14* (2013.01); *C12N 2310/51* (2013.01); *C12N 2320/32* (2013.01)

(58) Field of Classification Search
CPC ................ A61K 9/2018; A61K 9/2054; A61K 31/7105; A61K 48/0025; A61K 48/0033; A61K 9/0019; A61K 9/0085; A61K 9/1271; A61K 9/1272; A61K 9/145; A61K 9/146
USPC ......... 424/450, 489, 491; 435/325, 375, 455
See application file for complete search history.

(56) References Cited

U.S. PATENT DOCUMENTS

| | | |
|---|---|---|
| 5,476,766 A | 12/1995 | Gold et al. |
| 5,503,978 A | 4/1996 | Schneider et al. |
| 5,543,293 A | 8/1996 | Gold et al. |
| 5,580,737 A | 12/1996 | Polisky et al. |
| 5,631,146 A | 5/1997 | Szostak et al. |
| 5,731,424 A | 3/1998 | Toothman et al. |
| 5,780,228 A | 7/1998 | Parma et al. |
| 5,786,462 A | 7/1998 | Schneider et al. |
| 5,792,613 A | 8/1998 | Schmide et al. |
| 5,795,721 A | 8/1998 | Rabin et al. |
| 5,846,713 A | 12/1998 | Pagratis et al. |
| 5,858,660 A | 1/1999 | Eaton et al. |
| 5,861,254 A | 1/1999 | Schneider et al. |
| 5,864,026 A | 1/1999 | Jensen et al. |
| 5,869,641 A | 2/1999 | Jayasena et al. |
| 5,958,691 A | 9/1999 | Pieken et al. |
| 6,001,988 A | 12/1999 | Parma et al. |
| 6,011,020 A | 1/2000 | Gold et al. |
| 6,013,443 A | 1/2000 | Heilig et al. |
| 6,020,130 A | 2/2000 | Gold et al. |
| 6,028,186 A | 2/2000 | Tasset et al. |
| 6,030,776 A | 2/2000 | Eaton et al. |
| 6,051,698 A | 4/2000 | Janjic et al. |
| 9,297,013 B2 * | 3/2016 | Guo ...................... C12N 15/111 |
| 2014/0010885 A1 | 1/2014 | De Los Rios et al. |
| 2015/0093433 A1 * | 4/2015 | Leonard ............... A61K 31/713 424/450 |

FOREIGN PATENT DOCUMENTS

| | | |
|---|---|---|
| WO | 0244321 A2 | 6/2002 |
| WO | 2005035760 A2 | 4/2005 |
| WO | 2012170372 A2 | 12/2012 |

OTHER PUBLICATIONS

International Search Report PCT/US2017/026165 dated Aug. 1, 2017.
Kedmi, et al., The systemic toxicity of positively charged lipid nanoparticles and the role of Toll-like receptor 4 in immune activation, Biomaterials, 31:6867-75, 2010.
Fire, et al., Potent and specific genetic interference by double-strandedRNAin Caenorhabditis elegans, Nature, 391:806-11, 1998.
Napoli, et al., Introduction of a Chimeric Chalcone Synthase Gene into Petunia Results in Reversible Co-Suppression of Homologous Genes in trans, Plant Cell 2:279-89, 1990.
Hannon, A conserved biological response to double-stranded RNA, known variously as RNA interference (RNAi) or post-transcriptional gene silencing, mediates resistance to both endogenous parasitic and exogenous pathogenic nucleic acids, and regulates the expression of protein-coding genes. RNAi has been cultivated as a means to manipulate gene expression experimentally and to probe gene function on a whole-genome scale., Nature, 418:244-51 2002.
Elbashir, et al., RNA interference is mediated by 21-and 22-nucleotide RNAs, Genes Dev., 15:188-200, 2001.

(Continued)

*Primary Examiner* — Janet L Epps-Smith
(74) *Attorney, Agent, or Firm* — Thomas|Horstemeyer, LLP

(57) ABSTRACT

Disclosed herein are compositions comprising extracellular vesicles, such as exosomes, displaying an RNA nanoparticle on its surface. The RNA nanoparticle can target the extracellular vesicle to a given cell via a targeting moiety. The extracellular vesicle can also comprise a functional moiety, which can be used in treatment or diagnostics.

18 Claims, 56 Drawing Sheets

Specification includes a Sequence Listing.

(56) References Cited

OTHER PUBLICATIONS

Bernstein, et al., Role for a bidentate ribonuclease in the initiation step of RNA interference, Nature, 409:363-6, 2001.
Hammond, et al., An RNA-directed nuclease mediates post-transcriptional gene silencing in Drosophila cells, Nature, 404:293-6, 2000.
Nykanen, et al., ATP Requirements and Small Interfering RNA Structure in the RNA Interference Pathway, Cell, 107:309-21, 2001.
Martinez, et al., Single-Stranded Antisense siRNAs Guide Target RNA Cleavage in RNAi, Cell, 110:563-74, 2002.
Elbashir, et al., Duplexes of 21±nucleotide RNAs mediate RNA interference in cultured mammalian cells, Nature, 411 :494 498, 2001.
Ui-Tei, et al., Sensitive assay of RNA interference in Drosophila and Chinese hamster cultured cells using ¢re£y luciferase gene as target, FEBS Lett 479:79-82, 2000.
Kim, et al., Genomics of microRNA, Trends Genet., 22:165-73, 2006.
Schwarz, et al., Asymmetry in the Assembly of the RNAi Enzyme Complex, Cell., 115: 199-208, 2003.
Braconi, et al., The Role of MicroRNAs in Human Liver Cancers, Seminars in oncology., 38:752-63, 2011.
Budhu, et al., Identification of Metastasis-Related MicroRNAs in Hepatocellular Carcinoma, Hepatology., 47:897-907, 2008.
Gramantieri, et al., Cyclin G1 Is a Target of miR-122a, a MicroRNA Frequently Down-regulatedin Human Hepatocellular Carcinoma, Cancer Res., 67:6092-9, 2007.
Jiang, et al., Association ofMicroRNA Expression in Hepatocellular Carcinomas with Hepatitis Infection, Cirrhosis, and Patient Survival, Clin Cancer Res., 14:419-27, 2008.
Pineau P, et al., miR-221 overexpression contributes to liver tumorigenesis, Proc Natl Acad Sci U S A., 2009.
Wang Y, et al., Profiling MicroRNA Expression in Hepatocellular Carcinoma Reveals MicroRNA-224 Up-regulation and Apoptosis Inhibitor-5 as a MicroRNA-224-specific Target, J Biol Chem., 283:13205-15, 2008.
Jasinski, et al., Large Scale Purification of RNA Nanoparticles by Preparative Ultracentrifugation. Methods in Molecular Biology 1297, 67-82, 2015.
Batrakova, et al., Using exosomes, naturally-equipped nanocarriers, for drug delivery. J. Control Release, 2015.
Meng F, et al., MicroRNA-21 Regulates Expression of the PTEN Tumor Suppressor Gene in Human Hepatocellular Cancer, Gastroenterology, 133:647-58, 2007.
Kulshreshtha, et al., Proinflammatory role of epithelial cell-derived exosomes in allergic airway inflammation, J. Allergy Clin. Immunol. 131, 1194-203, 1203, 2013.
Ji, et al., Identification of microRNA-181 by genome-wide screening as a critical player in EpCAM-positive hepatic cancer stem cells, Hepatology., 50:472-80, 2009.
Wang, et al., TGR3 mediated upregulation of hepatic miR-181b promotes hepatocarcinogenesis by targeting TIMP3, Oncogene, 29(12): 1787-97, 2010.
Hague, et al., Ultrastable synergistic tetravalent RNA nanoparticles for targeting to cancers, Nano Today 7, 245-257, 2012.
Murakami, et al., Comprehensive analysis of microRNA expression patterns in hepatocellular carcinoma and non-tumorous tissues, Oncogene, 25:2537-45, 2006.
Shu, et al., Fabrication of 14 Different RNA Nanoparticles for Specific Tumor Targeting without Accumulation in Normal Organs, RNA 19, 766-777, 2013.
Bai, et al., MicroRNA-122 Inhibits Tumorigenic Properties of Hepatocellular Carcinoma Cells and Sensitizes These Cells to Sorafenib, J Biol Chem., 284:32015-27, 2009.
Coulouam, et al, Loss of miR-122 expression in liver cancer correlates with suppression of the hepatic phenotype and gain of metastatic properties, Oncogene, 28:3526-36, 2009.

Fornari, et al., MiR-122/Cyclin G1 Interaction Modulates p53 Activity and Affects Doxorubicin Sensitivity of Human Hepatocarcinoma Cells, Cancer Res., 69:5761-7, 2009.
Kutay, et al. Downregulation of miR-122 in the Rodent and Human Hepatocellular Carcinomas, J Cell Biochem., 99:671-8, 2006.
Chen, et al. Molecular therapy: the journal of the American Society of Gene Therapy, 19: 1521-8, 2011.
Shu, et al., Thermodynamically stable RNA three-way junctions for constructing multifuntional nanoparticles for delivery of therapeutics, Nature Nanotechnology 6, 658-667, 2011.
Zhang, et al., Crystal Structure of 3WJ Core Revealing Divalent Ion-promoted Thermostability and Assembly of the Phi29 Hexameric Motor pRNA, RNA 19, 1226-1237, 2013.
Lamichhane, et al., Exogenous DNA Loading into Extracellular Vesicles via Electroporation is Size-Dependent and Enables Limited Gene Delivery, Mol. Pharm. 12, 3650-3657, 2015.
Thery, et al., Isolation and characterization of exosomes from cell culture supernatants and biological fluids, Curr. Protoc. Cell Biol Chapter 3, Unit 3.22, 2006.
Bunge, et al., Lipid membranes carrying lipophilic cholesterol-based oligonucleotides—characterization and application on layer-by-layer coated particles, J Phys Chem. B 113, 16425-16434, 2009.
Pfeiffer, et al., Bivalent cholesterol-based coupling of oligocucletides to lipid membrane assemblies, J Am. Chem. Soc 126, 10224-10225, 2004.
Marcus, et al., FedExosomes: Engineering Therapeutic Biological Nanoparticles that Truly Deliver. Pharmaceuticals, (Basel) 6, 659-680, 2013.
van Dongen, et al., Extracellular Vesicles Exploit Viral Entry Routes for Cargo Delivery, Microbiol. Mol. Biol. Rev. 80, 369-386, 2016.
Parker, et al., Folate receptor expression in carcinomas and normal tissues determined by a quantitative radioligand binding assay, Anal. Biochem. 338, 284-293, 2005.
Rockey, et al., Rational truncation of an RNA aptamer to prostate-specific membrane antigen using computational structural modeling, Nucleic Acid Ther. 21, 299-314, 2011.
Paduano, et al., Silencing of survivin gene by small interfering RNAs produces supra-additive growth suppression in combination with 17-allylamino-17-demethoxygeldanamycin in human prostate cancer cells, Molecular Cancer Therapeutics 5, 179-186, 2006.
Cui, et al., Regression of gastric cancer by systemic injection of RNA nanoparticles carrying both ligand and siRNA, Scientific reports 5, 10726, 2015.
Lee, et al., RNA nanoparticles as a vector for targeted siRNA delivery into glioblastoma mouse model, Oncotarget 6, 14766-14776, 2015.
varez-Erviti, et al., Delivery of siRNA to the mouse brain by systemic injection of targeted exosomes, Nat Biotechnol. 29, 341-345, 2011.
Ohno, et al., Systemically injected exosomes targeted to EGFR deliver antitumor microRNA to breast cancer cells, Mol Ther. 21, 185-191, 2013.
Tian, Y. et al., A doxorubicin delivery platform using engineered natural membrane vesicle exosomes for targeted tumor therapy, Biomaterials 35, 2383-2390, 2014.
Binzel, et al., Entropy-driven one-step formation of Phi29 pRNA 3WJ from three RNA fragments, Biochemistry 53, 2221-2231, 2014.
Li, et al., In vitro and preclinical targeted alpha therapy of human prostate cancer with Bi-213 labeled J591 antibody against the prostate specific membrane antigen, Prostate Cancer Prostatic. Dis. 5, 36-46, 2002.
Pettaway, et al., Selection of highly metastatic variants of different human prostatic carcinomas using orthotopic implantation in nude mice, Clin. Cancer Res 2, 1627-1636, 1996.
Pecot, et al., RNA interference in the clinic: challenges and future directions, Nat Rev. Cancer 11, 59-67, 2011.
Grodzinski, P., Torchilin, V. & (Editors) Advanced Drug Delivery Reviews: Cancer Nanotechnology, Elsevier, 2014.
Kesharwani, et al., a review of nanocarriers for the delivery of small interfering RNA, Biomaterials 33, 7138-7150, 2012.
El-Andaloussi, et al., Extracellular vesicles: biology and emerging therapeutic opportunities, Nat Rev. Drug Discov. 12, 347-357, 2013.

(56) References Cited

OTHER PUBLICATIONS

Valadi, et al., Exosome-mediated transfer of mRNAs and microRNAs is a novel mechanism of genetic exchange between cells, Nat Cell Biol 9, 654-659, 2007.
El-Andaloussi, etal., Exosomes for targeted siRNA delivery across biological barriers, Adv. Drug Deliv. Rev. 65, 391-397, 2013.
van Dommelen, et al., Microvesicles and exosomes: opportunities for cell-derived membrane vesicles in drug delivery, J Control Release 161, 635-644, 2012.
Wiklander, et al., Extracellular vesicle in vivo biodistribution is determined by cell source, route of administration and targeting, J Extracell. Vesicles. 4, 26316, 2015.
Guo, The emerging field of RNA nanotechnology, Nature Nanotechnology 5, 833-842, 2010.
Shu, et al., Programmable folding of fusion RNA complex driven by the 3WJ motif of phi29 motor pRNA, Nucleic Acids Res. 42, e10, 2013.
Shu, et al., Systemic delivery of anti-miRNA for suppression of triple negative breast cancer utilizing RNA nanotechnology, ACS Nano 9, 9731-9740, 2015.
Rychahou, et al., Delivery of RNA nanoparticles into colorectal cancer metastases following systemic administration, ACS Nano 9, 1108-1116, 2015.
International Search Report issued for PCT/US2017/026165, dated Aug. 1, 2017.

\* cited by examiner

EM images
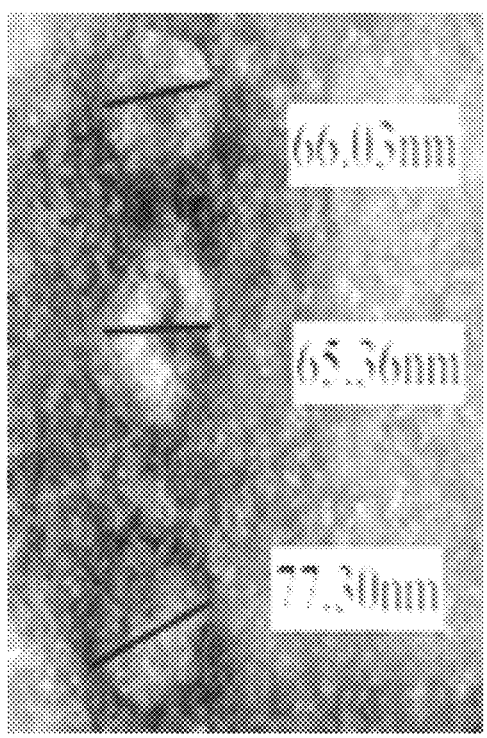
Size (DLS)
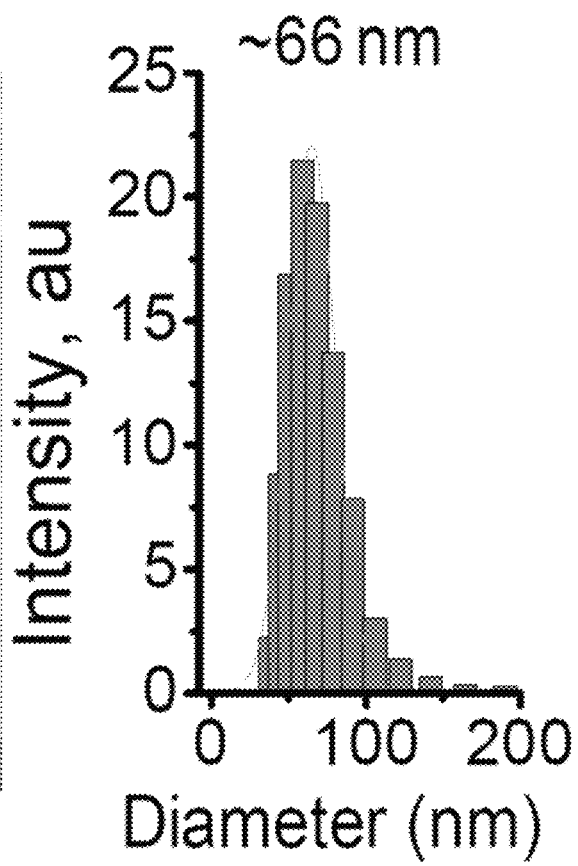
FIG. 3A
FIG. 3B

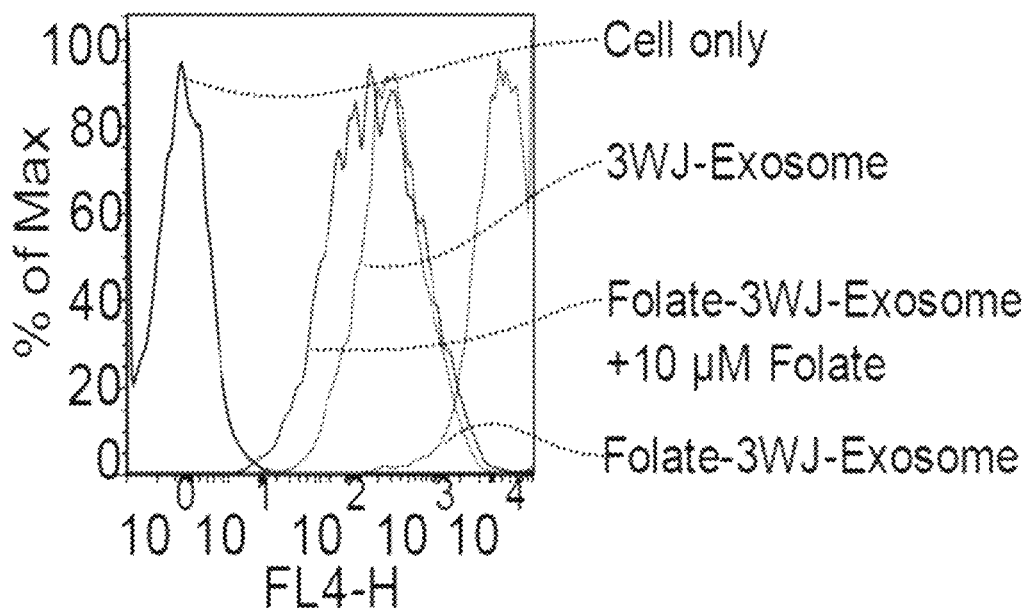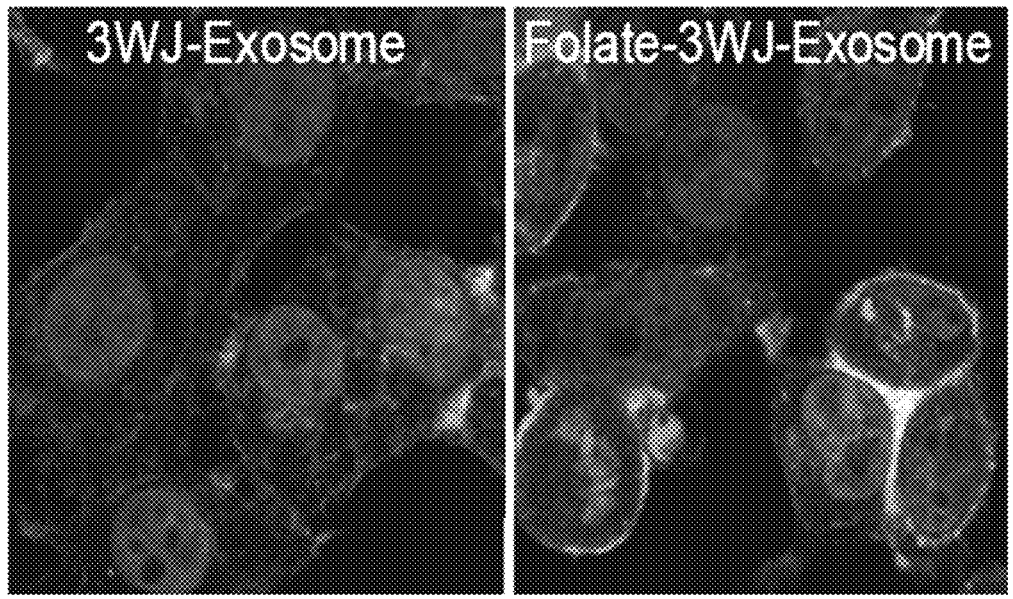
FIG. 5B

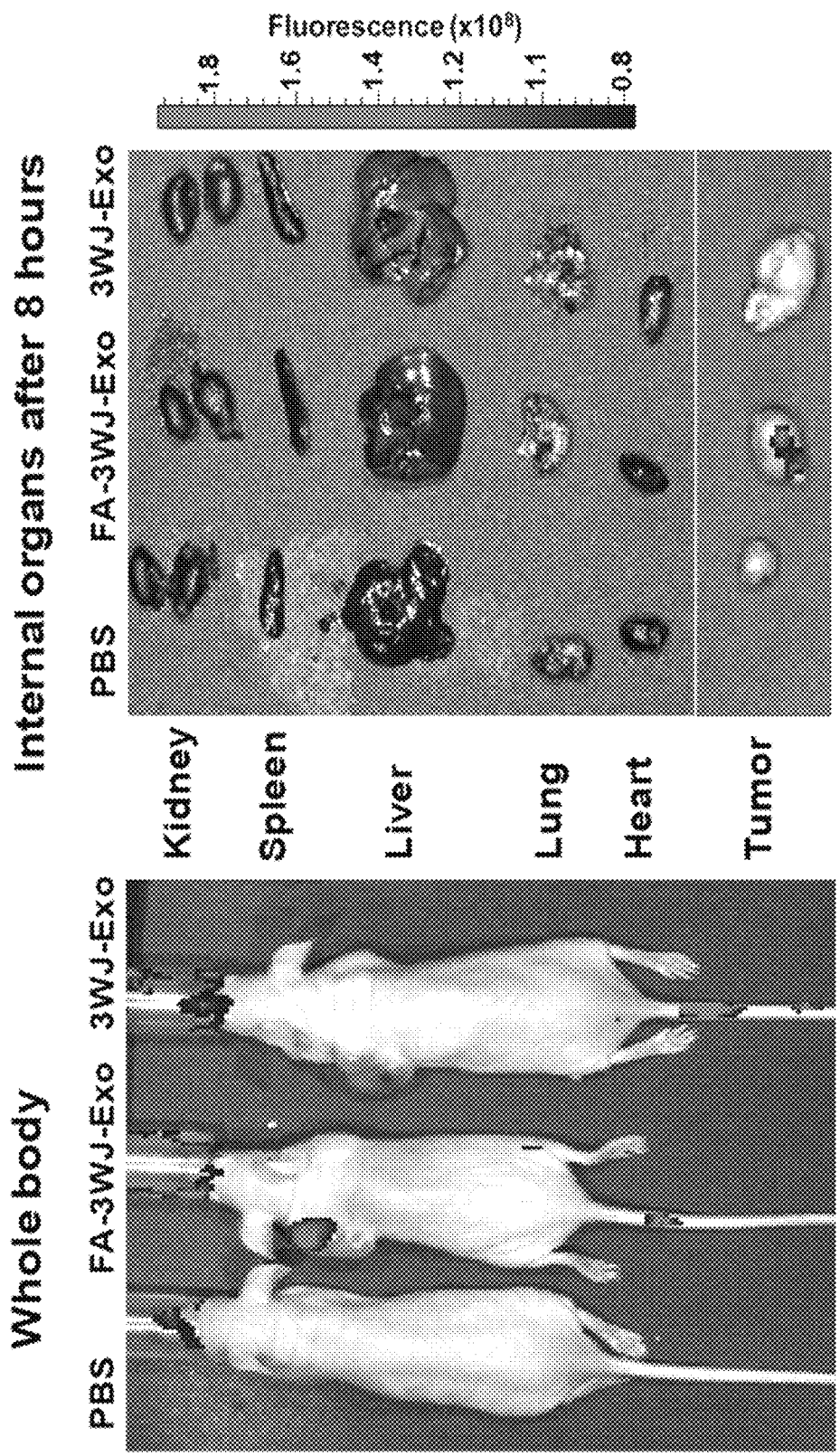

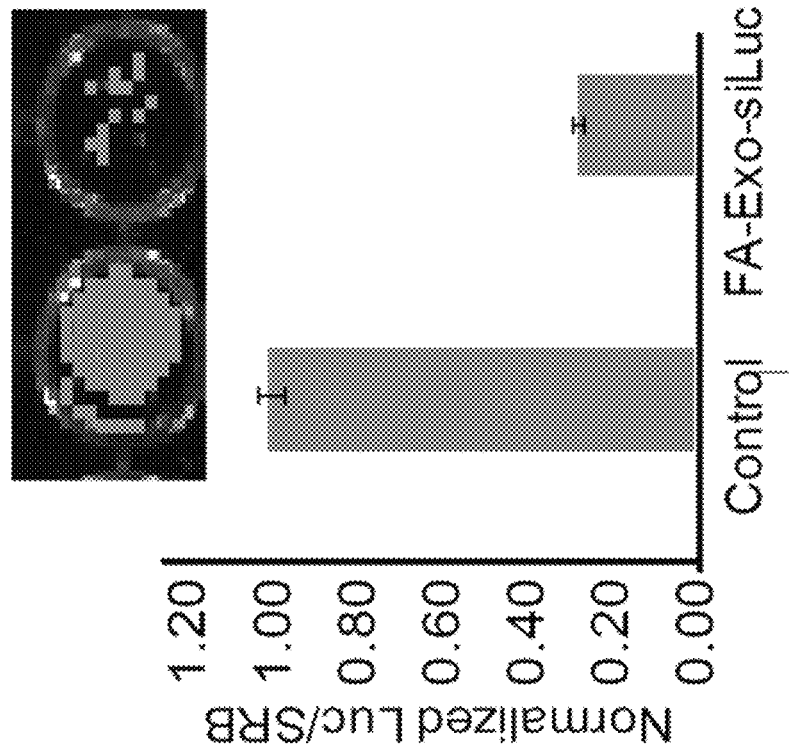
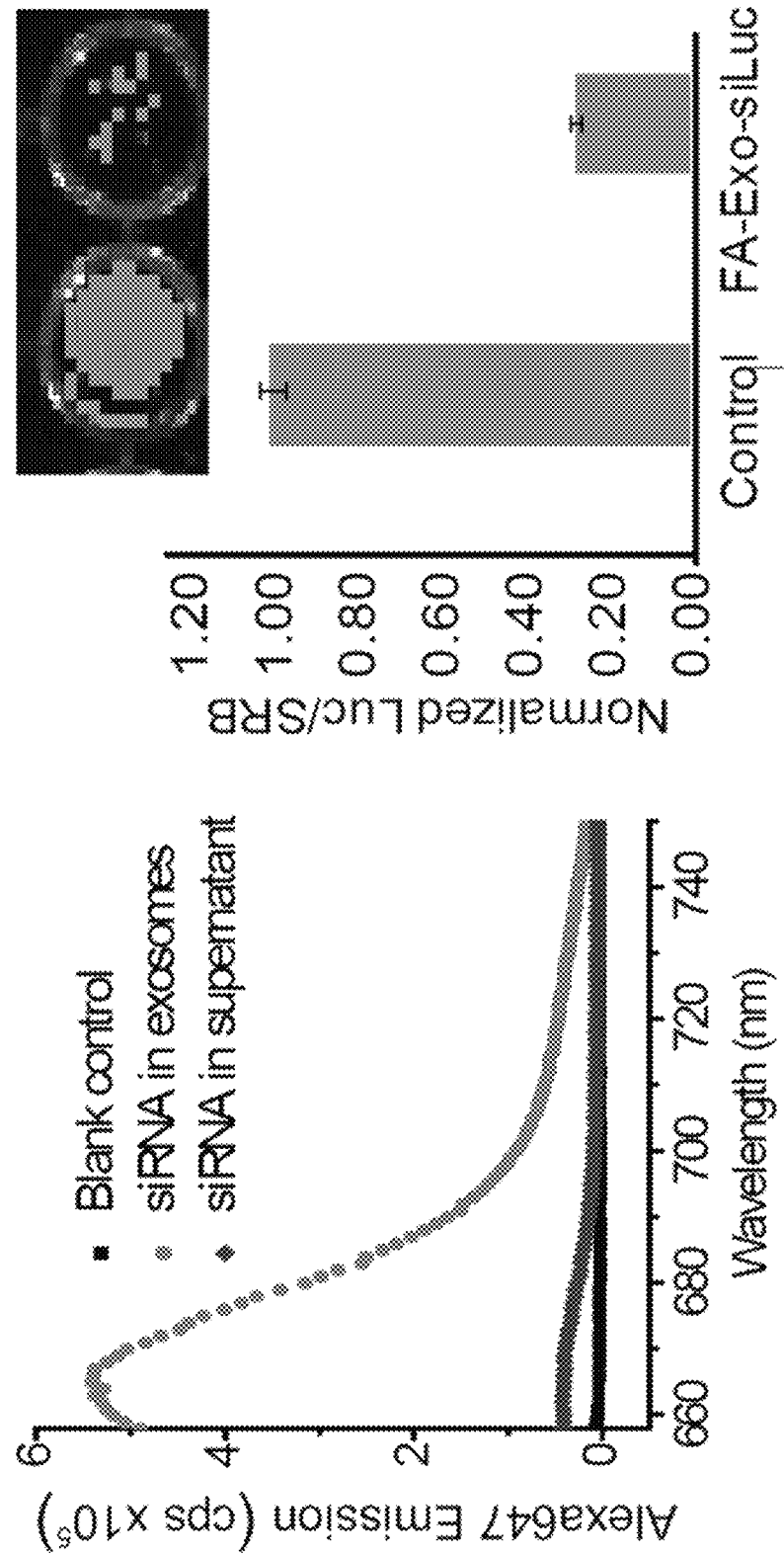
FIG. 7A
FIG. 7B

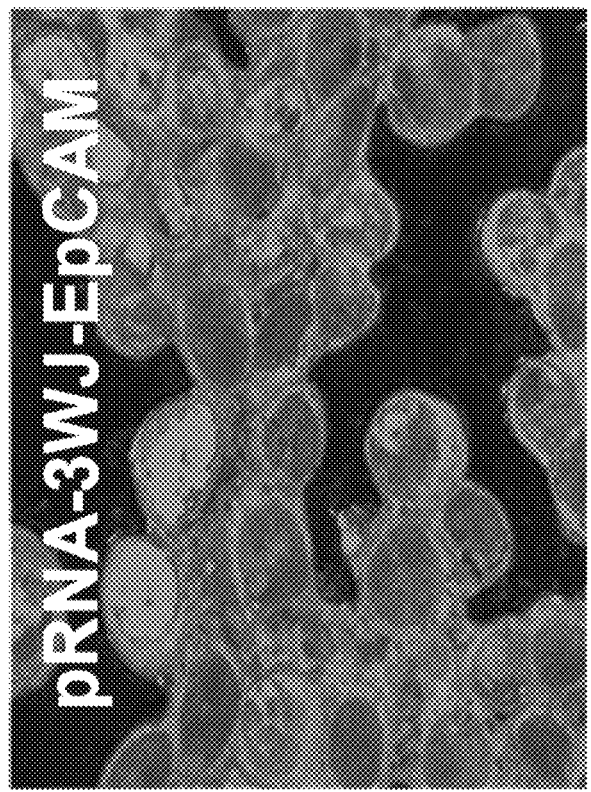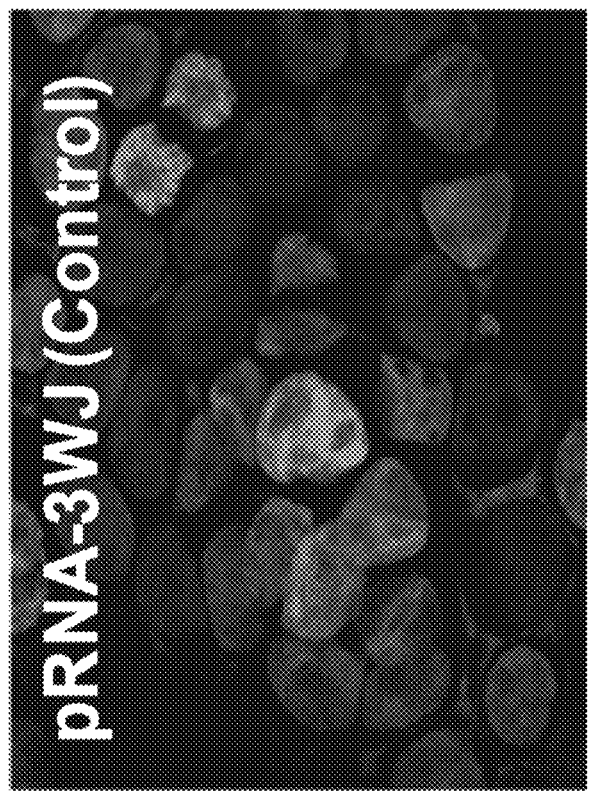
FIG. 10

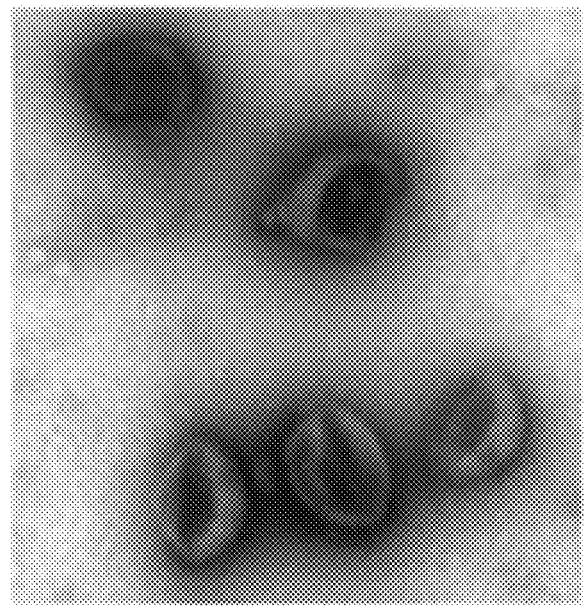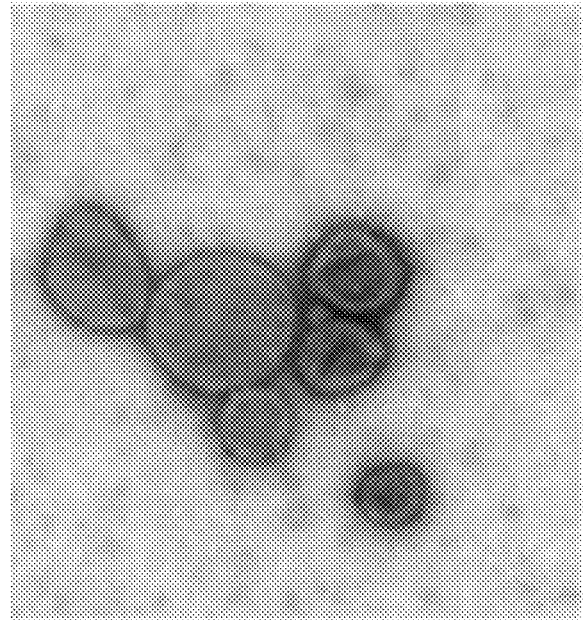
FIG. 12C

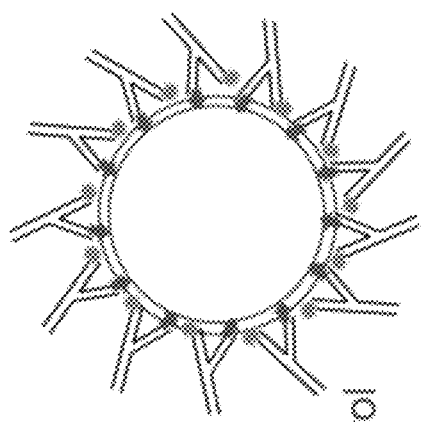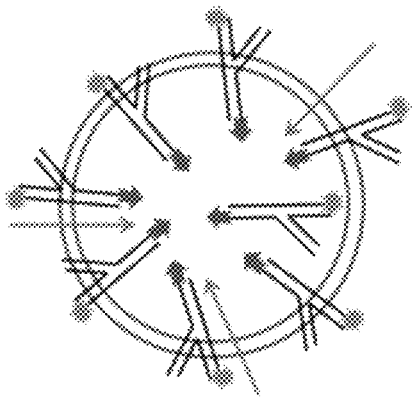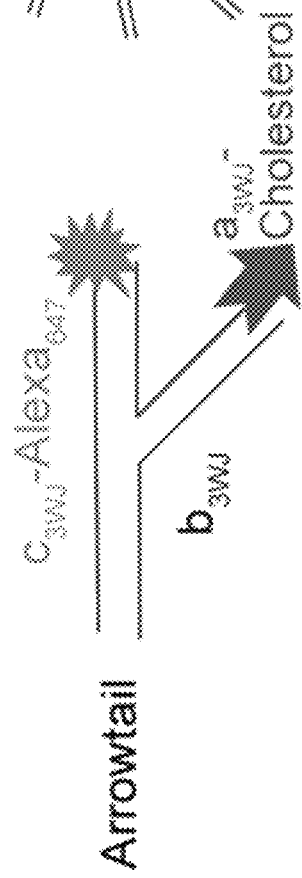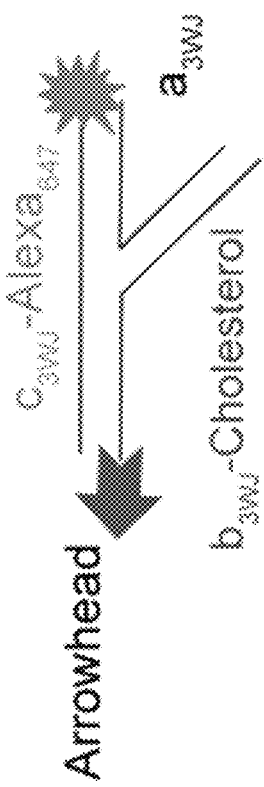
FIG. 13A
FIG. 13B

1. Arrowtail 3WJ/EV + FBS, 0 °C, 5 min
2. Arrowtail 3WJ/EV + FBS, 37 °C, 2 hr
3. Arrowhead 3WJ/EV + FBS, 0 °C, 5 min
4. Arrowhead 3WJ/EV + FBS, 37 °C, 2 hr EM of EVs
Cushion UC
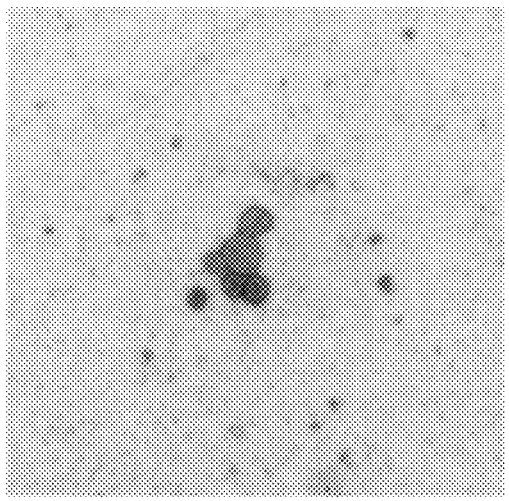
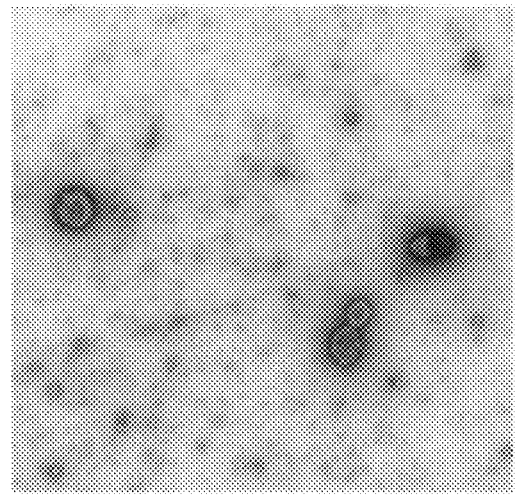
No-Cushion UC
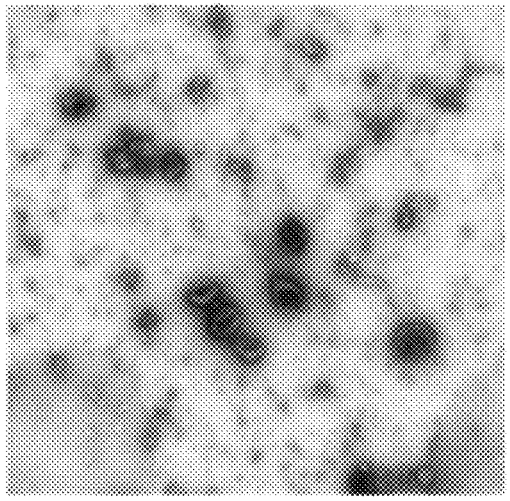
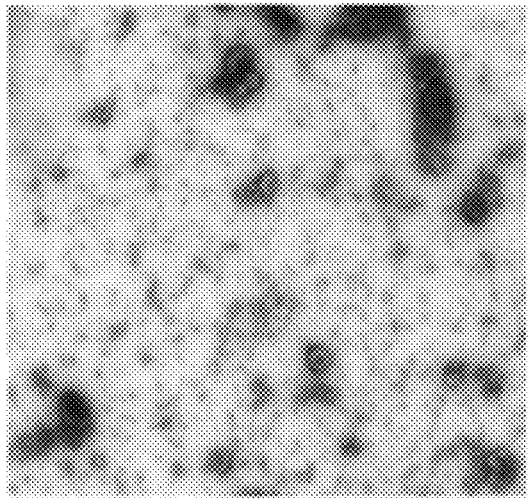
FIG. 18C

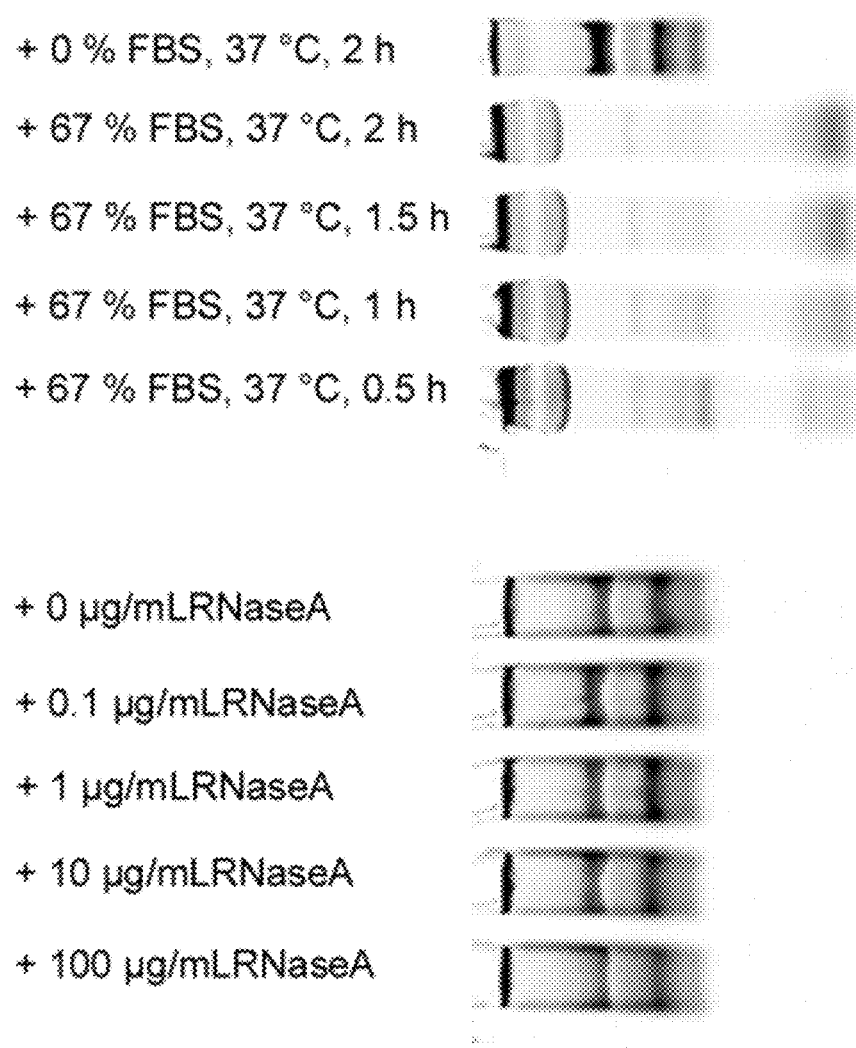

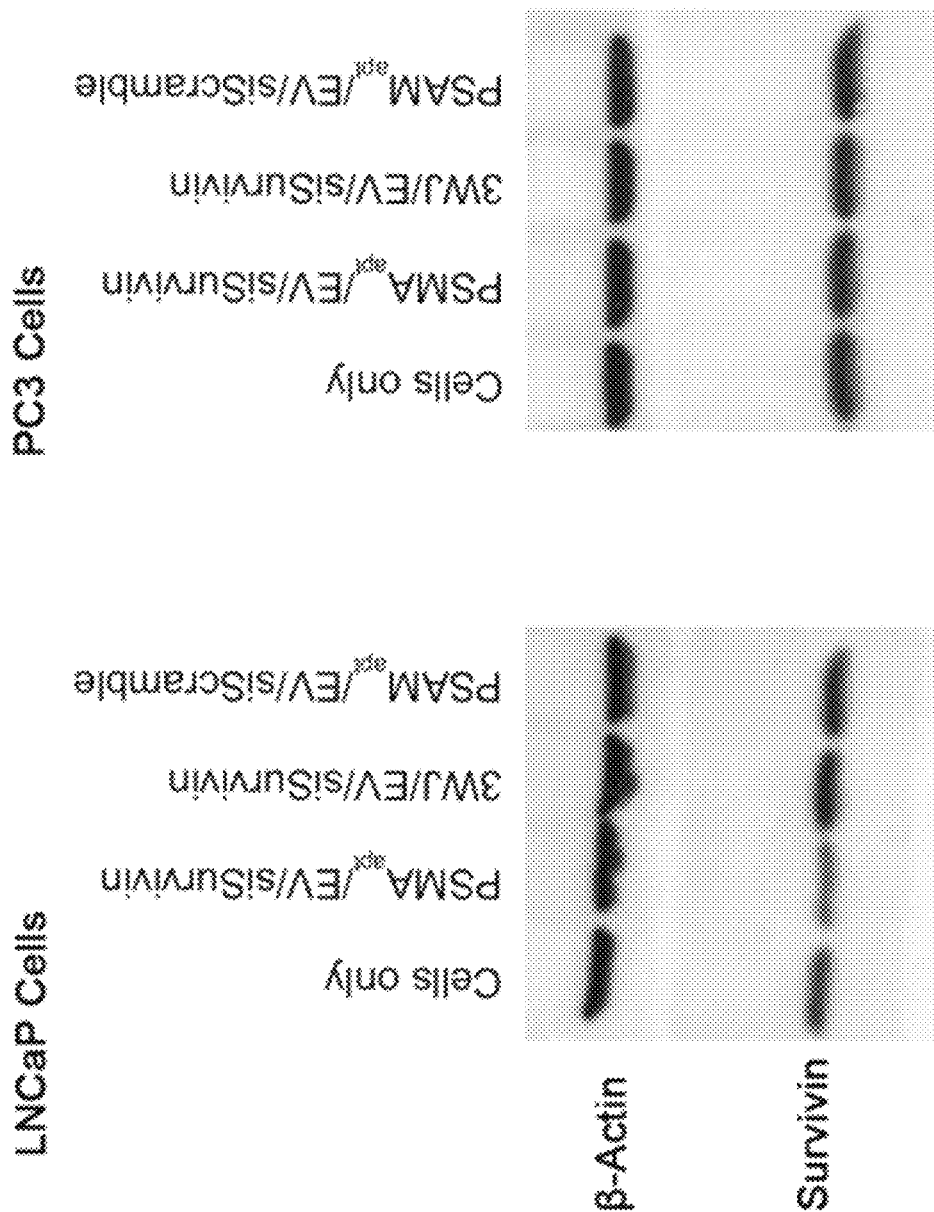

RNA LIGAND-DISPLAYING EXOSOMES FOR SPECIFIC DELIVERY OF THERAPEUTICS TO CELL BY RNA NANOTECHNOLOGY

CROSS-REFERENCE TO RELATED APPLICATIONS

This application is a continuation of copending International Application Serial No. PCT/US2017/026165, filed Apr. 5, 2017, which claims benefit of U.S. Provisional Application No. 62/319,104, filed Apr. 6, 2016, and Application Ser. No. 62/380,233, filed Aug. 26, 2016, which are hereby incorporated herein by reference in their entirety.

STATEMENT REGARDING FEDERALLY SPONSORED RESEARCH OR DEVELOPMENT

This invention was made with government support under grant numbers P30CA177558; R01EB019036; R01EB012135; R01EB003730; R01CA186100; R01CA195573; R35CA197706; U01CA151648; and UH3TR000875 awarded by the National Institutes of Health. The government has certain rights in the invention.

BACKGROUND

Specific cancer cell targeted RNAi drug delivery is a very promising strategy for many disease treatments including cancer. Exosomes, naturally derived nano vesicles from the endosome membrane of cells, showed very encouraging ability to deliver siRNA into cells in vitro. But to conquer the physiological barriers and achieve therapeutic effect in vivo, exosomes with specific cancer cell targeting property are demanded. Disclosed herein are methods and compositions for displaying ligands onto exosome surface post-biogenesis. RNA nanostructures can be utilized as a tool to display the RNA or chemical based ligand onto exosome surface, thus increase their cell targeting specificity and thus can be used for specific delivery of therapeutic reagent, such as RNAi therapeutics, to the targeted cells.

RNA nanostructures derived from packaging RNA of phi29 DNA packaging motor have shown great promise for drug delivery. The 3WJ domain of pRNA is highly thermodynamically stable, can be formed from 3 pieces of short RNA oligonucleotides with high affinity. Furthermore, when using the 3WJ as a core for building RNA nanoparticles, it can drive the global folding of the RNA nanoparticle and ensure the correct folding of fused aptamer sequences to remain functional. Cholesterol was applied to modified pRNA-3WJ for displaying ligand onto exosome surface. The results showed that both chemical ligand and RNA aptamer can be displayed on exosome via cholesterol modified pRNA 3WJ. Ligand displaying exosomes have enhanced specific tumor binding efficiency in vitro. In the animal experiment, ligand displaying exosomes showed specific accumulation in tumor after systemic injection. Exosome was further loaded with siRNA, ligand displaying exosomes can enhance the siRNA delivery efficiency to target cancer cells in vitro and in vivo.

RNAi therapeutics is very promising for treating various diseases including cancer, since it has the ability to modify disease gene expression. However, despite years of extensive research, an efficient and biocompatible RNAi delivery system is still lacking. Though liposomes show great success for siRNA delivery in vitro, but when systemically administering in vivo, the problems persist of liver accumulation and freeze-thaw cycles causing instability in the final product.

Exosomes, which are nano-scaled vesicles originated from cell endosome membrane, have been studied extensively as RNAi drug delivery system recently. But to achieve specific cancer cell targeting is still challenging. Current technologies are exploring expressing cancer cell specific ligand on exosome generating cells to increase the exosome specificity, such as overexpression peptide ligands on the exosome membrane as fusion protein on HEK293T cells. But one problem for using fusion peptides for targeted exosome delivery is that the displayed peptide can be degraded during exosome biogenesis.

What is needed in the art is RNA ligand-displaying exosomes for specific delivery of therapeutics to cells by RNA technology.

SUMMARY

Delivery of therapeutics to diseased cells without harming healthy cells is a major challenge in medicine. Exosomes (20-100 nm specialized membranous vesicles of endocytotic origin) have tremendous potentials to deliver RNA interference (RNAi) agents, genome editing and repair modules, and chemotherapeutics to diseased cells due to their innate ability to (1) fuse with recipient cell with high efficiency and (2) deliver the packaged therapeutic cargoes to the cytosol with full expression of the DNA and RNA without getting trapped in endosomes. However, their lack of specific cell targeting capabilities and non-specific accumulation in liver and other healthy organs is a major problem that has diminished their therapeutic potency. RNA nanotechnology can be used to generate RNA nanoparticles capable of targeting cancer cells specifically with little or no accumulation in healthy vital organs. However, after internalization into cancer cells via receptor-mediated endocytosis, RNA nanoparticles can get trapped in the endosomes, and their endosome escape efficiency is still low, thus the therapeutic cargoes have limited efficacy. The fields of "Exosomes" and "RNA nanotechnology" are combined herein to display specific ligands on exosome surface. The engineered exosomes are able to target diseased cells specifically and enter the cells efficiently to deliver their cargo into the cytosol without getting trapped in endosomes.

Disclosed herein is a composition comprising an exosome, wherein the exosome displays an RNA nanoparticle on its surface, e.g., anchored within the exosome membrane. The nanoparticle can be a nucleic-acid based nanoparticle, such as RNA. In some embodiments, the nanoparticle is assembled from three or more ribonucleic acid strands duplexed together to form a secondary structure with three or more projecting stem loops. In some embodiments, the nanoparticle comprises a membrane-anchoring moiety at one of the three or more projecting stem loops. In some embodiments, the nanoparticle comprises one or more functional moieties at the remaining stem loops.

In some embodiments, at least one of the three or more ribonucleic acid strands comprise a pRNA-3WJ core. For example, the RNA nanoparticle can be assembled from three ribonucleic acid strands comprising the nucleic acid sequences SEQ ID NO:1, SEQ ID NO:2, and SEQ ID NO:3.

In some embodiments, the membrane-anchoring moiety comprises a cholesterol or modified cholesterol. Cholesterol is hydrophobic, and when conjugated to oligonucleotides, can facilitate uptake into cells. In some embodiments, the cholesterol further comprises a triethylene glycol (TEG)

spacer, which can further increases cellular uptake. Other lipophilic moieties capable of anchoring an oligonucleotide in the lipid bi-layer membrane of an exosome are can also be used.

In some embodiments, one or more of the functional moieties comprises a targeting moiety. The targeting moiety can, for example, direct the exosome to a cell of interest. In some embodiments, the targeting moiety is selected from an RNA aptamer, modified RNA aptamer, DNA aptamer, modified DNA aptamer, and chemical ligand.

In some embodiments, the functional moieties comprises a therapeutic moiety or a diagnostic moiety. For example, the therapeutic moiety or a diagnostic moiety can comprise an RNA aptamer, a ribozyme, siRNA, protein-binding RNA aptamer, or small molecule.

In some embodiments, the three or more projecting stem loops of the nanoparticle are configured so that a first stem loop is projecting in a first direction, and the second and third stem loops are projecting substantially away from the first direction Also disclosed is a method of targeting an exosome to a cell that involves contacting the cell with a composition comprising an exosome displaying an RNA nanoparticle on its surface, wherein the nanoparticle comprises at least one targeting moiety, wherein the targeting moiety directs the exosome to the cell of interest. For example, in some embodiments, the cell is a cell in a subject, such as a cancer cell. In some embodiments, the RNA nanoparticle further comprises a functional moiety, such as a therapeutic or diagnostic moiety.

Further disclosed is a method of treating disease in a subject, comprising administering to the subject an exosome displaying an RNA nanoparticle on its surface, wherein the nanoparticle comprises at least one targeting moiety, and further wherein the exosome comprises a functional moiety, wherein the functional moiety is capable of treating the disease in the subject. For example, in some embodiments, the disease is an infection. In some embodiments, the disease is a cancer.

Also disclosed is a method of imaging a cell that involves contacting the cell with a composition comprising an exosome displaying an RNA nanoparticle on its surface, wherein the nanoparticle comprises at least one targeting moiety at least one diagnostic moiety. For example, in some embodiments, the cell is a cell in a subject.

DESCRIPTION OF DRAWINGS

FIGS. 3A to 3D show characterization of exosomes from HEK293 cells. FIG. 3A contains EM images showing that exosomes have a characteristic cup-shaped morphology. FIG. 3B contains DLS (Dynamic Light Scattering) assay showing the size of extracted exosomes (66±15 nm). FIG. 3C shows apparent Zeta potential (−18±15 mV) of exosomes. FIG. 3D contains Western blot showing enrichment of exosome marker TSG101.

FIG. 5B shows exosomes harboring folate as a targeting ligand can enter HT29 colorectal cancer cells by Folate receptor-mediated endocytosis, as well as by fusing with the plasma membrane via tetraspanin and fusion protein domains. The confocal images are overlap of Nucleus; Cytoplasm; and Exosomes with surface anchored RNA.

FIGS. 6A and 6B are whole body (FIG. 6A) and internal organ (FIG. 6B) images showing that upon systemic injection, FA-3WJ-Exosomes specifically targeted folate receptor (+) KB cell subcutaneous xenografts and were not detected in any vital organs after 8 hrs.

FIG. 7A is a fluorescence assay showing >95% efficiency for loading RNAi into exosomes. FIG. 7B is a dual luciferase assay showing specific knockdown (>80%) of luciferase after incubation of Folate-3WJ-exosomes with folate receptor(+) KB cells expressing luciferase.

FIG. 10 contains confocal images showing strong binding and entry of Alexa647-pRNA-3WJ-EpCAM-aptamer into HT29 colorectal cancer cells. The aptamer was selected from a novel 2'-F 3WJ library based on RNA nanotechnology.

FIGS. 12A to 12I show RNA nanotechnology for decorating native EVs. FIG. 12A is an AFM image of extended 3WJ of the motor pRNA of bacteriophage phi29. FIG. 12B is an illustration of the location for cholesterol labeling of the arrow-head or arrow-tail of 3WJ. FIG. 12C contains a negative-stained EM image of EVs from HEK293T cells purified with differential ultracentrifugation method and cushion modified ultracentrifugation method. FIGS. 12D to 12G show NTA for size analysis and DLS for Zeta potential measurements. FIG. 12H shows 2D structure (left panel) and native PAGE for testing 3WJ assembly from three component strands, as indicated. FIG. 12I shows EVs loading and RNA aptamer display. $a_{3WJ}$ (SEQ ID NO:1); $a_{3WJ}$(SEQ ID NO:1)-Cholesterol; $b_{3WJ}$(SEQ ID NO:2); $b_{3WJ}$(SEQ ID NO:2)-Cholesterol; $b_{3WJ}$(SEQ ID NO:2)-Alexa647; $c_{3WJ}$ (SEQ ID NO:3); $c_{3WJ}$-PSMA$_{apt}$ (SEQ ID NO:7).

FIGS. 13A to 13I show comparison of the role between arrow-head and arrow-tail 3WJ. FIGS. 13A and 13B contain illustrations showing the difference between arrow-head and arrow-tail display. FIG. 13C shows Syner gel to test arrow-head and arrow-tail Alexa647-3WJ/EV degradation by RNase in FBS. FIG. 13D shows results of a gel imaged at Alexa647 channel and the bands quantified by Image J. FIGS. 13E to 13I show results of assay to compare cell binding of folate-3WJ arrow-tail (FIGS. 13E to 13G) and arrow-head (FIGS. 13H to 13I) on folate receptor positive and negative cells.

FIG. 14A contains flow cytometry (left) and confocal images (right) showing the binding of PSMA RNA aptamer-displaying EVs to PSMA-receptor positive and negative cells. Nucleus, cytoskeleton, and RNA are labeled in confocal images. FIG. 14B shows RT-PCR assay for PSMA aptamer-mediated delivery of survivin siRNA by EVs to PSMA(+) prostate cancer cells. Statistics: n=3; experiment was run in three biological replicates and three technical repeats with a two-sided t-test; p=0.0061, 0.0001 comparing PSMAapt/EV/siSurvivin to PSMAapt/EV/siScramble and 3WJ/EV/siSurvivin, respectively. FIG. 14C contains an MTT assay showing reduced cellular proliferation. n=3, p=0.003, 0.031 comparing PSMAapt/EV/siSurvivin to PSMAapt/EV/siScramble and 3WJ/EV/siSurvivin respectively. *p<0.05, **p<0.01.

FIG. 15A shows intravenous treatment of nude mice bearing LNCaP-LN3 subcutaneous xenografts with PSMAapt/EV/siSurvivin or PSMAapt/EV/siScramble (both with 0.6 mg/kg, siRNA/mice body weight), and PBS, injected twice per week for three weeks. n=10 biological replicates, 2 independent experiments, and statistics were calculated using a two-sided t-test expressed as averages and with standard deviation. p=0.347, 0.6-2, 1.5e-6, 8.2e-8, 2.1e-7, 1.0e-7, 1.9e-7, 1.8e-6 for days 15, 18, 22, 25, 29, 32, 36, and 39 respectively for PSMAapt/EV/siSurvivin compared to control. FIG. 15B contains results of RT-PCR showing the trend of knockdown survivin mRNA expression in prostate tumors after EV treatment. FIG. 15C shows body weight of mice during the time course of EVs treatment.

FIG. 16A shows EGFR aptamer displaying EVs showed enhanced targeting effect to breast tumor in orthotopic xenograft mice models. FIG. 16B shows intravenous treatment of nude mice bearing breast cancer orthotopic xenografts with EGFRapt/EV/siSurvivin and controls (n=5). After 6 weeks, EGFRapt/EV/siSurvivin treated group had significantly smaller tumor size than other controls. p=0.008 comparing EGFRapt/EV/siSurvivin to EGFRapt/EV/siScramble. FIG. 16C contains analysis of the protein expression in tumor extracts showing that EGFRapt/EV/siSurvivin treatment significantly reduced the expression of Survivin. p=0.0004 comparing EGFRapt/EV/siSurvivin to EGFRapt/EV/siScramble. FIG. 16D contains quantitative real-time PCR analysis of extracted RNA from tumors showing the reduction of Survivin mRNA in the EGFRapt/EV/siSurvivin treated mice compared to controls. p=0.024 comparing EGFRapt/EV/siSurvivin to EGFRapt/EV/siScramble. Error bars indicate s.e.m. *p<0.05, p<0.01, *p<0.001.

FIG. 17A contains organ images showing specific tumor targeting 8 hr after systemic injection of folate displaying EVs to mice with subcutaneous KB cell xenografts. n=2, two independent experiments. FIG. 17B shows intravenous treatment of nude mice bearing PDX-CRC xenografts with FA/EV/siSurvivin and controls (n=4). After 6 weeks, FA/EV/siSurvivin treated group had significantly smaller tumor size, p=0.0098 and 0.0387 comparing FA/EV/siSurvivin to FA/EV/siScramble at week 4 and week 5 respectively. FIG. 17C shows lower tumor weight after treatment compared to controls. p=0.0024 comparing FA/EV/siSurvivin to FA/EV/siScramble. Error bars indicate s.e.m. *p<0.05, **p<0.01.

FIGS. 18A to 18E show physical properties of PSMAapt/EV/siSurvivin nanoparticles. FIG. 18A shows a Western blot assay to test the presence of EV marker TSG101 from the purified HEK293T EVs. EVs were detected as negative for integrin α5, integrin α6, integrin β1, integrin β4, integrin β5 and glypican1 expression. HEK293T cell lysate and LNCaP cell lysate were used as controls. Equal amount of cell lysate was used as negative control. FIG. 18B shows primary sequence and secondary structure of 3WJ harboring surviving siRNA sequences. FIG. 18C shows EM image of EVs purified from HEK293T cell culture medium, with either differential ultracentrifugation method or OptiPrep cushion modified ultracentrifugation method. FIG. 18D shows loading efficiency of siRNA into EVs. Control samples without transfection reagent Exo-Fect or EVs were tested. In the "No EVs" control sample, the Alexa647 labeled 3WJ-Survivin RNA nanoparticles were treated with ExoFect, and pelleted down after adding ExoTC. Around 15% of Alexa647-3WJ-Surivin RNA were detected in the pellets, which might be caused by forming complex with ExoTC. FIG. 18E shows results of NTA quantifying the particle amount and testing the particle size distribution of 3WJ-survivin siRNA loaded EVs or negative controls without EVs, or PBS only. $a_{3WJ}$-survivin sense (SEQ ID NO:5); Survivin anti-sense (SEQ ID NO:6); $b_{3WJ}$(SEQ ID NO:2); $c_{3WJ}$(SEQ ID NO:3)-Alexa647.

FIGS. 19A and 19B show the condition to digest 3WJ-cholesterol 2'F RNA nanoparticles. FIG. 19A shows 2'F Alexa647-3WJ-cholesterol RNA nanoparticles cannot be digested by RNaseA at tested concentrations. FIG. 19B shows that it can be digested in 67% FBS. The native polyacrylamide gels were imaged with Typhoon (GE healthcare) using Cy5 channel. The condition of incubating with 67% FBS at 37° C. for 2 hours was used for testing whether EVs can protect arrow head or arrow tail cholesterol displaying 3WJ 2'F RNA nanoparticles.

FIGS. 20A to 20D show specific siRNA delivery to cells in vitro using PSMA aptamer-displaying EVs. Western blot assay for PSMA aptamer-mediated delivery of survivin siRNA by EV to PSMA(+) prostate cancer LNCaP cells (FIG. 20A) and PSMA(−) prostate cancer PC3 cells (FIG. 20B). FIGS. 20C and 20D show quantified band intensity of 3 independent experiments with Image J software, and normalized the relative survivin protein expression level to β-actin.

FIG. 21A shows EGFRapt/3WJ/Cholesterol RNA nanoparticle for breast cancer study. FIG. 21B shows FA/3WJ/Cholesterol RNA nanoparticle for colorectal cancer study. $a_{3WJ}$(SEQ ID NO:1)-Cholesterol; $b_{3WJ}$(SEQ ID NO:2); $b_{3WJ}$-EGFR$_{apt}$ (SEQ ID NO:10); $c_{3WJ}$(SEQ ID NO:3)-Alexa647; Folate-$c_{3WJ}$(SEQ ID NO:3)-Alexa647.

DETAILED DESCRIPTION

Figure 1:
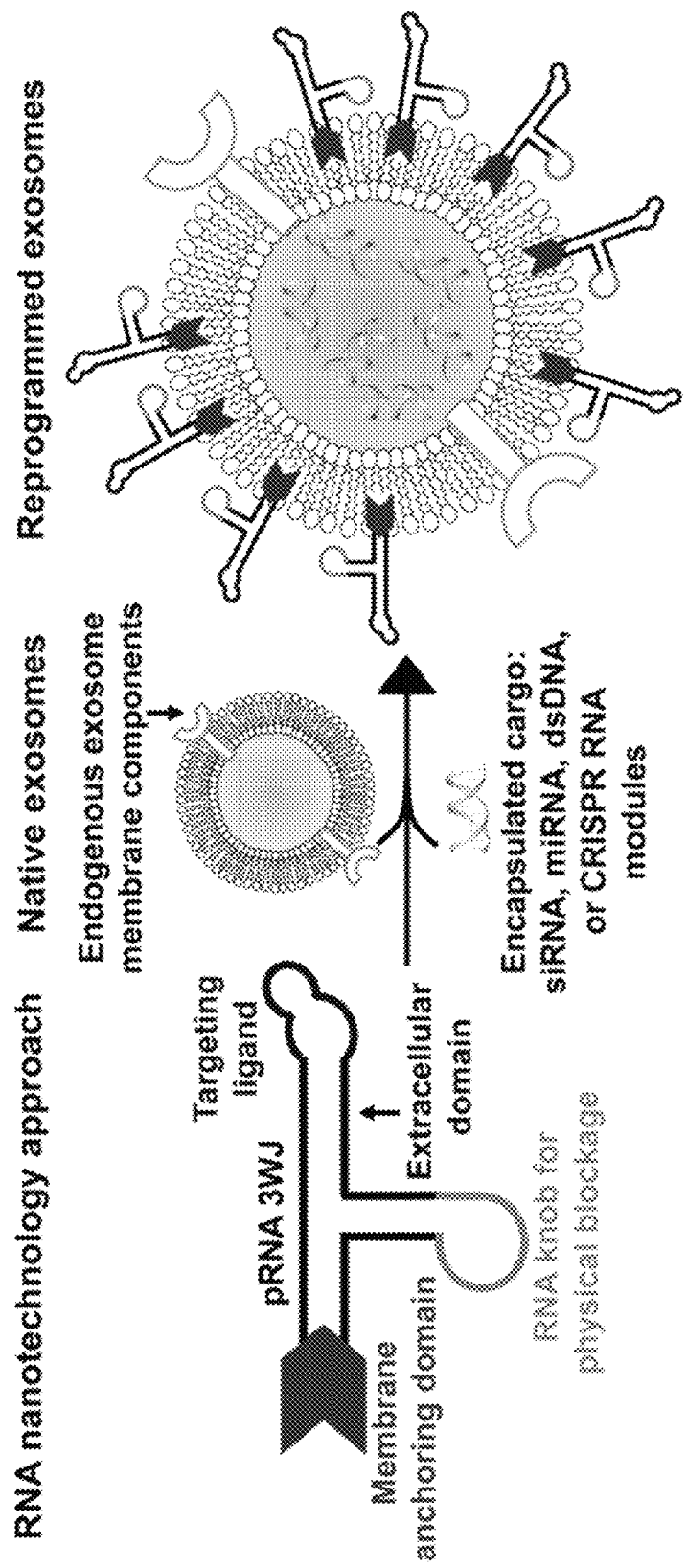
FIG. 1 shows RNA nanotechnology approach for programming native exosomes. Decoration of exosomes with RNA nanoparticles harboring hydrophobic domain for membrane anchorage; targeting ligands for specific cell binding; and RNA knobs for physical hindrance to block encapsulation in exosomes. The cargoes packaged into exosome for cell delivery include siRNA, miRNA, dsDNA or CRISPR-RNA modules.

The disclosed subject matter can be understood more readily by reference to the following detailed description, the figures, and the examples included herein.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

It is understood that the disclosed methods and systems are not limited to the particular methodology, protocols, and systems described as these may vary. It is also to be understood that the terminology used herein is for the purpose of describing particular embodiments only, and is not intended to limit the scope of the present invention which are limited only by the appended claims.

SiRNA and miRNA have the potential to silence genes, DNA can rescue genes, and RNA modules can edit genomes by CRISPR approach. But, their delivery to the cell cytosol in human body has been a major impediment. Several synthetic nanoplatforms have been pursued with certain degree of success in specific cancer targeting and delivery, but the nanoparticles can get trapped by Kupffer cells in the liver, and macrophages in the lung and spleen, leading to low efficiency of reaching target cells and non-specific toxicity or side-effects. One strategy is to use exosomes for delivery of therapeutics. Exosomes are capable of crossing heterogeneous biological barriers to deliver their contents to recipient cells without getting trapped in endosomes. They are well tolerated in vivo and can be immunogenically inert. However, they lack selectivity and can randomly fuse with normal cells as well. For clinical translation, a major hurdle is to reprogram these naturally derived exosomes to harbor targeting ligands to ensure delivery to diseased cell specifically. A limited number of publications has demonstrated that exosomes with in vivo expressed protein ligands can enhance targeting of specific cells. However, in vivo expression of protein ligands is limited to the availability of ligand species and depends on exosome and ligand expressing cell types. The use of protein ligands result in larger sized exosomes that get trapped in the liver, lungs and spleen. The lower frequency of molecule display on exosome surface cannot efficiently reduce their binding and fusion rate to healthy cells.

Approaches using RNA interference, gene delivery, and CRISPR mediated genome editing are promising, but the significant challenge in clinical therapeutics by these technologies is the low efficiency and limited specificity to selectively target diseased cells. Nonspecific entry and accumulation in healthy organs significantly reduces the therapeutic index, and results in often severe side effects. RNAi agents have incredible potentials as therapeutics, but in their native form are prone to degradation in the serum, are rapidly cleared from the blood, can illicit immune responses, and their negative charge limits cell membrane passage and cellular uptake. Several nanodelivery platforms have been developed to address these problems, but hurdles still remain, such as toxicity, immunogenicity, liver accumulation, and entrapment in endosomes. Naturally derived exosomes can be derived for targeted delivery of RNA or DNA therapeutics to diseased cells with little or no collateral damage to healthy cells.

Targeted delivery is extremely important in medicine, including siRNA/miRNA delivery for RNAi therapy, gene delivery to remedy genetic deficiency, nucleic acid delivery for DNA repair, and chemotherapeutic delivery for all kind of diseases. Both exosomes and RNA nanotechnology fields have demonstrated potentials for in vivo delivery of therapeutics. However, currently each field is deficient in one critical aspect to meet the clinical translational goal: (1) Exosomes can efficiently enter cells by membrane fusion and deliver functionally active proteins and RNA/DNA to induce transcriptional and translational changes in the target cell; however, cell entry by fusion is nonspecific and specific cell targeting has not been resolved. (2) RNA nanoparticles constructed via RNA nanotechnology can efficiently and specifically target cancer cells, but the RNA nanoparticles can get trapped in endosomes after cell entry and the endosome escape efficiency is still low.

The disclosed strategy is to display RNA nanoparticles harboring RNA aptamers or chemical ligands on exosome surface by RNA nanotechnology approach (FIG. 1). The in vitro display and decoration technology using purified exosomes and RNA nanoparticles result in high frequency of RNA ligand display to block non-specific fusion of exosomes with healthy cells due to physical hindrance. The display of RNA or chemicals ligands by the in vitro approach expands the scope of targeting ligand variety, facilitates industrial scale production, and enables the repeated treatment of chronic diseases due to the non-induction of host immune responses by RNA or chemical reagents. The disclosed approach takes advantages of both the exosomes and RNA nanotechnology platforms to achieve specific targeting, high efficiency for specific cell entry, and optimal functionality of siRNA, miRNA, mRNA or dsDNA after in vivo delivery into the cytosol.

Exosomes are 20-100 nm specialized membranous vesicles derived from endocytic compartments that are released by many cell types. The importance of exosomes in mediating fundamental elements of cell-cell communication via the transfer of bioactive lipids, cytoplasmic and membrane proteins, and RNA have been confirmed in numerous studies. In cancer, exosomes are capable of stimulating angiogenesis, inducing tumor proliferation and metastasis, and promoting immune escape. Exosomes have great potentials as delivery vectors, since they: (1) are easy to extract and reengineer; (2) are well-tolerated in vivo, since they are already secreted by most cells; (3) are inert immunogenically, if derived from appropriate cells; (4) can be patient-derived for personalized therapy. They are less likely to be attacked by the innate immune cells, antibodies, complement or coagulation factors in the circulation of the patient; (5) are naturally capable of intracellular delivery of biomolecules based on their inherent ability to transfer their content to recipient cells; (6) possess large surface area for displaying multiple targeting ligands; (7) have nanoscale size and elastic (deformable) shape with intrinsic ability to cross biological barriers, such as blood-brain barrier, and avoid renal and hepatic clearance; and, (8) can circumvent the need for endosomal-escape strategies since exosomes can directly fuse with the cell membrane through their tetraspanin domains interacting with surface glycoproteins on the target cell and deliver contents directly to cytosol. They can also back-fuse with endosomal compartment membranes following receptor-mediated endocytosis to release their encapsulated cargo to cytosol. Thus, the therapeutic payloads such as miRNA, siRNA, dsDNA or mRNA can be fully functional after delivery into the cell.

RNA has unique properties as a construction material based on the following aspects: (1) RNA is a polymer that can be used for controlled synthesis with defined structure, size and stoichiometry; they can thus avoid nonspecific side effects arising from particle heterogeneity. (2) RNA nanoparticles have dimensions of 10-50 nm, depending on the shape and stoichiometry, and sufficient to harbor aptamers as cell targeting ligands. (3) Elastic nature and branched ratchet shape of RNA nanoparticles facilitates cancer cell membrane binding, crossing and entry via receptor-mediated endocytosis. This is particularly useful for overcoming mechanical barriers, disorganized vasculatures, and highly immunosuppressive tumor microenvironments. (4) Modular design and bottom up self-assembly makes economic industrial scale production possible. (5) RNA nanoparticles are highly soluble, not prone to aggregation, and do not require linkage to PEG or albumins, typically used for protein-based reagents. (6) Polyvalent nature allows simultaneous incorporation of multiple targeting and imaging modules without any cross-linking. (7) pRNA-3WJ nanoparticles are thermodynamically stable, which ensures the correct folding and independent activity of the incorporated functional modules. (8) pRNA-3WJ constructs display chemical stability after 2'-Fluoro (2'-F) modifications; the in vivo half-life is tunable based on the number and location of 2'-F nucleotides in the RNA sequence. (9) pRNA-based nanoparticles display favorable PK/PD profiles; are non-toxic; and do not induce interferon or cytokine production in mice, even after repeated administrations of 30 mg/kg. RNA nanoparticles do not contain proteins and do not induce host antibody responses, which allow for repeated treatment of cancer. (10) Upon systemic injection, pRNA-3WJ nanoparticles within 3-4 hrs specifically accumulate in tumors, and are cleared from healthy organs, such as liver, lungs, spleen and kidneys. (11) Finally, RNA is classified as a chemical reagent. Regulatory processes are expected to be much more favorable compared to protein-based clinical reagents.

Exosomes have shown efficient cell entry and potent endosome escape capabilities; however, lack of specific cell targeting has led to low therapeutic efficacy. Non-specific fusion to healthy cells and significant accumulation in liver and other healthy vital organs has resulted in toxicity. A few publications indicated that exosomes can be engineered to express certain cell-type-specific protein-based targeting ligands on their surface via genetic fusion of targeting protein encoding gene to the exosome trans-membrane proteins, such as LAMP2. However, in vivo expression of protein ligands is limited to the availability of ligands and depends on exosome and ligand producing cell types. In addition, the use of protein ligands result in larger sized particles that can get trapped in liver, lung and other organs, and can stimulate the production of host antibodies. Degradation of targeting peptides by endosomal proteases often occurs during exosome biogenesis, which further limits their capabilities. Other challenges include large scale production and purification of exosomes from donor cells and inefficient loading of therapeutic cargoes into exosomes. Although RNA nanotechnology has progressed rapidly, the use of RNA nanoparticles for in vivo delivery via receptor mediated endocytosis has resulted in trapping of RNA nanoparticles in endosomes and consequently limited efficacy of the delivered therapeutic cargoes.

Definitions

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not.

As used herein, the terms "transformation" and "transfection" mean the introduction of a nucleic acid, e.g., an expression vector, into a recipient cell including introduction of a nucleic acid to the chromosomal DNA of said cell. The art is familiar with various compositions, methods, techniques, etc. used to effect the introduction of a nucleic acid into a recipient cell. The art is familiar with such compositions, methods, techniques, etc. for both eukaryotic and prokaryotic cells. The art is familiar with such compositions, methods, techniques, etc. for the optimization of the introduction and expression of a nucleic acid into and within a recipient cell.

The term "biocompatible" generally refers to a material and any metabolites or degradation products thereof that are generally non-toxic to the recipient and do not cause any significant adverse effects to the subject.

The term "biodegradable" generally refers to a material that will degrade or erode under physiologic conditions to smaller units or chemical species that are capable of being metabolized, eliminated, or excreted by the subject. The degradation time is a function of polymer composition and morphology. Suitable degradation times are from days to months.

The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen.

The terms "peptide," "protein," and "polypeptide" are used interchangeably to refer to a natural or synthetic molecule comprising two or more amino acids linked by the carboxyl group of one amino acid to the alpha amino group of another.

The term "protein domain" refers to a portion of a protein, portions of a protein, or an entire protein showing structural integrity; this determination may be based on amino acid composition of a portion of a protein, portions of a protein, or the entire protein.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (R A).

The term "specifically binds", as used herein, when referring to a polypeptide (including antibodies) or receptor, refers to a binding reaction which is determinative of the presence of the protein or polypeptide or receptor in a heterogeneous population of proteins and other biologies. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism.

A "chimeric molecule" is a single molecule created by joining two or more molecules that exist separately in their native state. The single, chimeric molecule has the desired functionality of all of its constituent molecules. Frequently, one of the constituent molecules of a chimeric molecule is a "targeting molecule" or "targeting moiety." The targeting molecule is a molecule such as a ligand or an antibody that specifically binds to its corresponding target, for example a receptor on a cell surface.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule.

Typically specific delivery results in a much stronger association between the delivered molecule and cells bearing the target molecule than between the delivered molecule and cells lacking the target molecule.

A "spacer" as used herein refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

The term "vector" or "construct" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element).

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules.

As used herein, the term "amino acid sequence" refers to a list of abbreviations, letters, characters or words representing amino acid residues. The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

The term "variant" refers to an amino acid or peptide sequence having conservative amino acid substitutions, non-conservative amino acid subsitutions (i.e. a degenerate variant), substitutions within the wobble position of each codon (i.e. DNA and RNA) encoding an amino acid, amino acids added to the C-terminus of a peptide, ora peptide having 60%, 70%, 80%, 90%, 91%, 92%, 93%, 94%, 95%, 96%, 97%, 98%, or 99%) percent identity to a reference sequence.

The term "percent (%) sequence identity" or "homology" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods. In an aspect, the one or more therapeutic agents are selected from one or more antimicrobial compounds, one or more antibacterial compounds, one or more antifungal compounds, or one or more anti-cancer agents, or a combination thereof. In an aspect, a disclosed therapeutic composition can comprise one or more anti-cancer agents. In an aspect, the one or more anti-cancer agents can comprise cisplatin. In an aspect, the one or more anti-cancer drugs induce apoptosis. In an aspect, a disclosed therapeutic composition can comprise one or more chemotherapeutic drugs. In an aspect, a disclosed therapeutic composition can comprise one or more radiosensitizers. In an aspect, a disclosed therapeutic composition can comprise a pharmaceutically acceptable carrier.

As used herein, the term "subject" refers to the target of administration, e.g., an animal. Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a patient. A patient refers to a subject afflicted with a disease or disorder, such as, for example, cancer and/or aberrant cell growth. The term "patient" includes human and veterinary subjects. In an aspect, the subject has been diagnosed with a need for treatment for cancer and/or aberrant cell growth.

The terms "treating", "treatment", "therapy", and "therapeutic treatment" as used herein refer to curative therapy, prophylactic therapy, or preventative therapy. As used herein, the terms refers to the medical management of a subject or a patient with the intent to cure, ameliorate, stabilize, or prevent a disease, pathological condition, or disorder, such as, for example, cancer or a tumor. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In an aspect, the disease, pathological condition, or disorder is cancer, such as, for example, breast cancer, lung cancer, colorectal, liver cancer, or pancreatic cancer. In an aspect, cancer can be any cancer known to the art.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed. For example, in an aspect, preventing can refer to the preventing of replication of cancer cells or the preventing of metastasis of cancer cells.

As used herein, the term "diagnosed" means having been subjected to a physical examination by a person of skill, for example, a physician or a researcher, and found to have a condition that can be diagnosed or treated by compositions or methods disclosed herein. For example, "diagnosed with cancer" means having been subjected to a physical examination by a person of skill, for example, a physician or a researcher, and found to have a condition that can be diagnosed or treated by a compound or composition that alleviates or ameliorates cancer and/or aberrant cell growth.

As used herein, the terms "administering" and "administration" refer to any method of providing a composition to a subject. Such methods are well known to those skilled in the art and include, but are not limited to, intracardiac administration, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed composition or peptide or pharmaceutical preparation and a cell, target receptor, or other biological entity together in such a manner that the compound can affect the activity of the target (e.g., receptor, transcription factor, cell, etc.), either directly; i.e., by interacting with the target itself, or indirectly; i.e., by interacting with another molecule, co-factor, factor, or protein on which the activity of the target is dependent.

As used herein, the term "determining" can refer to measuring or ascertaining a quantity or an amount or a change in expression and/or activity level.

As used herein, the terms "effective amount" and "amount effective" refer to an amount that is sufficient to achieve the desired result or to have an effect on an undesired condition. For example, in an aspect, an effective amount of the polymeric nanoparticle is an amount that kills and/or inhibits the growth of cells without causing extraneous damage to surrounding non-cancerous cells. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts.

By "modulate" is meant to alter, by increase or decrease. As used herein, a "modulator" can mean a composition that can either increase or decrease the expression level or activity level of a gene or gene product such as a peptide. Modulation in expression or activity does not have to be complete. For example, expression or activity can be modulated by about 10%, 20%, 30%, 40%, 50%, 60%, 70%, 80%, 90%, 95%, 99%, 100% or any percentage in between as compared to a control cell wherein the expression or activity of a gene or gene product has not been modulated by a composition.

The term "pharmaceutically acceptable" describes a material that is not biologically or otherwise undesirable, i.e., without causing an unacceptable level of undesirable biological effects or interacting in a deleterious manner. As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "cancer" refers to a proliferative disorder or disease caused or characterized by the proliferation of cells which have lost susceptibility to normal growth control. The term "cancer" includes tumors and any other proliferative disorders. Cancers of the same tissue type originate in the same tissue, and can be divided into different subtypes based on their biological characteristics. Cancer includes, but is not limited to, melanoma, leukemia, astrocytoma, glioblastoma, lymphoma, glioma, Hodgkin's lymphoma, and chronic lymphocyte leukemia. Cancer also includes, but is not limited to, cancer of the brain, bone, pancreas, lung, liver, breast, thyroid, ovary, uterus, testis, pituitary, kidney, stomach, esophagus, anus, and rectum.

As used herein, the term "anti-cancer" or "anti-neoplastic" drug refers to one or more drugs that can be used to treat cancer and/or aberrant cell growth.

Disclosed are the components to be used to prepare a composition disclosed herein as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions disclosed herein. Thus, if there are a variety of additional steps that can be performed it is understood that each of these additional steps can be performed with any specific embodiment or combination of embodiments of the methods disclosed herein.

All patents, patent applications, and other scientific or technical writings referred to anywhere herein are incorporated by reference in their entirety. The disclosed subject matter can be practiced in the absence of any element or elements, limitation or limitations that are not specifically disclosed herein. Thus, for example, in each instance herein any of the terms "comprising", "consisting essentially of", and "consisting of" can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed can be resorted to by those skilled in the art, and that such modifications and variations are considered to be within the scope of this invention as defined by the description and the appended claims.

Compositions

Disclosed herein are compositions and methods that involve exosomes displaying RNA nanoparticles on their surface. These exosomes can be used, for example, to target agents to cells. These agents can be incorporated into the nanoparticle, separately displayed on the surface of the exosome, or incorporated as cargo within the exosome.

RNA nanoparticles can be fabricated with a level of simplicity characteristic of DNA, while possessing versatile tertiary structures and catalytic functions that mimic some proteins.

In some embodiments, the RNA nanoparticle is assembled from three or more RNA oligonucleotides duplexed together to form a secondary structure with three or more projecting stem loops. The number, length, and relative angle of each stem loop can be designed to provide stoichiometric advantages. For example, a nanoparticle is disclosed herein with an "arrow-tail" configuration. In this embodiment, one stem loop has an approximate angle of 60 degrees with another stem loop, but an approximate angle of 180 with the other stem loop. This can create a "hook" effect that can lock the RNA nanoparticle in place. Moreover, the nanoparticle will present differently on the exosome depending on which stem loop is anchored in the membrane. Therefore, the shape of the nanoparticle can be tuned to better display or protect moieties as needed. Other shapes are contemplated, such as shapes derived from the "hook" shape. In some embodiments, the nanoparticle maintains an asymmetrical orientation.

As disclosed herein, RNA nanoparticles can be fabricated with precise control of shape, size and stoichiometry. In some embodiments, at least one of the three or more RNA oligonucleotides is derived from a pRNA 3-way junction (3WJ) motif.

In some embodiments, at least one of the three or more RNA oligonucleotides is derived from a bacteriophage packaging RNA (pRNA). pRNA of the bacteriophage phi29 DNA packaging motor forms dimmers, trimers, and hexamers via hand-in-hand interactions of the interlocking loops.

In some embodiments, at least one of the three or more RNA oligonucleotides comprise a natural or modified 3-way junction (3WJ) motif from a pRNA. 3WJ motifs can be found, for example, in GA1, SF5, M2, B103, and phi29 bacteriophage pRNA. The 3WJ assembles from three RNA oligos with unusually high affinity in the absence of metal salts; is resistant to denaturation by 8 M urea; displays thermodynamically stable properties; and does not dissociate at ultra-low concentrations. 2'-Fluoro (2'-F) modification can be used to creat RNA nanoparticles resistant to RNase degradation, while retaining authentic folding and biological activities. Therefore, in some embodiments, the RNA nanoparticle can be assembled from an a3WJ RNA oligonucleotide (SEQ ID NO:1), a b3WJ RNA oligonucleotide (SEQ ID NO:2), and a c3WJ RNA oligonucleotide (SEQ ID NO:3). In some embodiments, the RNA oligonucleotides comprise an artificial and/or synthetic 3WJ motif that yields an asymmetrical orientation.

In some embodiments, the molecule has zeta potential ranging from about −150 mV to about 150 mV. The RNA molecule has a zeta potential ranging from about −140 mV to about 140 mV, from about −130 mV to about 130 mV, from about −120 MV to about 120 mV, from about −110 mV to about 110 mV. In some embodiments, the molecule has zeta potential ranging from about −100 mV to about 100 mV. The RNA molecule has a zeta potential ranging from about −95 mV to about 95 mV, from about −90 mV to about 90 mV, from about −85 mV to about 85 mV, from about −80 mV to about 80 mV, from about −75 mV to about 75 mV, from about −70 to about 70 mV, form about −65 mV to about 65 mV, from about −60 mV to about 60 mV, from about −55 mV to about 55 mV, from about −50 mV to about 50 mV. The molecule has a zeta potential ranging from about −45 my to about 45 mV, from about −40 mV to about 40 mV, from about −35 mV to about 35 mV, from about −35 mV to about 30 mV, from about −35 mV to about 20 mV, from about −25 mV to about 15 mV.

In some embodiments, the RNA nanostructure molecule is substantially stable in pH ranges from about 2 to about 13. The RNA molecule is substantially stable in pH about 2, 3, 4, 5, 6, 7, 8, 9, 10, 11, 12 and 13. As used herein, the term "substantially stable" can refer to physical and/or chemical stability. As will be recognized by those of ordinary skill in the art, the term "substantially stable" can refer to stability of the composition under certain conditions, relative to an initial composition (i.e., when a particular batch of the composition is initially prepared). In this regard, as will be recognized by those of ordinary skill in the art, one manner in which stability of a particular embodiment of the composition can be determined is as follows: preparing a batch of the embodiment of the composition, making an initial assessment of a sample of the composition (control sample), subjecting a sample of the composition to conditions of interest (e.g., storage at a particular condition for a particular time period) (test sample), making an assessment of the test sample, and comparing the assessment of the control sample to the assessment of the test sample. Calculations can be made to determine whether the amounts present in the test sample are 100%+20, 19, 18, 17, 16, 15, 14, 13, 12, 11, 10, 9, 8, 7, 6, 5, 4, 3, 2, 1, 0.5, or 0.1% of the amount that is in the control sample.

RNA is one of the five most important biological macromolecules in addition to DNA, proteins, lipids and carbohydrates. With some aspects similar to DNA, RNA, composed of four nucleotides including adenosine (A), cytosine (C), guanosine (G) and uridine (U), is special in its homogeneity. RNA is a homopolymer of nucleotide, but is also a heteropolymer of A, U, G, and C. Each nucleotide contains a ribose sugar, a nucleobase, and a phosphate group. The nucleotides are covalently linked together through 3'→5' phosphodiester bonds between adjacent ribose units, giving the directionality to the sugar-phosphate backbone that defines RNA as a polynucleic acid. The phosphate moieties in the backbone are negatively charged, making RNA a polyanionic macromolecule at physiological pH. RNA molecules are typically single-stranded; however, Watson-Crick (canonical) base-pair interactions (A:U and G:C), wobble base pairing (such as G:U), or other non-canonical base pairing such as twelve basic geometric families of edge-to-edge interaction (Watson-Crick, Hoogsteen/CH or sugar edge) with the orientation of glycosidic bonds relative to the hydrogen bonds (cis or trans), all together give rise to various structural conformations exhibiting loops, hairpins, bulges, stems, pseudoknots, junctions, etc., which are essential elements to guide and drive RNA molecules to assemble into desired structures.

The characteristic of RNA that defines and differentiates it from DNA is the 2'-hydroxyl on each ribose sugar of the backbone. The 2'-OH group offers RNA a special property, which can be either an advantage or a disadvantage. From a structural point of view, the advantage of this additional hydroxyl group is that it locks the ribose sugar into a 3'-endo chair conformation. As a result, it is structurally favorable for the RNA double helix to adopt the A-form which is approximately 20% shorter and wider rather than the B-form that is typically present in the DNA double helix. Moreover, the 2'-OH group in RNA is chemically active and is able to initiate a nucleophilic attack on the adjacent 3' phosphodiester bond in an S 2 reaction. This cleaves the RNA sugar-phosphate backbone and this chemical mechanism underlies the basis of catalytic self-cleavage observed in ribozymes. The disadvantage is that the 2'-OH group makes the RNA susceptible to nuclease digestion since many RNases recognize the structure of RNAs including the 2'-OH group as specific binding sites.

However, such enzymatic instability can be overcome by applying chemical modification of the 2'-OH group. For example, the substitution of the 2' hydroxyl group with a Fluorine (2-F), Omethyl (2'-0-Me) or Amine (2'-N¾) dramatically increases the stability of RNA in vivo by preventing degradation by RNases. Recent studies also showed that the stability of siRNA in serum is also highly depended on the specific RNA sequences and the degradation of both short and long RNA duplexes mostly occurred at UA/UA or CA/UG sites. Therefore, in some embodiments, the RNA nanoparticle comprises at least one chemical modification at a 2' position of a RNA oligonucleotide. In some embodiments, the chemical modification comprises 2'Fluoro, 2'Amine, and 2'O-Methyl.

In some embodiments, the nanoparticle comprises a membrane-anchoring moiety at one, two, or three of the three or more projecting stem loops. For example, the membrane-anchoring moiety can be a cholesterol molecule.

In some embodiments, the nanoparticle comprises one or more functional moieties at one or more of the remaining stem loops. For example, in some embodiments, the RNA nanoparticles comprises a targeting moiety at one or more of the remaining stem loops. Targeting moieties, such as chemical or nucleic acid based ligands, can be selected to target particular tissue types such as muscle, brain, liver, pancreas and lung for example, or to target a diseased tissue such as a tumor. In some embodiments, the RNA nanoparticles comprises more than one functional moiety. In some cases, the exosomes have more than one type of RNA nanoparticle, each with different functional moieties.

In some cases, the ligand is any molecule able to bind a cell surface protein (e.g. receptor). In some cases, the ligand is a chemical ligand, such as folic acid, galactose, or a derivative thereof.

In some embodiments, the ligand is a nucleic acid based ligand, such as an RNA or DNA aptamer. For example, one or more of the projecting stem loops can be an RNA aptamer sequence, or a ligand can be conjugated to a stem loop of the disclosed nanoparticle. Examples of aptamer targets are provided in Table 1 below.

TABLE 1

RNA aptamers for cancer cell targeting

| Aptamer Target | Cancer |
|---|---|
| Transferrin | Leukemia; skin |
| EpCAM | Colorectal; breast |
| PSMA | Prostate |
| HER2 | Breast; Lung |
| HER3 | Breast |
| EGFR | Breast; Lung |

TABLE 1-continued

RNA aptamers for cancer cell targeting

| Aptamer Target | Cancer |
|---|---|
| EGFRvIII | Glioblastoma |
| CEA | Colorectal |
| CD4 | Leukemia |
| CD19 | B-lymphoma |
| PTK7 | Acute leukemia |
| Tenascin C | Breast; Glioma |
| CD44; CD133 (cancer stem cells) | Breast; lymphoma; Melanoma; Lung |

Nucleic acid sequences for the aptamers in Table 1 are known in the art and can be found, for example, in Wilner S E, et al. Molecular Therapy Nucleic Acids. 2012 1(5):e21; Shigdar S, et al. Cancer Sci. 2011 102(5):991-8; Rockey W M, et al. Nucleic Acid Therapeutics. 2011 21(5):299-314; Kim M Y, et al. Nucleic Acid Ther. 2011 21(3):173-8; Chen C B, et al. Proc Natl Acad Sci USA. 2003 100(16):9226-9231; Esposito C L, PLoS One. 2011 6(9):e24071; Liu Y, et al. Biol Chem. 2009 390(2):137-44; Lee Y J, et al. Gastroenterology. 2012 143(1):155-65.e8; Davis K A, et al. Nucleic Acids Res. 1998 26(17):3915-24; Mallikaratchy P R, et al. Nucleic Acids Research. 2011; 39(6):2458-2469; Xiao Z, et al. Chemistry. 2008; 14(6):1769-75; Shangguan D, et al. Clin Chem. 2007 June; 53(6):1153-5; Daniels D A, et al. Proc Natl Acad Sci USA. 2003 Dec. 23; 100(26): 15416-21; Ababneh N, et al. Nucleic Acid Therapeutics. 2013 23(6):401-407; and Shigdar S, et al. Cancer Lett. 2013 Mar. 1; 330(1):84-95, all of which are incorporated by reference herein for the teaching of these aptamers, including the nucleic acid sequences thereof.

In some embodiments, the disclosed exosomes are loaded with a therapeutic or diagnostic agent.

In some embodiments, the diagnostic agent is an imaging moiety. Imaging moieties includes fluorescence dyes, radionuclides, and/or contrast agents.

Non-limiting examples of fluorescent dye include Alexa dyes, Cy dyes or Near Infrared dyes. Further non-limiting examples of fluorescent dye include Alexa dye, Cy dyes, Near Infrared (Near IR or NIR) dyes, including but not limited to, IRdyegoo, Alexae47, Cy5, Cy5.5, Alexa680, Iowa Black RQ, QSY21, IRDyeQC, BBQ650, BHQ-3, Indocyanine green (ICG). In some embodiments, the imaging module comprises a reporter imaging module.

In some embodiments, the term "radionuclide" includes radiolabel peptides and proteins with various isotopes. Non-limiting examples of the radioisotopes includes $^{86}$Y, $^{90}$Y, $^{111}$In, $^{177}$Lu, $^{225}$Ac, $^{212}$Bi, $^{213}$Bi, $^{66}$Ga, $^{67}$Ga, $^{68}$Ga, $^{64}$Cu, $^{67}$Cu, $^{71}$As, $^{72}$As, $^{76}$As, $^{77}$As, $^{65}$Zn, $^{48}$V, $^{203}$Pb, $^{209}$Pb, $^{212}$Pb, $^{166}$Ho, $^{149}$Pm, $^{153}$Sm, $^{201}$Tl, $^{188}$Re, $^{186}$Re and $^{99m}$Tc. In some embodiments, the radionuclide is coupled to more than one stem loop of the RNA nanoparticle. In some embodiment, the radionuclide is chelated by a chelating agent. In some embodiments, the chelating agent is conjugated to at least one stem loop of the RNA nanoparticle. Nonlimiting examples of the chelating agent include EDTA, DOTA, and NOTA.

The term "contrast agent," as used herein, refers to a compound employed to improve the visibility of internal body structures in an image, including but not limited to, an X-ray image or a scanning image (e.g., CAT (Computerized Axial Tomography) scan, MRI (Magnetic Resonance Imaging) scan). The term contrast agent is also referred to herein as a radiocontrast agent. Contrast agents are employed in various diagnostic (e.g., cardiac catheterization) and therapeutic (e.g., vascular shunt placement) procedures. Magnetic resonance imaging (MRI) is a powerful noninvasive technique that provides high quality three dimensional images of tissues, including information on anatomy, function, and metabolism of tissue in vivo. Gadolinium is a common Ti-weighted MRI contrast agent. In some embodiments, the contract agent is a MRI contrast agent. In some embodiments, the MRI contract agent is gastrointestinal MRI, intravenous MRI intravascular (blood pool) MRI tumor-specific MRI hepatobiliary MRI and reticuloendothelial MRI. One non-limiting example of the MRI contrast agent is a gadolinium contrast agent.

In some embodiments, the therapeutic agent is a therapeutic nucleic acid. Therapeutic approaches using nucleic acids, e.g., oligonucleotides, have been studied in detail. These approaches include small interfering RNA (siRNA) as well as antisense to miRNAs that are overexpressed or miRNA mimics of miRNAs that are reduced in disease. It is widely accepted that delivery of therapeutic oligonucleotides is a major bottleneck in the clinical development of these agents. Oligonucleotides are inherently unstable in circulation. They are difficult to penetrate cell membranes in the absence of lipid transfection agents due to their size and charge. While lipid nanoparticles are the current standard method for oligonucleotide delivery, they possess certain limitations. Composed of synthetic ingredients, lipid nanoparticles will decompose in vivo to produce cytotoxic or immunogenic activities. For example, lipid nanoparticles were shown to produce a variety of toxicities including proinflammatory response and activation of toll-like receptor 4 (Kedmi R, et al. Biomaterials. 2010 31:6867-75). The disclosed compostions provide a superior method for delivering therapeutic nucleic acids.

In some embodiments, the therapeutic nucleic acid is a heterologous polynucleotide not typically associated with the exosomes. Thus the therapeutic nucleic acid is in some embodiments not normally associated with exosomes. The therapeutic nucleic acid may be single or double stranded. Non-limiting examples of therapeutic nucleic acid sequences include siRNA, dsRNA, dsDNA, shRNA, mRNA, microRNA, antagomir, antisense, aptamer, and dsRNA/DNA hybrids. In some cases, the agent is a synthetic siRNA comprising 2'-Fluoride modification on purine bases of the passenger stand.

The therapeutic nucleic acid can be chosen on the basis of the desired effect on the cell into which it is intended to be delivered and the mechanism by which that effect is to be carried out. For example, the therapeutic nucleic acid may be useful in gene therapy, for example in order to express a desired gene in a cell or group of cells. Such nucleic acid is typically in the form of plasmid DNA or viral vector encoding the desired gene and operatively linked to appropriate regulatory sequences such as promoters, enhancers and the like such that the plasmid DNA is expressed once it has been delivered to the cells to be treated. Examples of diseases susceptible to gene therapy include haemophilia B (Factor IX), cystic fibrosis (CTFR) and spinal muscular atrophy (SMN-1).

Therapeutic nucleic acid can also be used for example in immunization to express one or more antigens against which it is desired to produce an immune response. Thus, the therapeutic nucleic acid can encode one or more antigens against which is desired to produce an immune response, including but not limited to tumor antigens, antigens from pathogens such as viral, bacterial or fungal pathogens.

The therapeutic nucleic acid can also be used in gene silencing. Such gene silencing may be useful in therapy to switch off aberrant gene expression or in animal model studies to create single or more genetic knock outs. The therapeutic nucleic acid molecules can act as effectors, inhibitors, modulators, and stimulators of a specific activity possessed by a target molecule, or the therapeutic nucleic acid molecules can possess a de novo activity independent of any other molecules.

Therapeutic nucleic acid molecules can interact with any macromolecule, such as DNA, RNA, polypeptides, or carbohydrate chains. Often therapeutic nucleic acids are designed to interact with other nucleic acids based on sequence homology between the target molecule and the therapeutic nucleic acid molecule. In other situations, the specific recognition between the therapeutic nucleic acid molecule and the target molecule is not based on sequence homology between the therapeutic nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with Ka's from the target molecule of less than 10-12 M. For example, aptamers have been isolated that have greater than a 10,000 fold difference in binding affinities between the target molecule and another molecule that differ at only a single position on the molecule (U.S. Pat. No. 5,543,293). It is preferred that the aptamer have a Ka with the target molecule at least 10, 100, 1000, 10,000, or 100,000 fold lower than the ¾ with a background binding molecule. It is preferred when doing the comparison for a polypeptide for example, that the background molecule be a different polypeptide. Representative examples of how to make and use aptamers to bind a variety of different target molecules can be found in U.S. Pat. Nos. 5,476,766, 5,503, 978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Gene expression can also be effectively silenced in a highly specific manner through RNA interference (RNAi). This silencing was originally observed with the addition of double stranded RNA (dsRNA) (FireA, et al. (1998) Nature, 391:806-11; Napoli, C, et al. (1990) Plant Cell 2:279-89; Hannon, G. J. (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, S. M., et al. (2001) Genes Dev., 15: 188-200; Bernstein, E., et al. (2001) Nature, 409:363-6; Hammond, S. M., et al. (2000) Nature, 404:293-6). In an ATP dependent step, the siRNAs become integrated into a multi-subunit protein complex, commonly known as the RNAi induced silencing complex (RISC), which guides the siRNAs to the target RNA sequence (Nykanen, A., et al. (2001) Cell, 107:309-21). At some point the siRNA duplex unwinds, and it appears that the antisense strand remains bound to RISC and directs degradation of the complementary m NA sequence by a combination of endo and exonucleases (Martinez, J., et al. (2002) Cell, 110:563-74). However, the effect of iR A or siR A or their use is not limited to any type of mechanism.

Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer (Elbashir, S. M., et al. (2001) Nature, 411:494 498) (Ui-Tei, K., et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCERS siRNA Construction Kit.

The production of siRNA from a vector is more commonly done through the transcription of a short hairpin RNAs (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors. Disclosed herein are any shRNA designed as described above based on the sequences for the herein disclosed inflammatory mediators.

microRNAs (miRNAs) are small, regulatory noncoding RNAs. miRNA genes are often located within introns of coding or noncoding genes and have also been identified in exons and intergenic regions (Kim V N, et al. Trends Genet. 2006 22:165-73). Endogenous miRNAs are transcribed by RNA polymerase II into a long primary transcript or pri-miRNA. The pri-miRNA is processed to a ~75 nt pre-miRNA by the ribonucleoprotein complex Drosha/DGCR8. Both the pri- and pre-miRNA contain the characteristic hairpin structure. Following cytoplasmic transport by exportin 5, the pre-miRNA is loaded into the Dicer complex which removes the loop of the hairpin. The duplex miRNA, is loaded into the miRISC complex and the strand with the poorer 5' end stability is removed (Schwarz D S, et al. Cell. 2003 115: 199-208). The complex then scans messenger RNA to locate the miRNA's target. Binding of the mature miRNA (via complete hybridization of the 7 nt 5' seed sequence) typically occurs in the 3' UTR of mRNA and results in translational repression. Altered miRNA expression has been observed in all cancers studied to date. miRNA may be oncogenic or tumor suppressive depending upon the miRNA, its' expression level and the type of cancer. Much has been learned in the past 10 years regarding the role of miRNA in HCC, reviewed in (Braconi C, et al. Seminars in oncology. 2011 38:752-63). As is true of most cancers, certain miRNAs have increased expression in the tumors of patients with HCC including miR-221 (Budhu A, et al. Hepatology. 2008 47:897-907; Gramantieri L, et al. Cancer Res. 2007 67:6092-9; Jiang J, et al. Clin Cancer Res. 2008 14:419-27; Pineau P, et al. Proc Natl Acad Sci USA. 2009; Wang Y, et al. J Biol Chem. 2008 283: 13205-15), miR-21 (Budhu A, et al. Hepatology. 2008 47:897-907; Jiang J, et al. Clin Cancer Res. 2008 14:419-27; Meng F, et al. Gastroenterology. 2007 133:647-58; Pineau P, et al. Proc Natl Acad Sci USA. 2009), and miR-181b (Ji J, et al. Hepatology. 2009 50:472-80; Wang B, et al. Oncogene. 2010 29(12): 1787-97). Primary HCC tumors had reduced expression of other miRNAs such as miR-199a-3p (miR-199a*) (Jiang J, et al. Clin Cancer Res. 2008 14:419-27; Murakami Y, et al. Oncogene. 2006 25:2537-45; Wang Y, et al. J Biol Chem. 2008 283: 13205-15), miR-122 (Bai, et al. J Biol Chem. 2009 284:32015-27; Coulouarn C, et al. Oncogene. 2009 28:3526-36; Fornari F, et al. Cancer Res. 2009 69:5761-7; Kutay H, et al. J Cell Biochem. 2006 99:671-8) and miR-26a (Chen L, et al. Molecular therapy: the journal of the American Society of Gene Therapy. 2011 19: 1521-8).

Antagomirs are a specific class of miRNA antagonists that are used to silence endogenous microRNA. For example, custom designed Dharmacon Meridian™ microRNA Hairpin Inhibitors are commercially available from Thermo Scientific. These inhibitors include chemical modifications and secondary structure motifs. Specifically, incorporation of highly structured, double-stranded flanking regions around the reverse complement core significantly increases inhibitor function and allows for multi-miRNA inhibition at subnanomolar concentrations. Other such improvements in antagomir design are contemplated for use in the disclosed methods.

In some cases, the therapeutic agent is an anti-cancer drug. Examples of anti-cancer drugs or anti-neoplastic drugs include, but are not limited to, the following: Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Other anti-neoplastic compounds include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; atrsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocannycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance genie inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; pennyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists;

raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfmosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

As used herein, radiosensitizers make a cancer cell more likely to be damaged. Radiosensitizers enhance the sensitivity of cancer cells and/or a tumor to ionizing radiation, thereby increasing the efficacy of radiotherapy. Examples of radiosensitizers include gemcitabine, 5-fluorouracil, pentoxifylline, and vinorelbine.

Exosomes are produced by many different types of cells including immune cells such as B lymphocytes, T lymphocytes, dendritic cells (DCs) and most cells. Exosomes are also produced, for example, by glioma cells, platelets, reticulocytes, neurons, intestinal epithelial cells and tumor cells. Exosomes for use in the disclosed compositions and methods can be derived from any suitable cell, including the cells identified above. Exosomes have also been isolated from physiological fluids, such as plasma, urine, amniotic fluid and malignant effusions. Non-limiting examples of suitable exosome producing cells for mass production include dendritic cells (e.g., immature dendritic cell), Human Embryonic Kidney 293 (HEK) cells, 293T cells, Chinese hamster ovary (CHO) cells, and human ESC-derived mesenchymal stem cells.

In some embodiments, exosomes are derived from DCs, such as immature DCs. Exosomes produced from immature DCs do not express MHC-II, MHC-I or CD86. As such, such these exosomes do not stimulate na'ive T cells to a significant extent and are unable to induce a response in a mixed lymphocyte reaction. Thus exosomes produced from immature dendritic cells can be used for use in delivery of genetic material.

Exosomes can also be obtained from any autologous patient-derived, heterologous haplotype-matched or heterologous stem cells so to reduce or avoid the generation of an immune response in a patient to whom the exosomes are delivered. Any exosome-producing cell can be used for this purpose.

Exosomes produced from cells can be collected from the culture medium by any suitable method. Typically a preparation of exosomes can be prepared from cell culture or tissue supernatant by centrifugation, filtration or combinations of these methods. For example, exosomes can be prepared by differential centrifugation, that is low speed (<20000 g) centrifugation to pellet larger particles followed by high speed (>100000 g) centrifugation to pellet exosomes, size filtration with appropriate filters (for example, 0.22 μm filter), gradient ultracentrifugation (for example, with sucrose gradient) or a combination of these methods.

The disclosed exosomes may be administered to a subject by any suitable means. Administration to a human or animal subject may be selected from parenteral, intramuscular, intracerebral, intravascular, subcutaneous, or transdermal administration. Typically the method of delivery is by injection. Preferably the injection is intramuscular or intravascular (e.g. intravenous). A physician will be able to determine the required route of administration for each particular patient.

The exosomes are preferably delivered as a composition. The composition may be formulated for parenteral, intramuscular, intracerebral, intravascular (including intravenous), subcutaneous, or transdermal administration. Compositions for parenteral administration may include sterile aqueous solutions which may also contain buffers, diluents and other suitable additives. The exosomes may be formulated in a pharmaceutical composition, which may include pharmaceutically acceptable carriers, thickeners, diluents, buffers, preservatives, and other pharmaceutically acceptable carriers or excipients and the like in addition to the exosomes.

Methods

Also disclosed is a method of targeting an exosome to a cell that involves contacting the cell with a composition comprising an exosome displaying an RNA nanoparticle on its surface, wherein the nanoparticle comprises at least one targeting moiety, wherein the targeting moiety directs the exosome to the cell of interest. For example, in some embodiments, the cell is a cell in a subject, such as a cancer cell. In some embodiments, the RNA nanoparticle further comprises a functional moiety, such as a therapeutic or diagnostic moiety.

Further disclosed is a method of treating disease in a subject, comprising administering to the subject an exosome displaying an RNA nanoparticle on its surface, wherein the nanoparticle comprises at least one targeting moiety, and further wherein the exosome comprises a functional moiety, wherein the functional moiety is capable of treating the disease in the subject. For example, in some embodiments, the disease is an infection. In some embodiments, the disease is a cancer.

Also disclosed is a method of imaging a cell that involves contacting the cell with a composition comprising an exosome displaying an RNA nanoparticle on its surface, wherein the nanoparticle comprises at least one targeting moiety at least one diagnostic moiety. For example, in some embodiments, the cell is a cell in a subject.

Administration

Parenteral administration is generally characterized by injection, such as subcutaneously, intramuscularly, or intravenously. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof. Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include sodium chloride injection, ringers injection, isotonic dextrose injection, sterile water injection, dextrose and lactated ringers injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate.

Antioxidants include sodium bisulfate. Local anesthetics include procaine hydrochloride. Suspending and dispersing agents include sodium carboxymethylcelluose, hydroxypropyl methylcellulose and polyvinylpyrrolidone.

Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment. The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations can be packaged in an ampoule, a vial or a syringe with a needle. All preparations for parenteral administration should be sterile, as is known and practiced in the art.

A therapeutically effective amount of composition is administered. The dose may be determined according to various parameters, especially according to the severity of the condition, age, and weight of the patient to be treated; the route of administration; and the required regimen. A physician will be able to determine the required route of administration and dosage for any particular patient. Optimum dosages may vary depending on the relative potency of individual constructs, and can generally be estimated based on EC50s found to be effective in vitro and in vivo animal models. In general, dosage is from 0.01 mg/kg to 100 mg per kg of body weight. A typical daily dose is from about 0.1 to 50 mg per kg, preferably from about 0.1 mg/kg to 10 mg/kg of body weight, according to the potency of the specific construct, the age, weight and condition of the subject to be treated, the severity of the disease and the frequency and route of administration. Different dosages of the construct may be administered depending on whether administration is by intramuscular injection or systemic (intravenous or subcutaneous) injection.

Preferably, the dose of a single intramuscular injection is in the range of about 5 to 20 µg. Preferably, the dose of single or multiple systemic injections is in the range of 10 to 100 mg/kg of body weight.

Due to construct clearance (and breakdown of any targeted molecule), the patient may have to be treated repeatedly, for example once or more daily, weekly, monthly or yearly. Persons of ordinary skill in the art can easily estimate repetition rates for dosing based on measured residence times and concentrations of the construct in bodily fluids or tissues. Following successful treatment, it may be desirable to have the patient undergo maintenance therapy, wherein the construct is administered in maintenance doses, ranging from 0.01 mg/kg to 100 mg per kg of body weight, once or more daily, to once every 20 years.

In an aspect, a disclosed therapeutic composition can comprise (i) one or more therapeutic agents, (ii) one or more anti-cancer agents, (iii) one or more chemotherapeutic drugs, and/or (iv) one or more radiosensitizers. In an aspect, a disclosed therapeutic composition can comprise one or more anti-cancer agents and one or more chemotherapeutic drugs. In an aspect, a disclosed therapeutic composition can comprise one or more anti-cancer agents and one or more radiosensitizers. In an aspect, a disclosed therapeutic composition can comprise one or more chemotherapeutic agents and one or more radiosensitizers.

In an aspect, a disclosed therapeutic composition can be administered systemically to a subject. In an aspect, the subject can be a mammal. In an aspect, the mammal can be a primate. In an aspect, the mammal can be a human. In an aspect, the human can be a patient.

In an aspect, a disclosed therapeutic composition can be administered to a subject repeatedly. In an aspect, a disclosed therapeutic composition can be administered to the subject at least two times. In an aspect, a disclosed therapeutic composition can be administered to the subject two or more times. In an aspect, a disclosed therapeutic composition can be administered at routine or regular intervals. For example, in an aspect, a disclosed therapeutic composition can be administered to the subject one time per day, or two times per day, or three or more times per day. In an aspect, a disclosed therapeutic composition can be administered to the subject daily, or one time per week, or two times per week, or three or more times per week, etc. In an aspect, a disclosed therapeutic composition can be administered to the subject weekly, or every other week, or every third week, or every fourth week, etc. In an aspect, a disclosed therapeutic composition can be administered to the subject monthly, or every other month, or every third month, or every fourth month, etc. In an aspect, the repeated administration of a disclosed composition occurs over a pre-determined or definite duration of time. In an aspect, the repeated administration of a disclosed composition occurs over an indefinite period of time.

In an aspect, following the administration of a disclosed therapeutic composition, the cells are sensitized to treatment. In an aspect, following the administration of a disclosed therapeutic composition, a subject can be sensitized to treatment. In an aspect, an increased sensitivity or a reduced sensitivity to a treatment, such as a therapeutic treatment, can be measured according to one or more methods as known in the art for the particular treatment. In an aspect, methods of measuring sensitivity to a treatment include, but not limited to, cell proliferation assays and cell death assays. In an aspect, the sensitivity of a cell or a subject to treatment can be measured or determined by comparing the sensitivity of a cell or a subject following administration of a disclosed therapeutic composition to the sensitivity of a cell or subject that has not been administered a disclosed therapeutic composition.

For example, in an aspect, following the administration of a disclosed therapeutic composition, the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, more sensitive to treatment than a cell that has not been administered a disclosed therapeutic composition. In an aspect, following the administration of a disclosed therapeutic composition, the cell can be 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, or greater, less resistant to treatment than a cell that has not been administered a disclosed therapeutic composition. The determination of a cell's or a subject's sensitivity or resistance can be routine in the art and within the skill of an ordinary clinician and/or researcher.

In an aspect, the determination of a cell's or a subject's sensitivity or resistance to treatment can be monitored. For example, in an aspect, data regarding sensitivity or resistance can be acquired periodically, such as every week, every other week, every month, every other month, every 3 months, 6 months, 9 months, or every year, every other year, every 5 years, every 10 years for the life of the subject, for example, a human subject or patient with cancer and/or aberrant cell growth. In an aspect, data regarding sensitivity or resistance can be acquired at various rather than at periodic times. In an aspect, treatment for a subject can be modified based on data regarding a cell's or a subject's sensitivity or resistance to treatment. For example, in an aspect, the treatment can modified by changing the dose of a disclosed compositions, the route of administration of a disclosed compositions, the frequency of administration of a disclosed composition, etc.

EXAMPLES

The following examples are put forth so as to provide those of ordinary skill in the art with a complete disclosure and description of how the compounds, compositions, and methods claimed herein are used and evaluated and are intended to be purely exemplary of the disclosed subject matter and are not intended to limit the scope of what the inventors regard as their invention. However, those of skill in the art should, in light of the present disclosure, appreciate that many changes can be made in the specific aspects which are disclosed and still obtain a like or similar result without departing from the spirit and scope of the invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

In this example, an RNA nanotechnology approach is used to reprogram naturally derived exosomes for targeted delivery of miRNA, siRNA, dsDNA or CRISPR-RNA cargoes to cancer cells (FIG. 1). An ultra-stable 3-Way Junction (3WJ) motif, derived from bacteriophage phi29 DNA packaging motor pRNA as a robust multifunctional scaffold for displaying targeting modules (chemical ligands or RNA aptamers) with authentic fold and functionality on the exosome surface was used. The targeting modules recognize and bind to specific receptors on cancer cell membrane and deliver their therapeutic contents via receptor-mediated endocytosis. The dense network of targeting ligands not only enhances cancer cell specific uptake, but also minimize interactions with normal cells, thus reducing nonspecific cell fusion. The strategy of incorporating a membrane anchoring domain in each 3WJ nanoparticle ensure that the RNA nanoparticle is embedded and hence displayed on the exosome surface, but not encapsulated in the exosomes. The display of non-protein ligands using an in vitro approach expand the scope of ligand variety, facilitates industrial scale production in a cost-effective manner, and enable repeated treatment of cancer due to the non-induction of host antibodies by RNA or chemicals. Importantly, this approach retains all the favorable endogenous properties of exosomes for efficient cell entry, such as lipid composition, as well as membrane embedded exclusive families of exosome proteins (tetraspanins, heat shock proteins, lysosomal proteins, and fusion proteins).

Naturally derived exosomes are biocompatible. They are regularly released from many different cells. The combination of specialized lipids and arrays of membrane proteins contributes to the efficient fusion between exosome and recipient cell. Importantly, use of exosomes can eliminate the need for endosome-escape strategies that have plagued the therapeutic arena.

Incorporation of RNA nanoparticles after exosome extraction ensures that the endogenous composition of exosomes are retained. The in vitro decoration procedure facilitate industry-scale production. Use of RNA ligands further expands the scope of ligand variety beyond certain possibility of binding by antibodies. The negative charge of RNA ligands minimize nonspecific binding to negatively charged cell membranes, thus reducing toxicity.

The pRNA-3WJ nanoparticles used here as scaffold for ligand display has several favorable attributes. They are homogeneous in size, structure and stoichiometry; can be synthesized chemically in large quantities and self-assembled with high efficiency; thermodynamically and chemically stable; non-toxic; non-immunogenic; and display favorable biodistribution and PK/PD profiles. Each incorporated targeting module retained their folding and independent functionalities for specific cell binding and entry in xenograft and metastatic cells in vivo. The crystal structure of pRNA-3WJ has been solved, which has facilitated RNA nanoparticle designs (suitable for displaying ligands with various conformations on exosome surface.

Instead of a single reagent, exosomes can deliver multiple therapeutic reagents at once. In case of miRNA or siRNA, functionally related genes can be suppressed simultaneously. Exosomes have clinical potential not only as a direct method of delivery, but also that once delivered, the therapeutic extent of treatments may be enhanced by exosome-mediated transfer to the cancer associated fibroblasts, extracellular matrix and immune cells in the tumor microenvironment.

Methods and Results

Construction of Membrane-Anchoring RNA Complex Harboring Cell Receptor-Binding RNA Aptamers or Chemical Ligands to Display on Exosome Surface Using RNA Nanotechnology This approach involves (1) constructing multi-functional RNA nanoparticles harboring targeting ligands, imaging agents, and hydrophobic membrane anchoring domain for display on exosome surface; (2) isolating nanosized exosomes for high efficient tumor targeting while avoiding accumulation in healthy organs; and, (3) industry-scale production and purification of RNA nanoparticles and exosomes.

Construction of Multifunctional RNA Nanoparticles for Display on Exosomes

The pRNA-3WJ motif is used as a robust scaffold for constructing multifunctional RNA nanoparticles for exosome surface display. The pRNA-3WJ core utilizes a modular design composed of three fragments which assembles with unusually high affinity in the absence of metal salts, is resistant to denaturation by 8 M urea, is thermodynamically stable, and does not dissociate at ultra-low concentrations. The melting temperature is ~60° C. and the slope of the melting curve is close to 90° indicating extremely low free energy ($\Delta G_{o\ 37^\circ\ C.}$=−28 kcal/mol) and simultaneous assembly of the three fragments. 2'-F modifications resulted in RNA nanoparticles resistant to RNase degradation, while retaining authentic folding and biological activities for the scaffold and all functional modules.

Incorporation of Hydrophobic Membrane Anchoring Domain

Figure 2A:
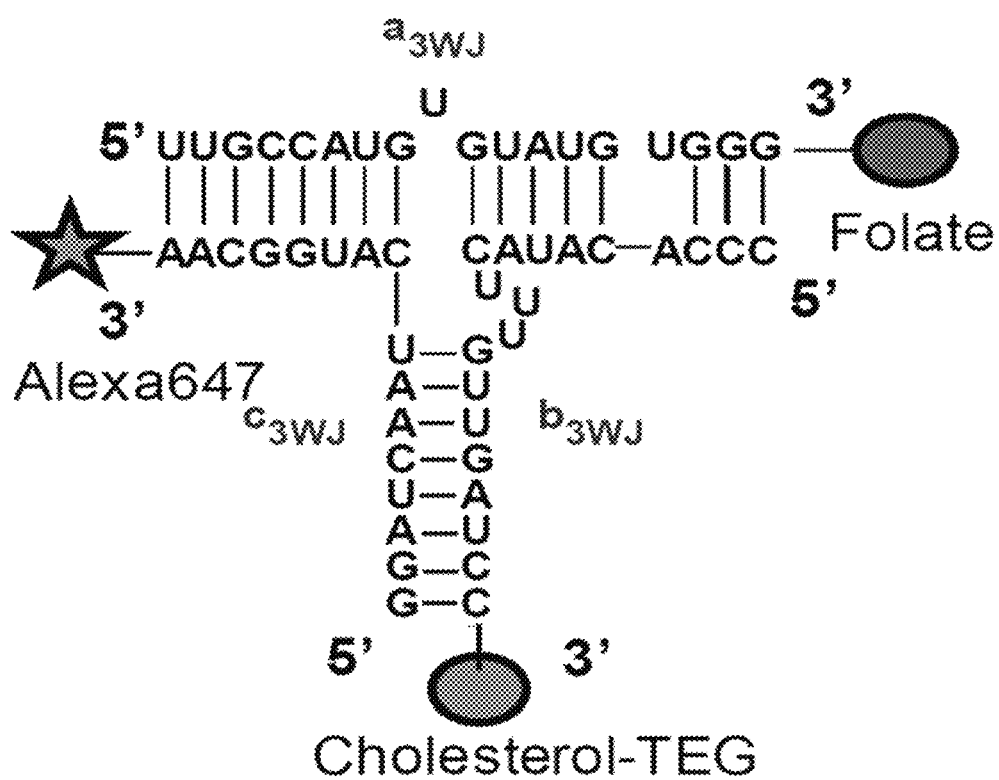
FIGS. 2A and 2B show schematic (FIG. 2A) and assembly (FIG. 2B) of pRNA-3WJ nanoparticles harboring folate for targeting, cholesterol for membrane anchorage; and Alexa-647 for imaging. $a_{3WJ}$(SEQ ID NO:1)-Folate; $b_{3WJ}$ (SEQ ID NO:2)-Cholesterol; $c_{3WJ}$(SEQ ID NO:3)-Alexa647.

Cholesterol phosphoramidites are commercially available (Glen Research) bearing a triethylene glycol (TEG) linker. Cholesterol-TEG labeled oligonucleotides are known to insert spontaneously into the hydrophobic lipid core without altering the membrane structure. One of the pRNA-3WJ strands ($b_{3WJ}$) serving as one domain, are labeled with cholesterol during chemical synthesis using phosphoramidite chemistry (FIG. 2A).

RNA Nanoparticle Design to Ensure Anchoring of the RNA Nanoparticle on Exosome Surface without Entering into the Exosomes:

Besides the design of the hydrophobic membrane anchoring domain, a larger hydrophilic knob is designed into the extracellular domain of the RNA nanoparticles for membrane insertion and surface display. The knob can be constructed using RNA nanoparticles with various shape and structure.

Conjugation of Targeting Ligands to pRNA-3WJ

An emerging class of targeted therapeutic molecules based on RNA aptamers have been generated by in vitro SELEX to bind to cancer cell surface receptors with high selectivity and sensitivity. RNA nanoparticles harboring many different cell receptor binding aptamers (see Table 1) or chemical ligands have been constructed.

The resulting RNA constructs retain their authentic folding and are capable of efficient binding and internalization into cancer cells in vivo. Furthermore, the modular design ensures that each of the strands can be chemically synthesized with high batch fidelity and adaptable modifications for controlled degradation in vivo. The availability and ease of incorporation of these aptamers ensure diversification of exosome targeting ligands for specific targeting of diseased cells and tissues.

Conjugation of Imaging Agents to pRNA-3WJ Scaffold

One of the pRNA-3WJ strands ($c_{3WJ}$) is end-labeled with Alexa-647 fluorophore (FIG. 2A).

Assembly of pRNA-3WJ from Three Functionalized Component Strands

Figure 2B:
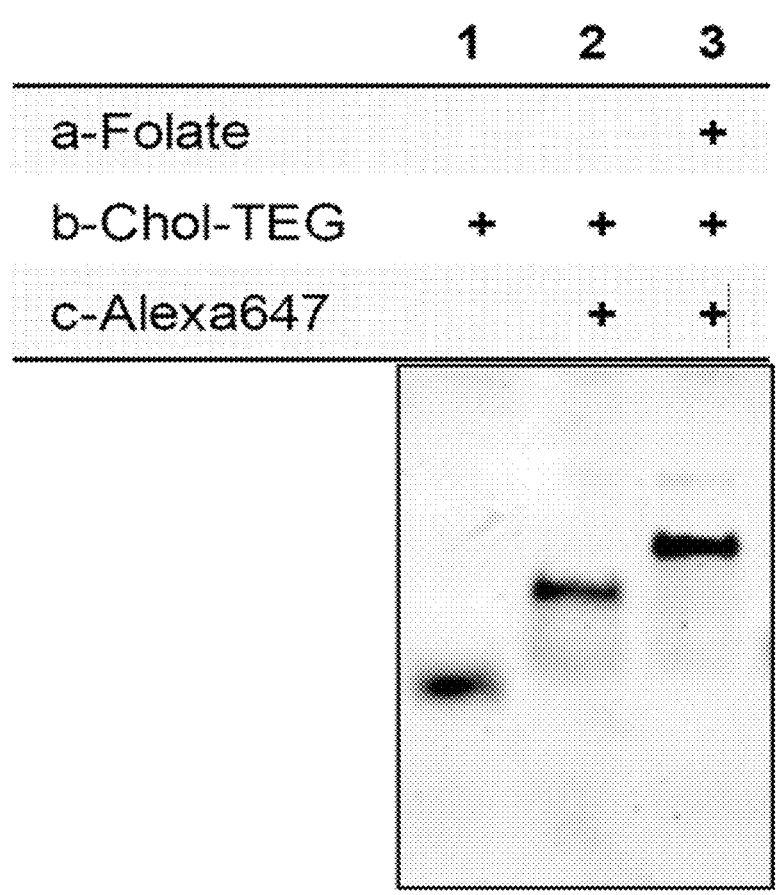

Upon mixing the strands ($a_{3WJ}$-Folate or RNA\aptamer):($b_{3WJ}$-Cholesteol):($c_{3WJ}$-Alexa-647) in 1:1:1 molar ratio, the pRNA-3WJ assembles with high efficiency (FIG. 2B). The biophysical properties of RNA constructs are constructed using well established methods:

(1) Assay RNA nanoparticle folding and assembly using native PAGE gels.

(2) Assess $T_m$ by qPCR with SYBR Green, temperature gradient gel or UV absorbance.

(3) Assess $K_D$ by competition assays using radiolabeled RNA or Surface Plasmon Resonance.

(4) Evaluate chemical stability by incubating RNA with RNase or 50% FBS.

(5) Examine resistance to denaturation by 2-8 M urea in denaturing PAGE gels.

(6) Structural characterization by Atomic Force Microscopy (AFM) imaging; 2D structure prediction by 'm-fold' and other RNA folding algorithms.

All multifunctional pRNA-3WJ constructs harboring functional modules must meet >95% purity after gel or HPLC purifications; display authentic folding and structure, verified by AFM imaging; retain chemical and thermodynamic stable properties, validated by $T_m$ analysis, denaturing gel, and serum stability assays.

Extraction of Exosomes from Non-Immunogenic Human Embryonic Kidney Cell Line 293 (HEK293)

Figures 3C, 3D:
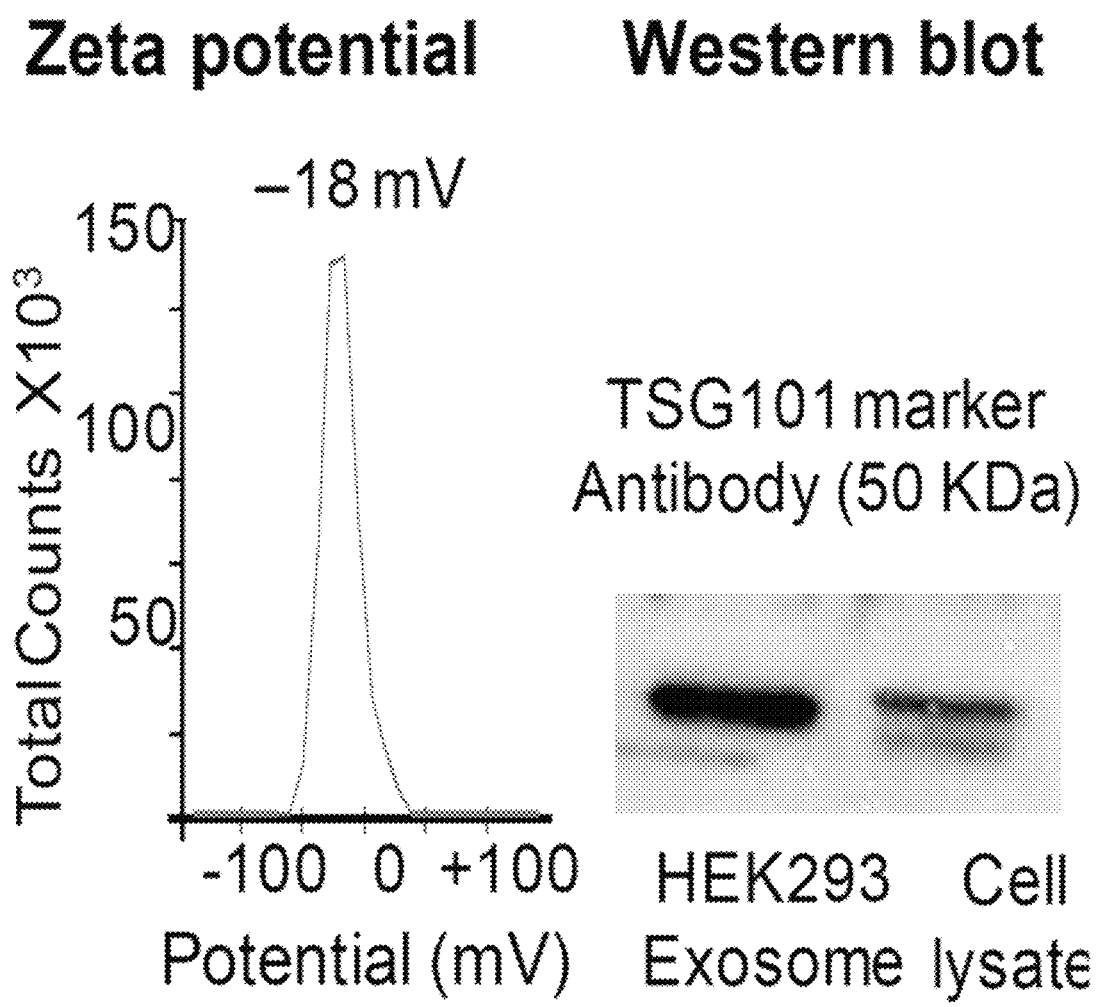

To ensure favorable biodistribution and avoid liver trapping, methods have been developed for extracting high quality exosomes from HEK293 cells without co-purifying protein aggregates and other membranous particles. The exosomes have been characterized by electron microscopy (FIG. 3A), Dynamic Light Scattering (DLS) for size and surface charge (FIG. 3B-C), and proteomic profiling of authentic exosome markers (FIG. 3D).

Large Scale Production and Purification of RNA Nanoparticles and Exosomes

Purification of large quantities of RNA complexes is of paramount importance for animal trials and clinical applications. Procedures for large scale purification of RNA have been developed. Previously, purification was done by HPLC or gel electrophoresis with relatively low yields. A new method of industry-scale purification of RNA using column gel has also been established. An iso-osmotic pressure cushioned gradient ultracentrifugation method has been designed for gentle purification of exosomes without pelleting. This method takes advantage of high density Iodixanol to replace the CsCor sucrose that displays high osmotic pressure, which can damage the exosome. Exosomes purified by this method retain high biological activity and purity, without detrimental effects on the shape and size of the exosomes.

Incorporation of RNA Nanoparticles on Exosome Surface

Figure 4A:
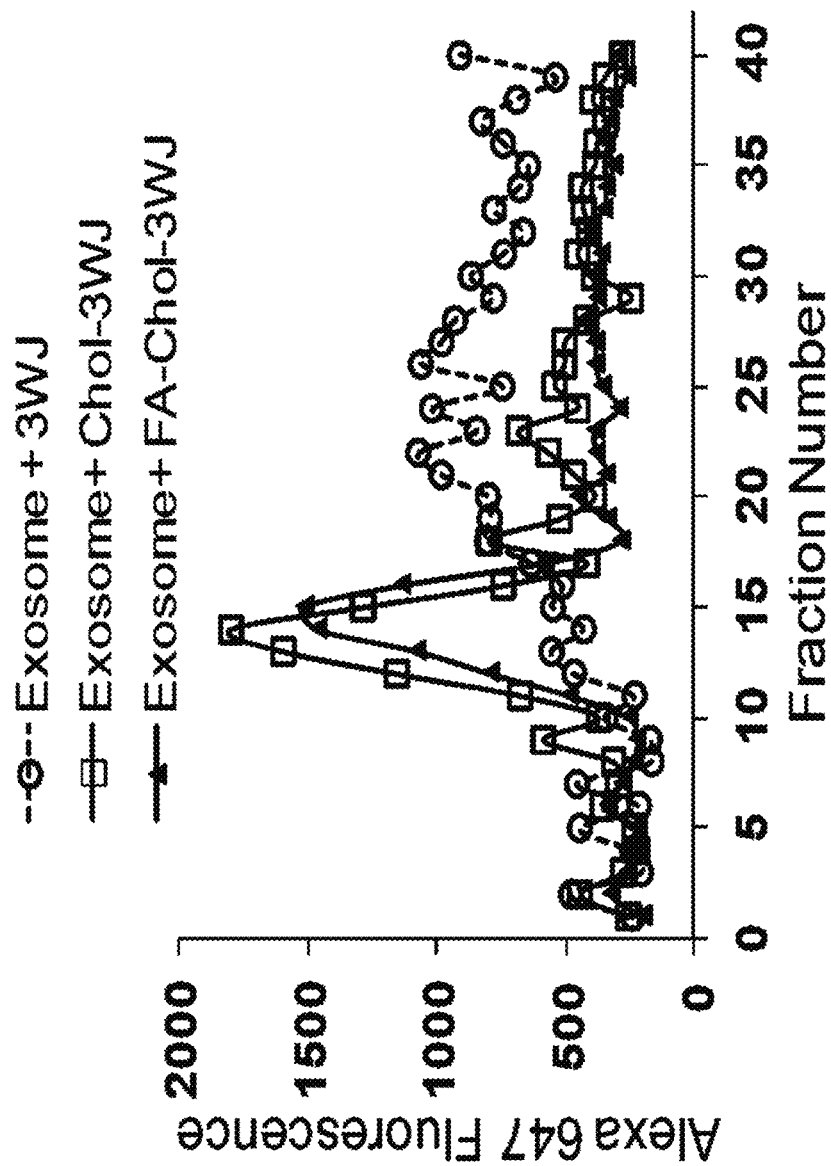
FIG. 4A shows size exclusion purification of exosomes harboring pRNA-3WJ from free RNA.
Figure 4B:
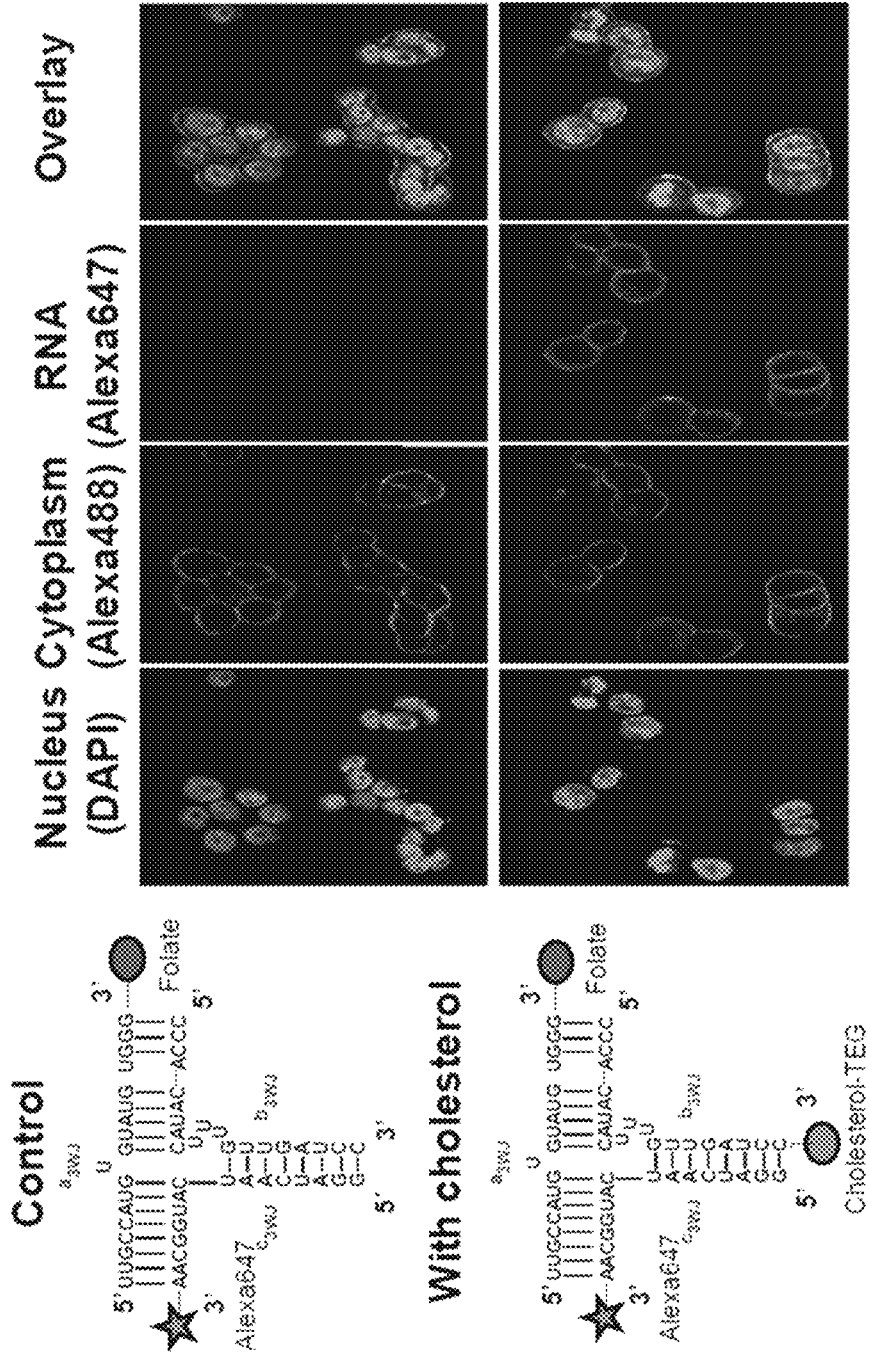
FIG. 4B contains confocal images showing bright fluorescent ring around the cell indicating successful anchorage of cholesterol moiety in the cell membrane (compared to control without cholesterol). $a_{3WJ}$(SEQ ID NO:1)-Folate; $b_{3WJ}$ (SEQ ID NO:2); $b_{3WJ}$(SEQ ID NO:2)-Cholesterol; $c_{3WJ}$(SEQ ID NO:3)-Alexa647.

Fluorescent multifunctional pRNA-3WJ is incubated with purified exosomes. Residual RNA suspensions are removed by size exclusion chromatography (FIG. 4A). Confocal images revealed that cell membranes display bright fluorescence ring, indicating successful anchorage of cholesterol moiety in the membrane without internalization into the cell (FIG. 4B).

Optimization of Exosome Size and Surface Ligand Density to Enhance Tumor Targeting and Improve Biodistribution Profiles In Vivo The size of exosomes are tuned, and the density of targeting ligands displayed on exosome surface is controlled. The size of the exosomes and the density of exosome membrane anchored targeting ligands are critical to ensure that exosomes (1) are specifically delivered to tumors with high efficiency; and (2) are not picked up by healthy cells, which can result in non-specific side effects. Colorectal and liver cancer xenograft and metastases mouse models are used to evaluate the delivery platform. The optimal route of exosome administration (intravenous vs.intraperitoneal) can also be explored to achieve favorable biodistribution and pharmacological profiles (stability; PK; PD; absorption, distribution, metabolism, excretion (ADME); toxicity, and immune responses).

Figure 5A:
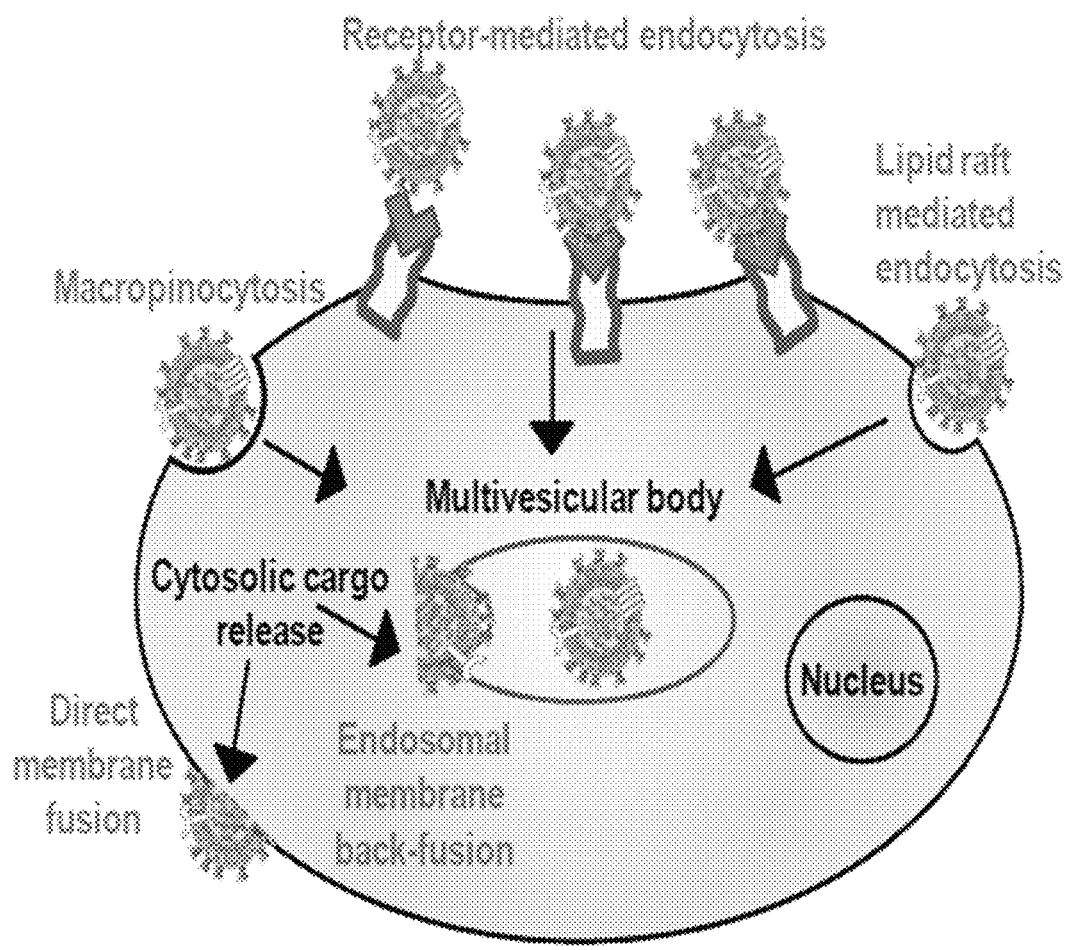
FIG. 5A shows common mechanisms of exosome entry into recipient cells.

Evaluation of the Effect of Ligands Displayed on Exosome Surface for Specific Cell Binding and Entry For cellular binding and uptake studies, exosomes displaying pRNA-3WJ-Folate or other receptor-binding RNA aptamers are incubated with folate or the respective receptor-positive cancer cells and assay by flow cytometry and confocal microscopy, following established procedures. Exosomes were able to efficiently bind and internalize into specific cells (KB, head & neck cancer; and HT29 colorectal cancer) cells by receptor-mediated endocytosis as well as by fusing with the cancer cell membrane (FIGS. 5A and 5B). For in vivo validation, KB cells were generated by subcutaneous xenografts in nude mice and systemically injected exosomes displaying pRNA-3WJ-Folate (or control without folate). Whole body and internal organ imaging revealed that exosomes harboring folate are able to target KB cell tumors with little or no accumulation in healthy vital organs 8-hrs post-administration. The results highlight the differences between 'active; and 'passive' mechanisms of exosome-mediated targeting of tumors.

Tuning of Exosome Surface Ligand Density to Block Nonspecific Cell Entry by Physical Hindrance The high efficient membrane integration of RNA nanoparticles via the membrane anchoring domain makes it possible to decorate high density of RNA ligands on the exosome surface by in vitro approach. Controlling the density of targeting ligands can be achieved simply by titrating the ratio of the pRNA-3WJ nanoparticles (harboring targeting ligands and cholesterol (FIG. 2A) and exosome suspension. It was demonstrated that a ratio of pRNA-3WJ-Folate to Exosome of 300:1 resulted in exosomes that can target folate receptor(+) subcutaneous tumors while avoiding entrapment in healthy organs (FIGS. 6A and 6B). In addition, a range of RNA scaffolds (FIG. 3) are available to present the targeting ligands in specific conformations. The presence of a large number of targeting ligands and in different conformations, as well as overall negative charge of the targeting ligands on exosomes can eliminate nonspecific binding to healthy cells.

Tuning of Exosome Size for Reducing Healthy Organ and Tissue Accumulation

Several studies indicated that intravenous administration of purified exosomes resulted in nonspecific accumulation in the liver, kidney, and spleen. This biodistribution profile is consistent with that of most nanoparticle delivery vehicles, which are generally cleared from circulation through biliary excretion, renal clearance, or reticulo-endothelial system. The optimal size of RNA nanoparticles to avoid nonspecific uptake by liver, lungs, and spleen is in the 10-60 nm range, which is consistent with the observations using 60 nm exosomes showing specific tumor targeting with no accumulation in healthy organs and tissues (FIGS. 6A and 6B). The size of exosomes are variable and dependent on cell type. Ultracentrifugation methods to separate vesicles with different sizes, which can be used for studying the biodistribution profiles, have been found. Alternatively, the size of exosomes can be tuned. Prior experiences have shown that unilamellar liposomal suspensions with low polydispersity can be prepared with polycarbonate membrane filters in an efficient and rapid manner. Herein, the extracted exosome suspension is heated above the phase transition temperature of the exosome lipid mixture and then extrude the suspension through commercially available filters (10 nm, 30 nm, 50 nm, 75 nm and 100 nm) (Avanti Polar Lipids) to generate uniform sized exosomes. Their size and morphology are characterized as well as validate the presence of bona fide exosome markers prior to biodistribution studies.

Characterization of PK/PD and ADME (Absorption, Distribution, Metabolism, Excretion) of Exosome Robust assays for assessing the PK/PD profiles of RNA nanoparticles have been established which are applied for assessment of exosomes. Alexa-647 labeled exosomes are administrated in tumor bearing mice for PK/PD and ADME studies. Key PK parameters, $t_{1/2}$(half-life), AUC (Area Under Curve), $V_d$ (Volume of Distribution), $C_0$ (Concentration at time zero), $C_L$ (Clearance), and MRT (Mean Residence Time) are determined by Capillary Electrophoresis (CE) following a previous publication. The distribution of exosomes into organs and tumors is analyzed by both in vivo and ex vivo experiments following published procedures for RNA nanoparticles using a physiologically-based pharmacokinetic (PBPK) model. This model allows for simulation of optimal dosing required to maximize exosome partitioning into tumors while minimizing accumulation in healthy organs. Non-targeting exosomes are used as control. The excretion pathway of the exosomes is characterized in vivo by studying both the kidney and liver excretion.

Comparison of Intraperitoneal (i.p) vs. Intravenous (i. v) Delivery of Exosomes for Cancer Targeting Systemic injection is often the only strategy capable of delivering therapeutics to metastatic cells. Owing to its localization within the peritoneal cavity, primary colorectal and liver tumors as well as metastatic cells in the liver are further amenable to i.p. administration. I.p injection of standard chemotherapy agents improves treatment outcomes relative to i.v. injection for patients with optimally debulked tumors.

Evaluation of Exosome Binding to Plasma Proteins

Exosome binding to plasma proteins significantly influence their biodistribution, clearance, and therapeutic effects. Commonly used proteomic methods including 2D gel electrophoresis, CE, and LC-MS/MS are used to both qualitatively and quantitatively characterize the plasma proteins (ex. such as albumin, lipoprotein, glycoprotein, and $\alpha$, $\beta$, and $\gamma$ globulins) bound to exosomes.

Evaluation of Toxicity of exosomes

One important criteria for using exosomes as a delivery platform is its safety profile. The systemic acute toxicity of exosomes by determining the $LC_{50}$ in vivo, with approaches refined from a previous publication. 3 different mouse strains (BALB/c, C57BL/6 and Swiss Webster) can be used to provide the greatest opportunity for discovering toxicities. Mice are injected with exosomes at graded dose levels and monitored for mortality, body weight, and signs of toxicity. Blood samples are collected for standard panel clinical chemistry (including PT, aPTT), liver enzymes AST, ALT and LDH (to assess liver toxicity), BUN and creatinine (to assess renal toxicity), and measurement of serum INF-$\alpha$, TNF-$\alpha$, IL-6 and IFN-$\gamma$ (to determine off-target effects). Gross pathology and organ weights are recorded and representative sections are examined for histologic evidence of injury, which includes focal necrosis or hepatitis in the liver, tubular necrosis or nephropathy in the kidney, and diffuse alveolar damage or pneumonitis in the lungs.

Figures 8A, 8B:
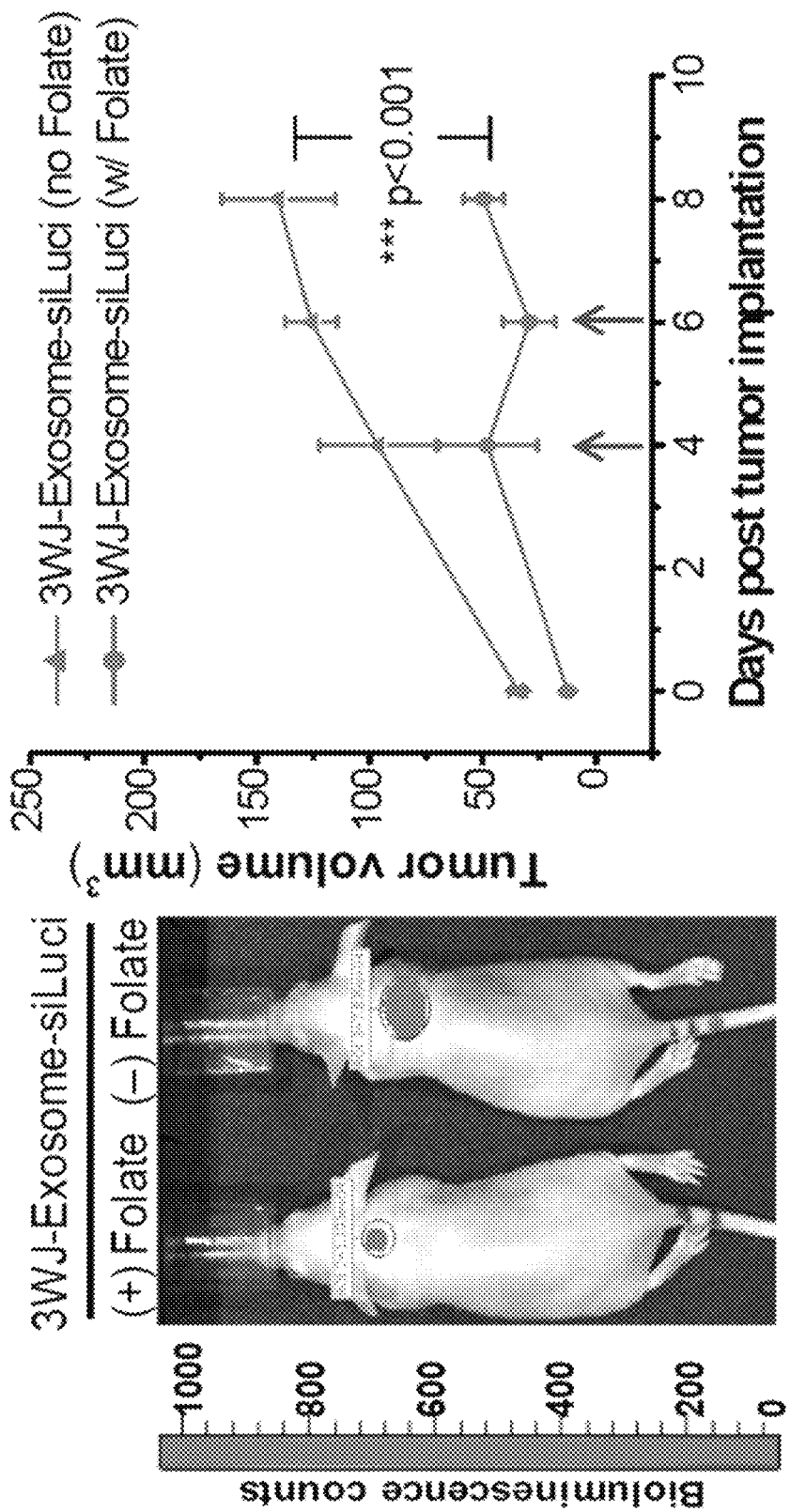
FIGS. 8A and 8B show specific knockdown of luciferase in KB cell xenografts after systemic injection based on bioluminescence imaging. Treatment: Folate receptor targeting 3WJ-exosomes encapsulating luciferase siRNA. Control: 3WJ-exosomes without folate, but with active siRNA (luciferase). Arrows indicate injection time points. (N=3); ***p<0.001.
Figure 9A:
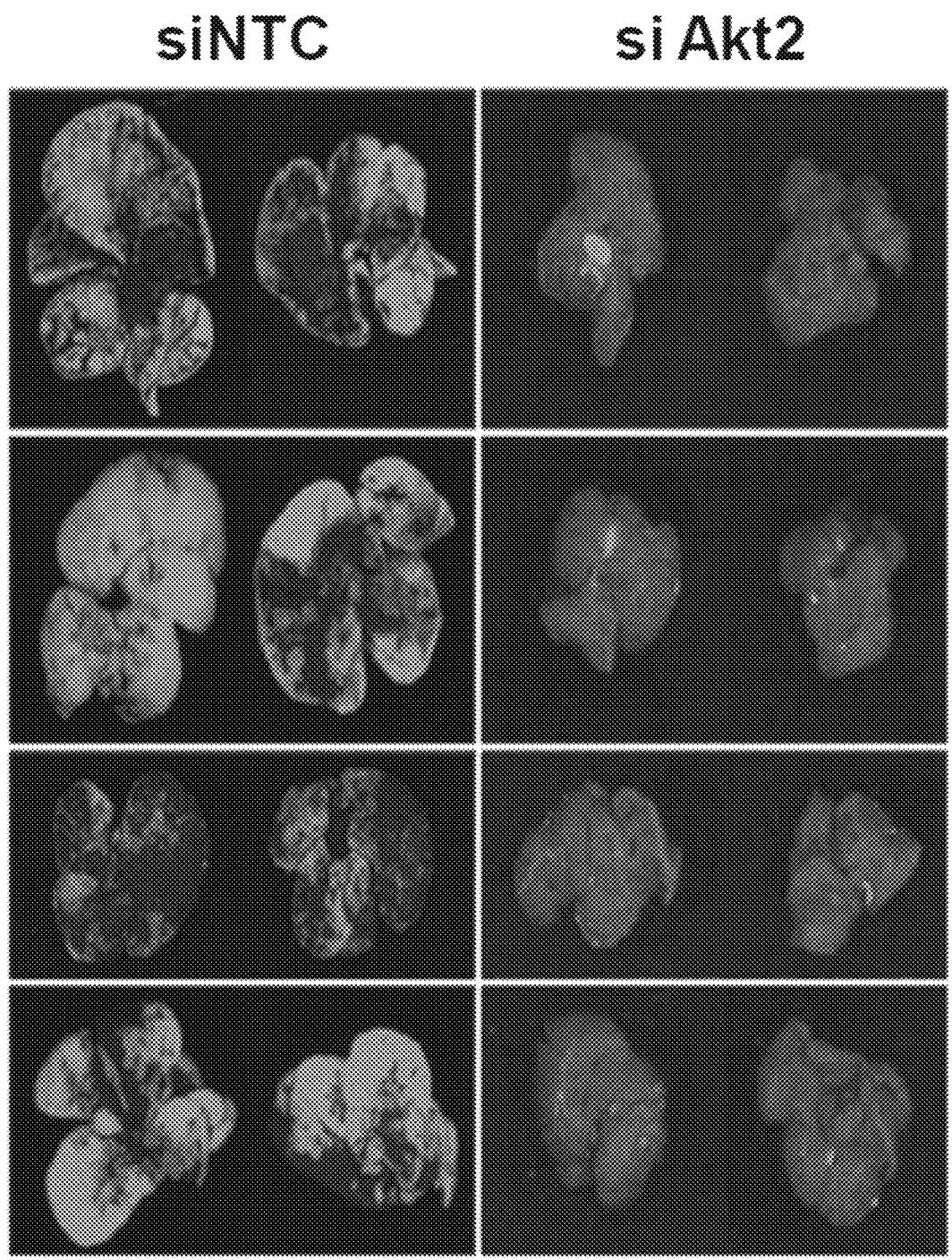
FIGS. 9A to 9C are images (FIG. 9A), qRT-PCR results (FIG. 9B), and Western blot results (FIG. 9C) showing suppression of Akt2 by siRNA inhibits the ability of colorectal cancer cells (injected intrasplenically) to establish liver metastases. NTC: Non-template Control.
Figures 9B, 9C:
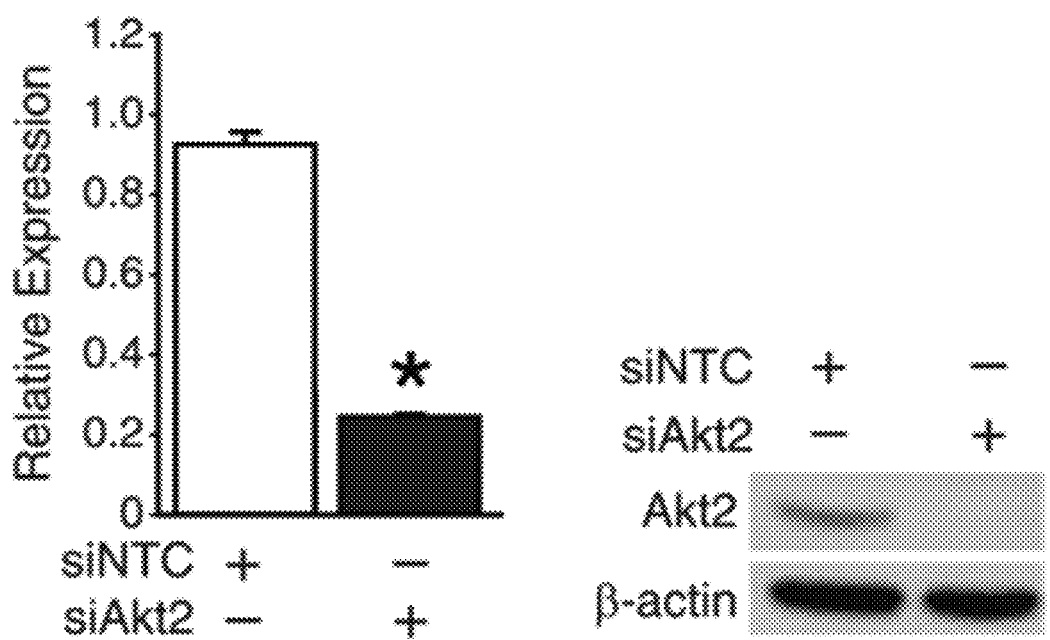
Figure 9D:
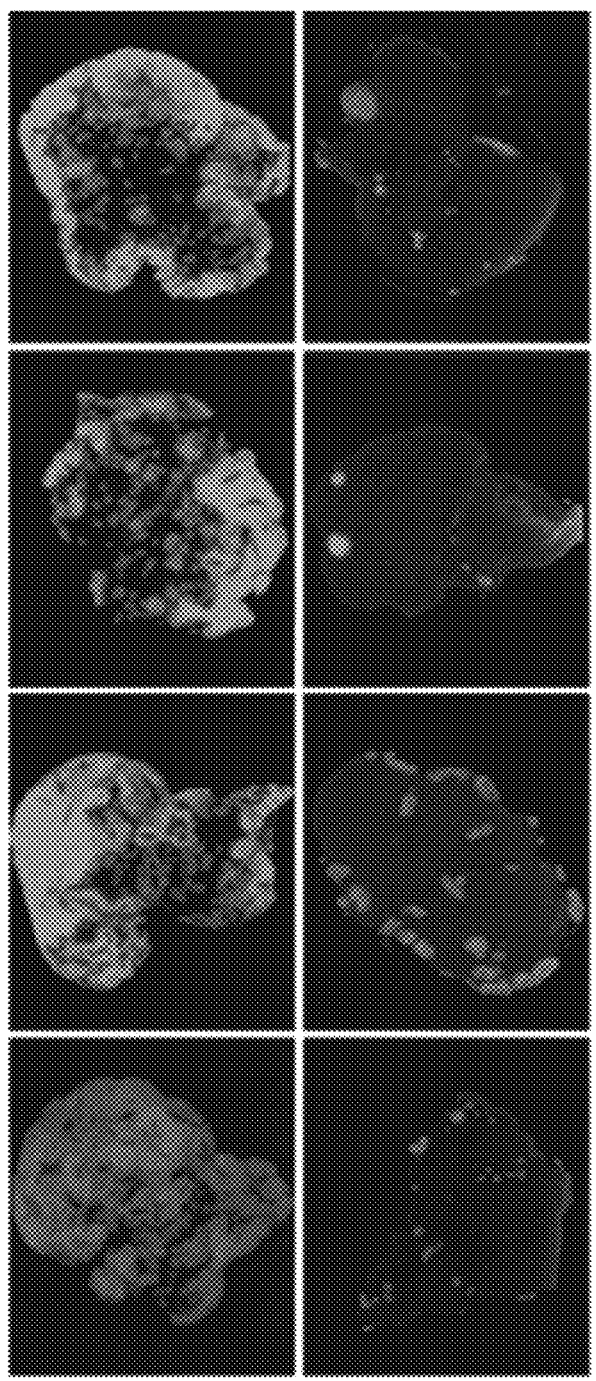
FIG. 9D shows suppression of metastatic tumor growth after systemic delivery of PI3K siRNA (imaged at day 35). Cancer cells express GFP. NTC: Non-template control.
Figure 11B:
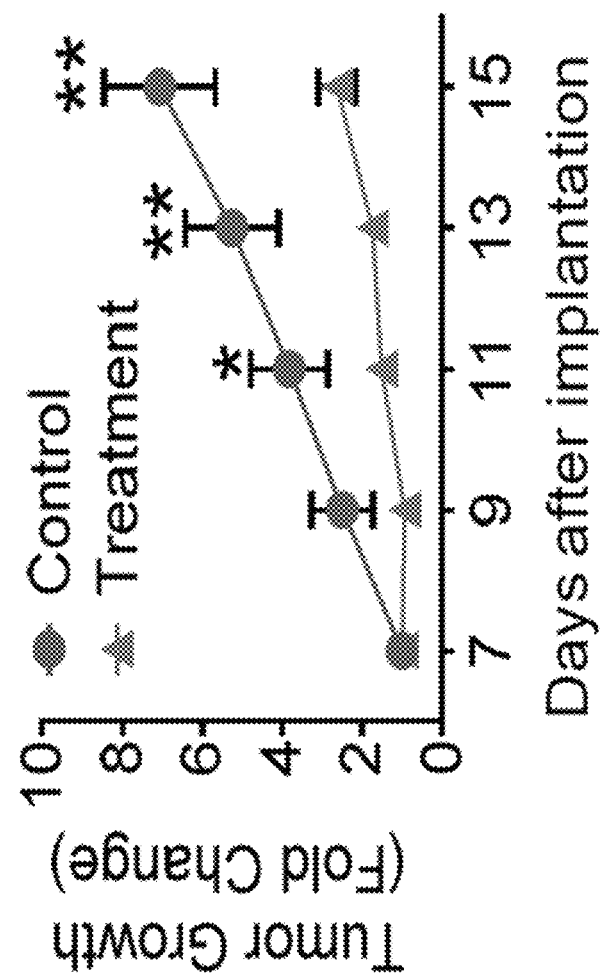
FIGS. 11A and 11B show inhibition of Triple Negative Breast tumor growth after systemic delivery of pRNA-3WJ-EGFR-antimiR-21 in orthotopic mouse model.
Figure 11A:
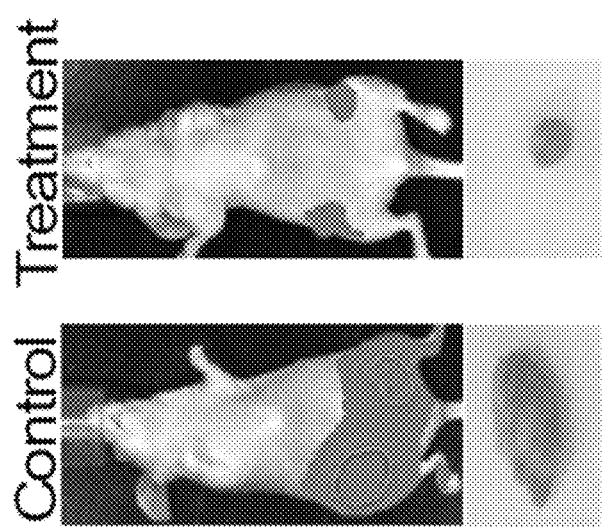
Figure 11C:
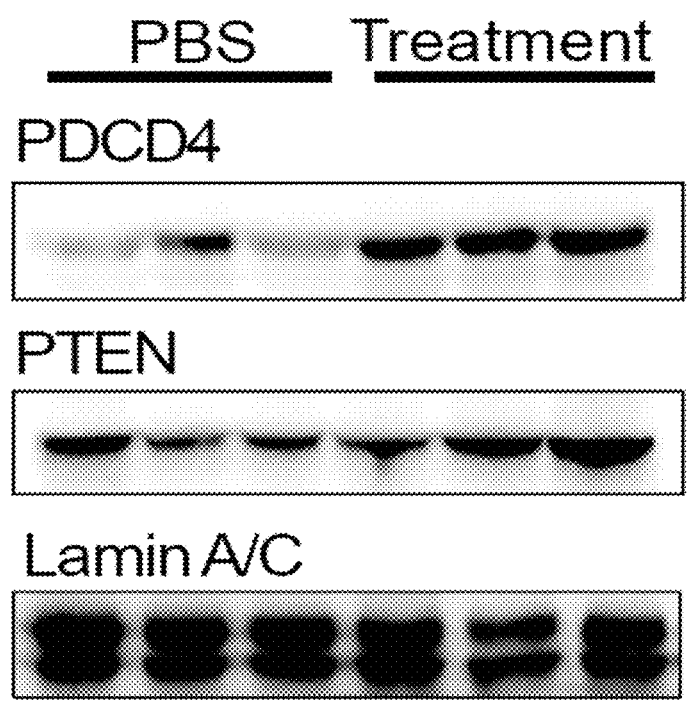
FIG. 11C is a Western blot showing the up-regulation of miR-21 target genes PTEN and PDCD4.
Figure 11D:
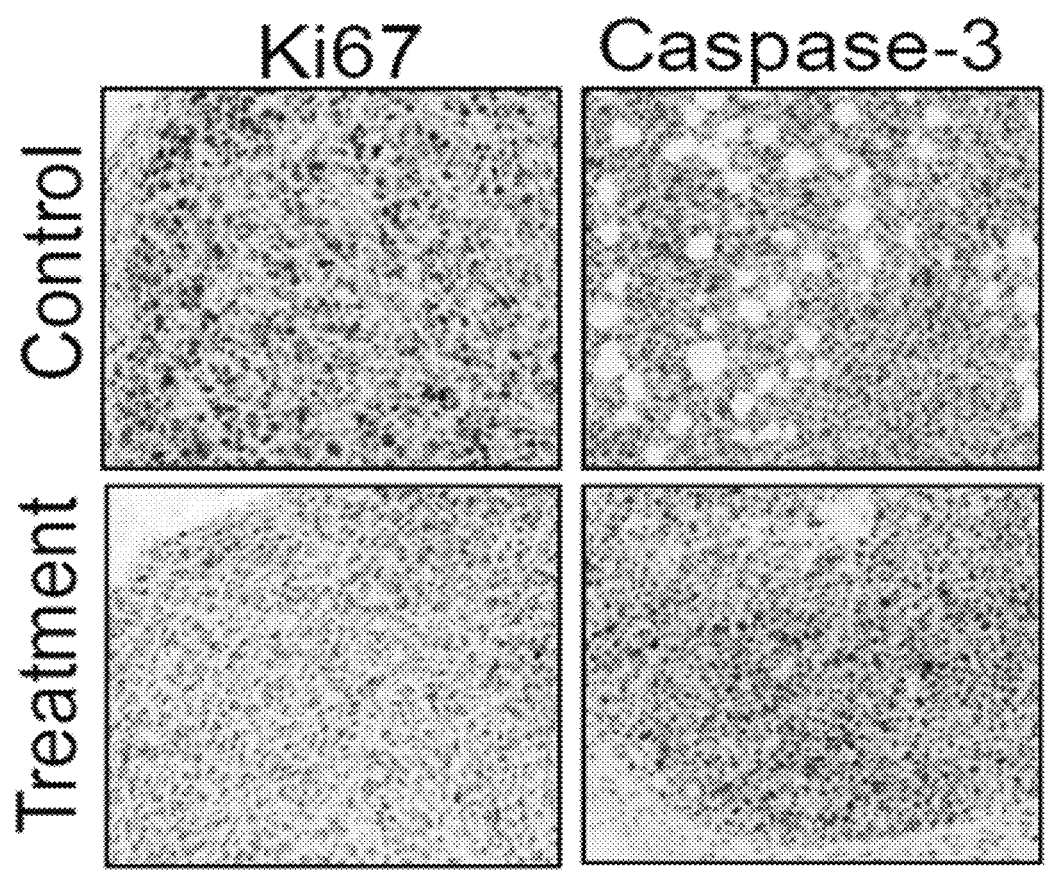
FIG. 11D shows results of an immunohistochemistry assay using Ki67 as indicator of tumor cell proliferation, and activated Caspase-3 as indicator of tumor cell apoptosis.

The Targeted Drug Delivery Efficiency of Exosomes Harboring Targeting Ligands as Vectors in Clinically Relevant Xenografts and Experimental Metastases Mouse Models Optimize Loading of RNAi Cargoes into Exosomes Typically, electroporation is used for loading siRNA/ miRNA into exosomes extracellularly. But, this transfer process can be inefficient, compromise the integrity of exosomes and generate RNA precipitates. A robust, yet gentle approach of loading exosomes using a unique combination of transfection reagents has been discovered in a cost-effective manner. Based on measurements of the encapsulated and free fluorescent siRNA cargoes after loading, the encapsulation efficiency of RNA into the purified exosome is calculated to be >95% (FIG. 8A). Importantly, the size, shape, surface properties and stability of exosomes remain nearly identical after RNAi encapsulation.

The Delivery and Endosome Escape of siRNA Using Luciferase siRNA for Validation

For functional assays, luciferase siRNA loaded exosomes were incubated with luciferase expressing KB cells (KB-Luc) without any transfection reagents. The knockdown efficiency was >80% in the presence of only 50 nM of siRNA loaded exosomes compared to scramble controls (FIG. 8B). For in vivo validation, KB-Luc cell xenografts were generated and systemically injected folate-3WJ-exosomes loaded with luciferase siRNA. Efficient knockdown of luciferase was observed based on reduced bioluminescence signal, which indicates that siRNA loaded folate-3WJ-exosomes are capable of endosomal escape and trigger gene silencing in vivo (FIG. 15). Intracellular trafficking studies were conducted by visualizing the co-localization of siRNA with Lysotracker Red (Invitrogen) that stains the endosomal/lysosomal compartments. A major factor for the failure or resistance in colorectal cancer treatment is due to the concurrent activation of both PI3K/Akt and RAS/RAF/MEK pathways. Dual inhibition of these two pathways using siRNAs can enhance the anti-proliferative effects, and is particularly effective for drug-resistant colorectal cancers. Suppression of Akt2 and KRAS in highly metastatic colorectal cells selectively inhibited their ability to metastasize and increased colorectal cell apoptosis (FIGS. 9A to 9D). Herein, the effect of exosomes displaying RNA aptamers binding to EpCAM (FIG. 10) and siRNAs to block PI3K and/or RAS pathways (single and combination treatment) are evaluated for their effectiveness and safety in inhibiting colorectal cancer progression and metastasis.

Targeted Delivery of miRNAs to Cancer Cells

MiRNAs play important roles in tumor progression, regulation of cell cycle, differentiation, metastasis, and apoptosis. The use of exosome displaying targeting ligands as vectors for delivery of anti-miRNA to inhibit colorectal or liver tumor growth by down-regulating oncogenic miRNAs, such as miR-21, a well-known player implicated in tumor progression and metastasis. EpCAM antigens overexpressed on cancer cell membranes are attractive for targeting, since they are overexpressed by >1000-fold in primary and metastatic colon and liver cancers, including cancer stem cells. A 2'F RNA aptamer with an unusually strong binding affinity to EpCAM through SELEX from a 2'-F 3WJ library based on RNA nanotechnology (FIG. 10) has been developed, which is displayed on exosome surface for targeting colorectal and liver tumors. A method of formulating RNA nanoparticle constructs for efficient delivery of anti-miRNA seed sequences has been developed as well. The Locked Nucleic Acid (LNA) modified 8 nucleotide sequence can bind with high affinity to the miRNA seed region and trigger miRNA inhibition. After incorporation of anti-miR-21 into pRNA-3WJ scaffold along with EGFR targeting RNA aptamers, the RNA nanoparticles can knockdown miR-21 expression and inhibit tumor proliferation and growth in Triple Negative Breast Cancer orthotopic xenografts after systemic injection (FIG. 11). Targeting of miR-21 resulted in direct up-regulation of tumor suppressor and pro-apoptotic genes including PTEN, PDCD4, RECK, and Bcl2 assayed by qRT-PCR and Western blot. Exosomes harboring EpCAM aptamer and anti-miR-21 cargo were evaluated for their ability to induce sustained tumor growth inhibition over time in colorectal and liver tumor models.

Alternative Anti-miRNA:

miR-221 expression is among the most upregulated miRNAs in the liver and colorectal tumors compared with healthy and adjacent benign liver. MiR-221 targets a number of key tumor suppressors including p27, p57, PTEN, TIMP3, and modulators of mTOR pathway.

Targeted Delivery of dsDNA for Gene Rescue

The vector plasmid coding for GFP proteins are loaded into exosomes, which are incubated with GFP negative cells without any transfection reagents. The GFP gene can also be loaded into exosome displaying RNA aptamers (in Table 1), which can then be tested in animal models with cancer xenografts expressing the receptor corresponding to the ligands on the exosome. Histological profile for expression of GFP in the xenograft tumor can be used to determine the feasibility of dsDNA delivery for gene rescue in vivo.

Targeted Delivery of CRISPR RNA Module for Genome Editing

The bacterial CRISPR-Cas (CRISPR: clustered regularly interspaced short palindromic repeats; Cas: CRISPR associated) loci encode several proteins to work together as an adaptive immune system similar to RNA interference against viral infections. This adaptable self-defense system is used by many bacteria to protect themselves from foreign nucleic acids, mediated by Cas nucleases and small RNA guides that specify target to the site for cleavage within the genome of the invader. In type II CRISPR-Cas systems, the RNA guided Cas9 nuclease can be reprogrammed to create double-stranded DNA breaks in the genomes of a variety of organisms, including human cells. The editing mechanism is exercised by homology-directed repair or non-homologous end joining mechanisms leading to nucleotide deletion, substitution or insertion. The most notable translational medicine for CRISPR/Cas9 system is the application of the modulated RNA-guided specific prokaryotic genomic editing process into eukaryotic cells as a promising genome editing therapy for adverse diseases including cancer, viral infection and several hereditary diseases. However, the delivery of the CRISPR components into eukaryotic cells for CRISPR-mediated genome editing therapy is very challenging due to the limited non-viral in vivo RNA delivery system. Herein, the special designed plasmid DNA or RNA cargoes including a specific gRNA and Cas9 mRNA are loaded into the exosome. Specific delivery of the CRISPR components to diseased cells are accomplished by displaying specific ligands (Table 1) on the exosome surface. The proof-of-concept is focused on by using cells or animal models to disrupt or repair reporter gene coding for genes, such as, β-gal, luciferase, or fluorescence proteins that are different from the marker fused to Cas9.

Clinically Relevant Xenograft and Metastases Mouse Models for Exosome Evaluations Xenograft Models:

Procedures have been established for generating subcutaneous colorectal cancer xenografts by injecting HT29 tumor cells directly into the flank, as well as more clinically relevant orthotopic models by injecting cells (or patient-derived cells) directly into the cecum of nude mice after surgical procedures. Alternatively, orthotopic liver cancer mouse models can be used. Orthotopic liver tumors are established by direct intrahepatic injection of luciferase expressing PLC/PRF/5 cells suspended in Matrigel into hepatic lobes.

Metastases Model:

Liver, lung and lymph node metastases are established by injecting HT29 cells expressing luciferase into the spleen or cecum wall and monitored by bioluminescence imaging. It has been demonstrated that after systemic injection, Alexa-647 labeled pRNA-3WJ nanoparticles can efficiently target HT29 xenografts, as well as liver, lung and lymph node metastatic cells. Little or no accumulation was observed in healthy vital organs and in normal liver/lung parenchyma.

The target gene expression of siRNAs and miRNAs are evaluated by qRT-PCR on mRNA levels and by Western blot at protein levels. The effects of RNA nanoparticles on cell growth and apoptosis can be assayed by WST-1, TUNEL, in situ caspase activity, DNA fragmentation, and Annexin V/PI staining. Finally, the PK/PD, ADME, and toxicity profiles of therapeutic exosomes can be explored.

Example 2: Nanoparticle Orientation to Control RNA Surface Display on Extracellular Vesicles for the Regression of Prostate, Breast and Colorectal Cancers In this example, RNA nanotechnology was used to reprogram natural extracellular vesicles for specific delivery of siRNA to cancer models in vitro and in vivo.

Materials and Methods

The construction, synthesis and purification of RNA nanoparticles with or without 2'-F modification or Alexa$_{647}$ labeling has been reported (Shu, D., et al. Nature Nanotechnology 6:658-667 (2011)).

The sequences of all RNA strands (lower case letters indicate 2'-F nucleotides) are:

```
a3WJ:
                                        (SEQ ID NO: 1)
5'-uuG ccA uGu GuA uGu GGG-3'.

b3WJ:
                                        (SEQ ID NO: 2)
5'-ccc AcA uAc uuu Guu GAu ccc-3'.

c3WJ:
                                        (SEQ ID NO: 3)
5'-GGA ucA Auc AuG GcA A-3'.

a3WJ-sph1:
                                        (SEQ ID NO: 4)
5'-uuG ccA uGu GuA uGu GGG AAu ccc GcG Gcc AuG Gcc
GGG AG-3'.

a3WJ-survivin sense:
                                        (SEQ ID NO: 5)
5'-uuG ccA uGu GuA uGu GGG GcA GGu uCC uuA ucu
Guc Auu-3'.

a3WJ-survivin sense(scramble):
                                        (SEQ ID NO: 6)
5'-uuG ccA uGu GuA uGu GGG AAu ccc GcG Gcc AuG Gcc
GGG AG-3'.

c3WJ-PSMA aptamer:
                                        (SEQ ID NO: 7)
5'-GGA ucA Auc AuG GcA AuG GGA ccG AAA AAG Acc
uGA cuu cuA uAc uAA Guc uAc Guu ccc-3'.

Survivin anti-sense:
                                        (SEQ ID NO: 8)
5'-UGA CAG AUA ACC AAC CUG C-3'.
```

-continued
```
Survivin anti-sense (scramble):
                                        (SEQ ID NO: 9)
5'-CUC CCG GCC AUG GCC GCG GGA UU-3'.

b3WJ-EGFR aptamer:
                                        (SEQ ID NO: 10)
5'-ccc AcA uAc uuu Guu GAu ccc Gcc uuA GuA AcG
uGc uuu GAu Guc GAu ucG AcA GGA GGc-3'.

a3WJ-Folate:
5'-(Folate) uuG ccA uGu GuA uGu GGG-3' (SEQ ID
NO: 1 for underlined portion).

a3WJ-Cholesterol:
5'-uuG ccA uGu GuA uGu GGG(Cholesterol TEG)-3'
(SEQ ID NO: 1 for underlined portion).

b3WJ-Folate:
5'-(Folate) ccc AcA uAc uuu Guu GAu ccc-3' (SEQ ID
NO: 2 for underlined portion).

b3WJ-Cholesterol:
5'-ccc AcA uAc uuu Guu GAu ccc(Cholesterol TEG)-
3' (SEQ ID NO: 2 for underlined portion).

b3WJ-Alexa647:
5'-(Alexa647)(AmC6)-ccc AcA uAc uuu Guu GAu ccc-
3' (SEQ ID NO: 2 for underlined portion).

c3WJ-Alexa647:
5'-GGA ucA Auc AuG GcA A(C6-NH)(Alexa647)-3' (SEQ
ID NO: 3 for underlined portion).

Folate-c3WJ-Alexa647:
5'-(Folate) GGA ucA Auc AuG GcA A(C6-
NH)(Alexa647)-3' (SEQ ID NO: 3 for underlined
portion).
```

EV Purification:

EVs were purified using a modified differential ultracentrifugation method (Thery, C., et al. Curr. Protoc. Cell Biol Chapter 3, Unit 3.22 (2006)). Briefly, the fetal bovine serum (FBS) used for cell culture was spun at 100,000×g for 70 min to remove the existing serum EVs. FBS is known to contain EVs and it has previously been reported that centrifugation may not remove all of the EVs, thus some EVs isolated from HEK293T cells may in fact contain EVs from FBS (Witwer, K. W., J Extracell. Vesicles. 2, (2013); Shelke, G. V., et al. J Extracell. Vesicles. 3, (2014)). The supernatant of HEK293T cell culture (EV-enriched medium) was harvested 48 hr after cell plating and spun at 300×g for 10 min to remove dead cells, followed by spinning at 10,000×g for 30 min at 4° C. to remove cell debris and/or microvesicles. EVs were concentrated from the culture medium by using an OptiPrep Cushion procedure (Jasinski, D., et al. Methods in Molecular Biology 1297:67-82 (2015)). The OptiPrep cushion offers an iso-osmotic pressure and prevents physical disruption of the EV. A 200 µL of 60% iodixanol (Sigma) was added to the bottom of each tube to form a cushion layer. After spinning at 100,000×g for 70 min at 4° C. using a Beckman SW28 rotor, the EVs migrated and concentrated to the interface layer between the 60% iodixanol and the EV-enriched medium. 1 mL of the fraction close to the interface and cushion was collected. A 6 mL EV solution was further washed and pelleted with a 30 mL PBS in a SW28 tube that contained 50 µL of 60% iodixanol cushion, then spun at 100,000×g for 70 min at 4° C. All the pellets in the cushion were collected and suspended in 1 mL of sterile PBS for further use.

Methods for cell culture, EM imaging, confocal microscopy, DLS measurement, and flow cytometry have been reported (varez-Erviti, L., et al. Nat Biotechnol. 29:341-345 (2011); Shu, D., et al. Nature Nanotechnology 6:658-667

(2011); Shu, D., et al. ACS Nano 9:9731-9740 (2015)). HEK293T, KB, LNCaP-FGC, and PC-3 cells were obtained from ATCC, and LNCaP-LN3 cells were obtained from the MD Anderson Cancer Center. Cell cultures purchased from ATCC were authenticated by Short Tandem Repeat (STR) prior to purchase, and LNCaP-LN3 cells were authenticated prior to receiving the cells as a gift. Each cell line was not tested for mycoplasma. While the KB cell line has been listed as a misidentified cell line that has been derived by contamination of HeLa cells, it serves as an ideal model in these studies. KB cells are known to overexpress folate receptors, allowing for proper specific targeting through the use of folate on RNA nanoparticles. The derivation of the KB cell line does not affect its use as a model to test the folate receptor-targeting property of RNA-displaying EVs.

NTA:

NTA was carried out using the Malvern NanoSight NS300 system on EVs re-suspended in PBS at a concentration of 10 µg of proteins/mL for analysis. The system focuses a laser beam through the sample suspension. EVs are visualized by light scattering, using a conventional optical microscope aligned to the beam axis which collects light scattered from every particle in the field of view. Three 10 sec videos record all events for further analysis by NTA software. The Brownian motion of each particle is tracked between frames, ultimately allowing for calculation of the size through application of the Stokes Einstein equation.

Size Exclusion Chromatography:

Sephadex G200 gel column was equilibrated with PBS and loaded with fluorescently-labeled EV samples. After washing with PBS, fractions were collected with 5 drops per well. The fluorescence intensity of $Alexa_{647}$ in the collected fractions was measured using a microplate reader (Synergy 4, Bio Tek Instruments, Inc).

siRNA Loading into EVs:

EVs (100 µg of total protein) and RNA (10 µg) were mixed in 100 µL of PBS with 10 µL of ExoFect Exosome transfection (System Biosciences) followed by a heat-shock protocol. Cholesterol-modified RNA nanoparticles were incubated with siRNA-loaded EVs at 37° C. for 45 min, then left on ice for 1 hr to prepare the RNA-decorated EVs. The decorated RNA nanoparticles were kept at a ratio of 10 µg RNA nanoparticles per 100 µg of EV in protein amount. To purify RNA-decorated EVs, 400 µL of RNA-decorated EVs were washed with a 5 mL PBS in a SW-55 tube that contained 20 µL of 60% iodixanol cushion and spun at 100,000×g for 70 min at 4° C. All the pellets in the cushion were collected and suspended in 400 µL of sterile PBS for further use.

Assay the siRNA Loading Efficiency into EVs:

siRNA nanoparticles to be loaded into EVs were labeled with $Alexa_{647}$ at the end of one strand. After loading siRNA as described above, the siRNA loaded EVs were precipitated down with ExoTC (System Biosciences), and the unloaded siRNA nanoparticles were collected from the supernatant. The concentration of free RNA nanoparticles and total input RNA nanoparticles were measured by $Alexa_{647}$ fluorescent intensity, using fluorometer with excitation at 635 nm, emission at 650-750 nm. The siRNA loading efficiency was calculated by the equation below:

$$SiRNA\ loading\ efficiency = \frac{Input\ RNA - Free\ RNA}{Input\ RNA}$$

FBS Digestion Experiment:

15 µL of the purified $Alexa_{647}$-RNA-decorated EVs were mixed with 30 µL of FBS (Sigma) and incubated at 37° C. for 2 hr. The samples were loaded into 1% syner gel for electrophoresis in TAE (40 mM Tris-acetate, 1 mM EDTA) buffer to test the degradation of decorated RNAs. Gel was imaged with Typhoon (GE Healthcare) using the Cy5 channel.

Assay the Effects of $PSMA_{apt}$/EV/siSurvivin on Prostate Cancer Using qRT-PCR:

LNCaP-FGC cells were incubated with 100 nM of $PSMA_{apt}$/EV/siSurvivin and controls including 3WJ/EV/siSurvivin and $PSMA_{apt}$/EV/siScramble nanoparticles respectively. After 48 hr treatment, cells were collected and target gene down-regulation effects were assessed by qRT-PCR. PC-3 cells were used as a negative control cell line.

Cells were processed for total RNA using Trizol RNA extraction reagent following manufacturer's instructions (Life Technologies). The first cDNA strand was synthesized on total RNA (1 µg) from cells with the various treatments of the RNAs using SuperScript™ III First-Strand Synthesis System (Invitrogen). Real-time PCR was performed using TaqMan Assay. All reactions were carried out in a final volume of 20 µL using TaqMan Fast Universal PCR Master Mix and assayed in triplicate. Primers/probes set for human BIRC5, 18S and GAPDH were purchased from Life Technologies. PCR was performed on Step-One Plus real time PCR system (Applied Biosystems). The relative survivin-mRNA expression level was normalized with 18S RNA for in vitro assays and GAPDH for in vivo assays as an internal control. The data was analyzed by the comparative CT Method (ΔΔCT Method).

Due to the high reproducibility and consistency between cell cultures, it was predetermined that in the in vitro studies a sample size of at least n=3 would allow for adequate analysis to reach meaningful conclusions of the data. However, in in vivo studies, higher variances are seen in tissue samples; therefore, a higher set of samples is required to compensate for this natural variance. In these studies n=4 for the $PSMA_{apt}$/EV/siScramble tumors, while n=2 for $PSMA_{apt}$/EV/siSurvivin tumors due to limited tumor samples and the experiment repeated in triplicate was completed. N=3 for tumors from all three groups in breast cancer mice study. Samples and animals were randomized into groups throughout the whole experiment.

Western Blot and Antibodies:

LNCaP-FGC cells were incubated with 100 nM of the $PSMA_{apt}$/EV/siSurvivin and controls including 3WJ/EV/siSurvivin and $PSMA_{apt}$/EV/siScramble nanoparticles respectively. After 48 hr treatment, cells were collected and lysed with RIPA buffer (Sigma) with a protease inhibitor cocktail (Roche). Primary antibodies used for western blot analysis were rabbit anti-human survivin antibody (R&D system, AF886), rabbit anti-human β-actin (Abcam, ab198991), rabbit anti-human TSG101 (Thermo Scientific, PA5-31260), rabbit anti-human integrin α4 (Cell Signaling, 4711S), rabbit anti-human integrin α6 (Cell Signaling, 3750S), rabbit anti-human integrin β1 (Cell Signaling, 4706S), rabbit anti-human integrin β4 (Cell Signaling, 4707S), rabbit anti-human integrin β5 (Cell Signaling, 4708S), rabbit anti-human Glypican 1 (Thermo Fisher, PA5-28055), GAPDH antibody (Santa Cruz Biotechnology).

Cytotoxicity Assay:

The cytotoxicity of $PSMA_{apt}$/EV/siSurvivin was evaluated with an MTT assay kit (Promega) according to the manufacturer's protocol. LNCaP-FGC and PC-3 cells were treated with EVs in triplicate in a 96-well plate. After 48 hr, cell survival rate was analyzed by MTT assay on a microplate reader (Synergy 4, Bio Tek Instruments, Inc).

In vivo targeting assay of tumor xenograft after systemic injection of EVs: To generate KB cell xenograft mice model, male athymic nude Nu/Nu (6-8 weeks old) mice (Taconic) were used. $2\times10^6$ KB cells in 100 µL of PBS were injected to each mouse subcutaneously. When the tumor reached a volume of ~500 mm$^3$, the mice were anesthetized using isoflurane gas (2% in oxygen at 0.6 L/min flow rate) and injected intravenously through the tail vein with a single dose 2 mg/kg of EVs/mice weight. The mice were euthanized after 8 hr, and organs and tumors were taken out for fluorescence imaging to compare the biodistribution profiles of EVs using IVIS Spectrum Station (Caliper Life Sciences). This animal experiment was done with a protocol approved by the Institutional Animal Care and Use Committee (IACUC) of University of Kentucky.

Three mice per group bearing MDA-MB-468 orthotopic xenograft tumor with size of approximately 200 mm$^3$ were injected once with 4 µM of EVs in 100 µL volume via tail vein. After 8 hr of the systemic administration, mice were sacrificed by cervical dislocation under anesthesia and mammary tumors were dissected out immediately. Fluorescence signals of Alexa$_{647}$ from the EVs were detected by examining the dissected tumors using the IVIS Lumina Series III Pre-clinical In Vivo Imaging System (Perkin Elmer) with an excitation at 640 nm and emission at 660 nm for a 1 min exposure. The fluorescence intensity was expressed as the Mean Radiant Efficiency [p/s/cm$^2$/sr]/[µW/cm$^2$]. PBS injected mice were used as negative control for background fluorescence. This animal experiment was done with a protocol approved by the Institutional Animal Care and Use Committee (IACUC) of The Ohio State University.

In vivo therapeutic effect of EVs in prostate cancer mouse models: 6-8 week-old male nude mice (Nu/Nu) were purchased from Charles River (Wilmington, Mass.). The mice were maintained in sterile conditions using IVC System (Innovive). Tumor xenografts were established by subcutaneous injection of $2\times10^6$ cancer cells mixed with equal volume of Matrigel matrix (Corning Life Sciences) in the flank area of the mice. PSMA$_{apt}$/EV/siSurvivin, PSMA$_{apt}$/EV/siScramble and PBS were administered by tail vein injection at a dosage of 0.5 mg siRNA/5 mg EVs per kg of mice body weight twice per week for three weeks. Two axes of the tumor (L, longest axis; W, shortest axis) were measured with a caliper. Tumor volume was calculated as: $V=(L\times W^2)/2$. This animal experiment was done with a protocol approved by the Institutional Animal Care and Use Committee (IACUC) of North Dakota State University. For tumor inhibition assay, n=10, the mice that did not develop tumors from the beginning were excluded from analysis.

In vivo therapeutic effect of EVs in breast cancer mouse models: The 4-week-old female athymic nu/nu outbred mice were acquired from the athymic nude mouse colony maintained by the Target Validation Shared Resource at the Ohio State University; the original breeders (strain #553 and #554) for the colony were received from the NCI Frederick facility and were used for all studies. Orthotopic mammary fat pad xenograft tumor was generated in the mice by injection of $2\times10^6$ of MDA-MB-468 cells, previously maintained in DMEM/10% FBS/1% Penicillin and Streptomycin. Five mice per group with tumor formed at mammary gland with a size of approximately 100 mm$^3$ were injected with 0.5 mg siRNA/5 mg EVs per kg of mice body weight via tail vein. PBS and EGFR$_{apt}$/EV/siScramble were used as negative control groups. Total of five doses were injected into mice once a week. Each time of injection, tumor volumes were determined by $V=(L\times W^2)/2$ (mm$^3$). This animal experiment was done with a protocol approved by the Institutional Animal Care and Use Committee (IACUC) of The Ohio State University.

Patient Tumor Engraftment into SCID Mice:

Male NOD-scid IL2Rgamma$^{null}$ mice were purchased from the Jackson Laboratory (Bar Harbor, Me.). Housing for these animals was maintained in a HEPA-filtrated environment within sterilized cages with 12 h light/12 h dark cycles. All animal procedures were conducted with approval of and in compliance with University of Kentucky Institutional Animal Care and Use Committee. The original patient CRC tumor (F0 generation) was divided and implanted into the flanks of a NOD scid gamma mouse (The Jackson Laboratory; 005557). When the resulting tumors grew to 1 cm$^3$, each tumor (F1 generation) was resected, divided into 2-mm$^3$ pieces and implanted into mice for experimental procedure (F2 generation). Patient tumor engraft mice were injected with 0.5 mg siRNA/5 mg EVs per kg of mice body weight via tail vein. FA/EV/siScramble was used as negative control group. Total of five doses were injected into mice once a week. Each time of injection, tumor volumes were determined by $V=(L\times W^2)/2$ (mm$^3$).

Statistics:

Each experiment was repeated at least 3 times with triplication for each sample tested. The results were presented as mean±standard deviation, unless otherwise indicated. Statistical differences were evaluated using unpaired t test with GraphPad software, and p<0.05 was considered significant.

Results

1. Design and Construction of Arrow-Shaped RNA Nanostructures for Display on EV Surface.

Figure 12A:
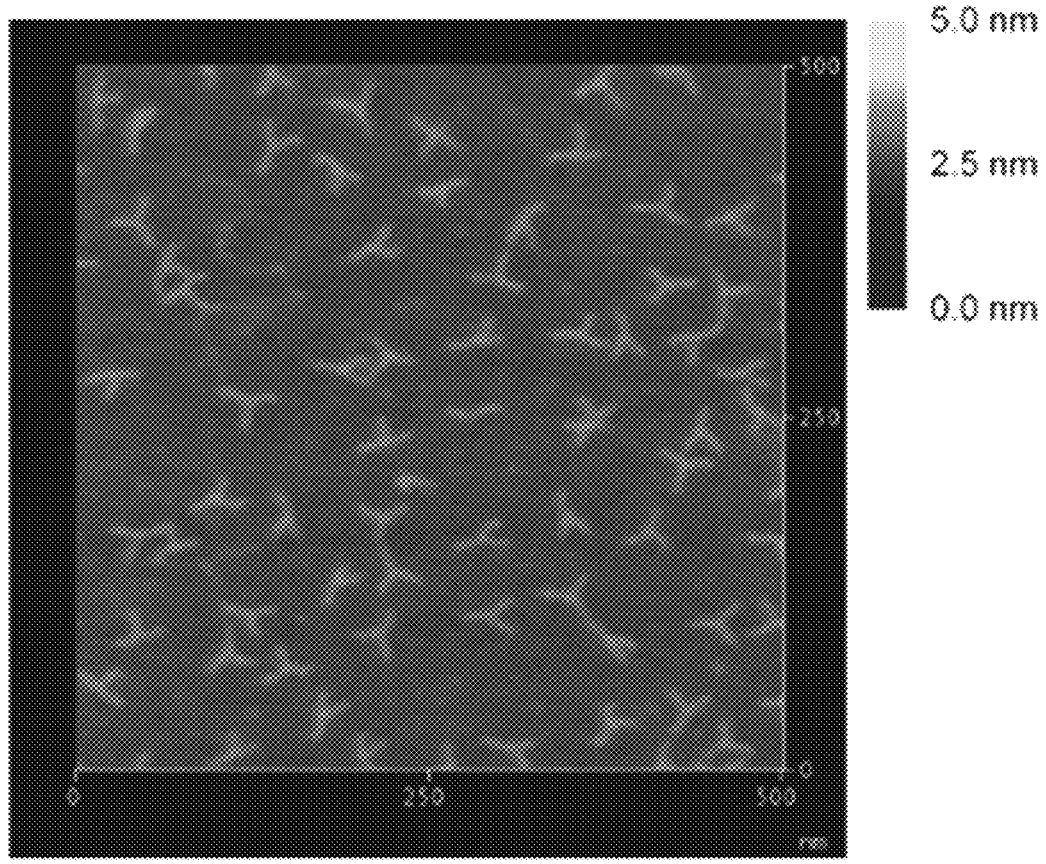
Figure 12B:
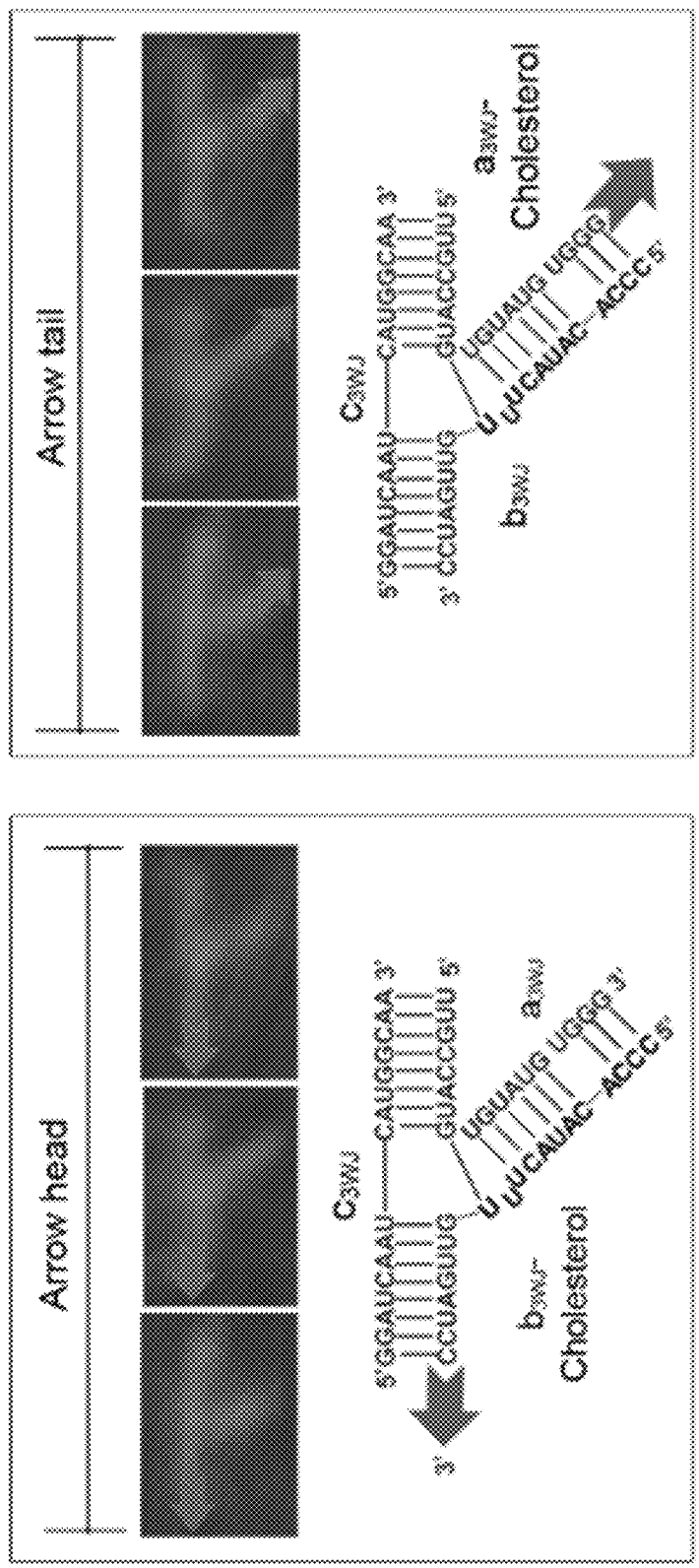
Figure 12D:
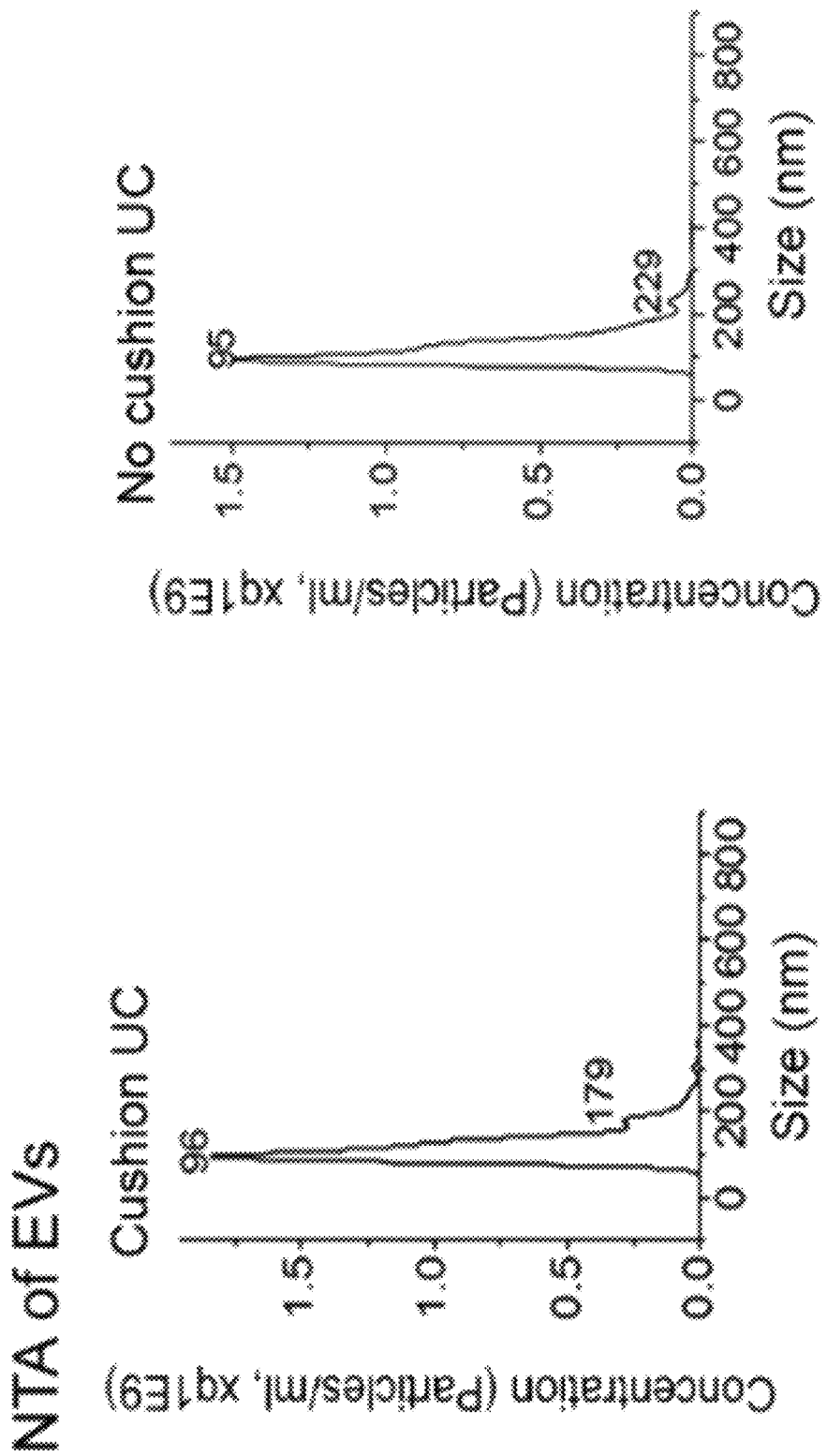
Figure 12E:
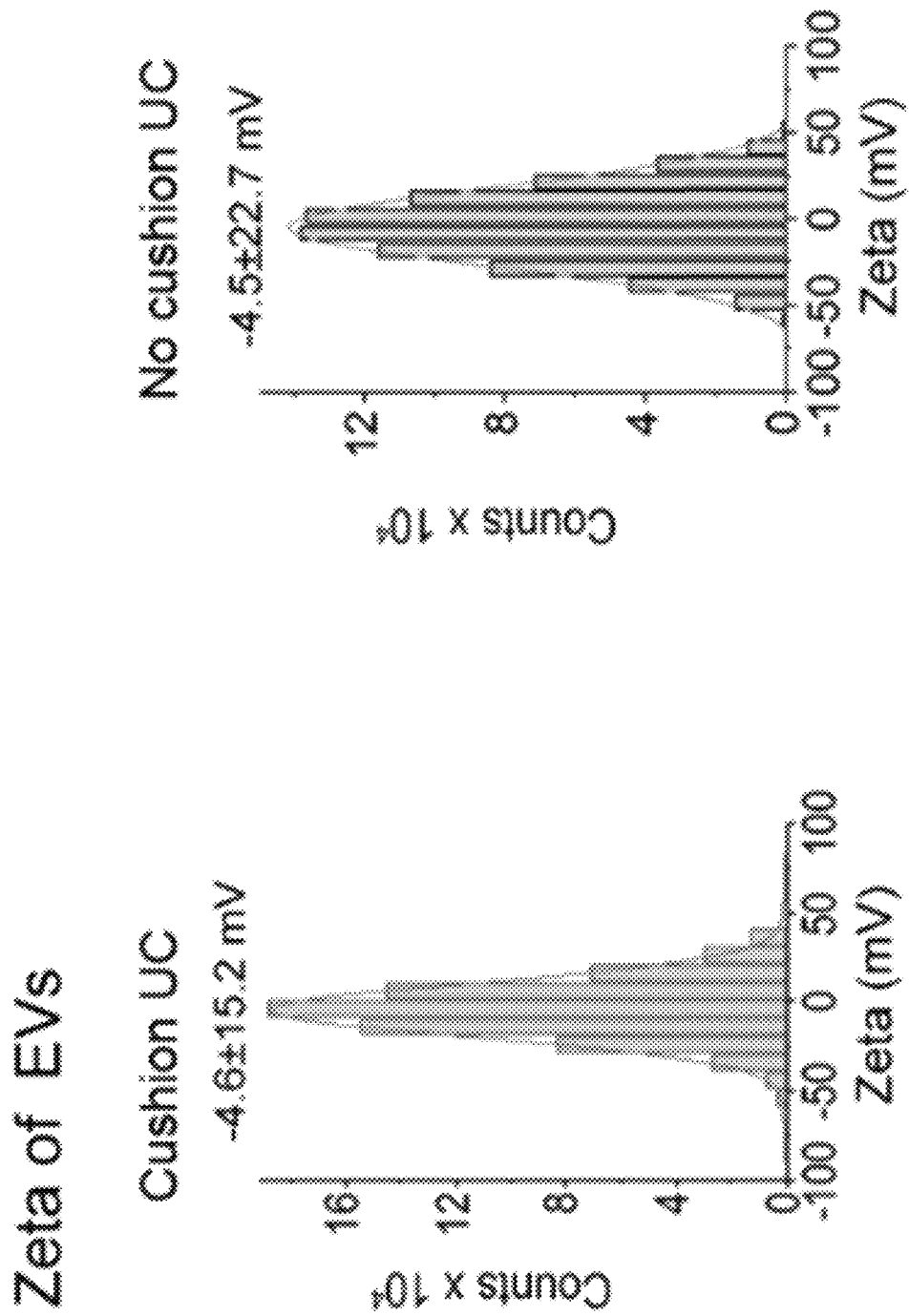

The three-way junction (3WJ) (Shu, D., et al. Nature Nanotechnology 6:658-667 (2011); Zhang, H., et al. RNA 19:1226-1237 (2013)) of the bacteriophage phi29 motor pRNA folds by its intrinsic nature into a planner arrangement with three angles of 60°, 120°, and 180° between helical regions (FIG. 12a-12b) (Zhang, H., et al. RNA 19:1226-1237 (2013)). The pRNA-3WJ was extended into an arrow-shaped structure by incorporating an RNA aptamer serving as a targeting ligand for binding to specific receptors overexpressed on cancer cells. The engineered pRNA-3WJ was used to decorate EVs purified from HEK293T cell culture supernatants to create ligand-decorated EVs. HEK293T EVs were used as they contain minimal intrinsic biological cargos compared to EVs generated by other cells (Lamichhane, T. N., et al. Mol. Pharm. 12:3650-3657 (2015)). As shown in Western blots (FIG. 18a), HEK293T isolated EVs showed negative staining for several common integrin markers as seen on EVs for cancerous origins (Rak, J. Nature 527:312-314 (2015); Melo, S. A. et al. Nature 523:177-182 (2015)), with only positive staining for TSG101. Additional steps were taken to remove EVs from FBS used in the HEK293T cell culture; although, centrifugation might not completely remove the FBS EVs (Witwer, K. W., J Extracell. Vesicles. 2, (2013); Shelke, G. V., et al. J Extracell. Vesicles. 3, (2014)). An OptiPrep ultracentrifugation method was used to purify EVs (Thery, C., et al. Curr. Protoc. Cell Biol Chapter 3, Unit 3.22 (2006)). Adding the iso-osmotic OptiPrep cushion layer for ultracentrifugation greatly enhanced reproducibility of EVs purification in purity (FIG. 18c), and also minimized physical disruption of EVs by ultracentrifugation pelleting as shown by Electron Microscopy (EM) imaging (FIG. 12c). The presence of the OptiPrep cushion layer did not change the EVs particle size distribution or zeta potential significantly (FIG. 12d-e), but rather preserved the native shape of EVs. The EVs purified without the OptiPrep cushion appear as flattened spheres (FIG. 12c right), while the majority of EVs purified with the cushion appear as full spheres (FIG. 12c left). Thus the size of EVs from EM image might not always represent its particle size distribution in the population. Nanoparticle Tracking Analysis (NTA) and Dynamic Light Scattering (DLS) revealed that the isolated native EVs were physically homogeneous, with a narrow size distribution centered around 96 nm (FIG. 12d) and a negative zeta potential (FIG. 12e).

Figure 18A:
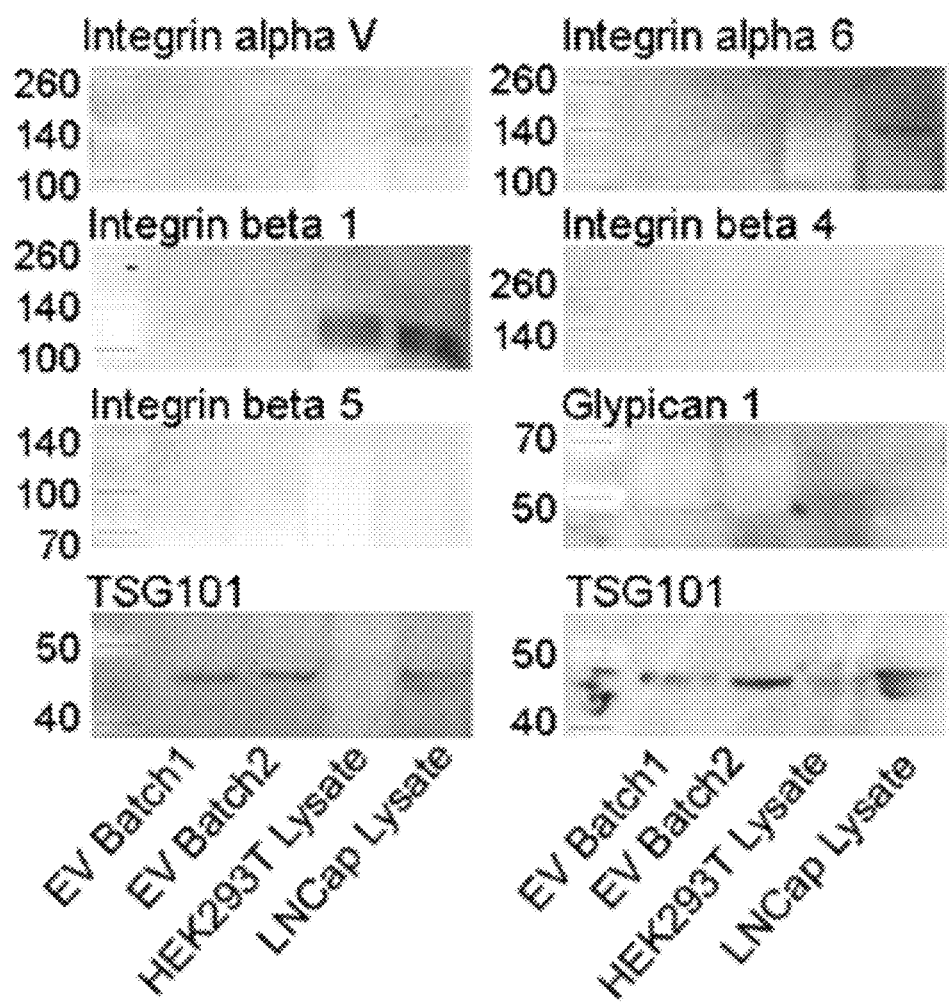

The purified EVs were further identified by the presence of EV specific marker TSG101 (Kumar, D., et al. Oncotarget 6:3280-3291 (2015)) by Western Blot (FIG. 18a). The yield of purified EVs from HEK293T cell culture supernatant was about 10-15 µg (measured as protein concentration), or $0.1$-$1.9 \times 10^9$ EV particles (measured by NTA) per $10^6$ cells. A single steroid molecule, cholesterol-tetraethylene glycol (TEG), was conjugated into the arrow-tail of the pRNA-3WJ to promote the anchoring of the 3WJ onto the EV membrane (FIG. 12b). Cholesterol spontaneously inserts into the membrane of EVs via its hydrophobic moiety (Bunge, A., et al. J Phys Chem. B 113:16425-16434 (2009); Pfeiffer, I., et al. J Am. Chem. Soc 126:10224-10225 (2004)). Displaying of RNA nanoparticles on surface of purified EVs was achieved by simply incubating the cholesterol-modified RNA nanoparticles with EVs at 37° C. for one hour.

Figures 12F, 12G:
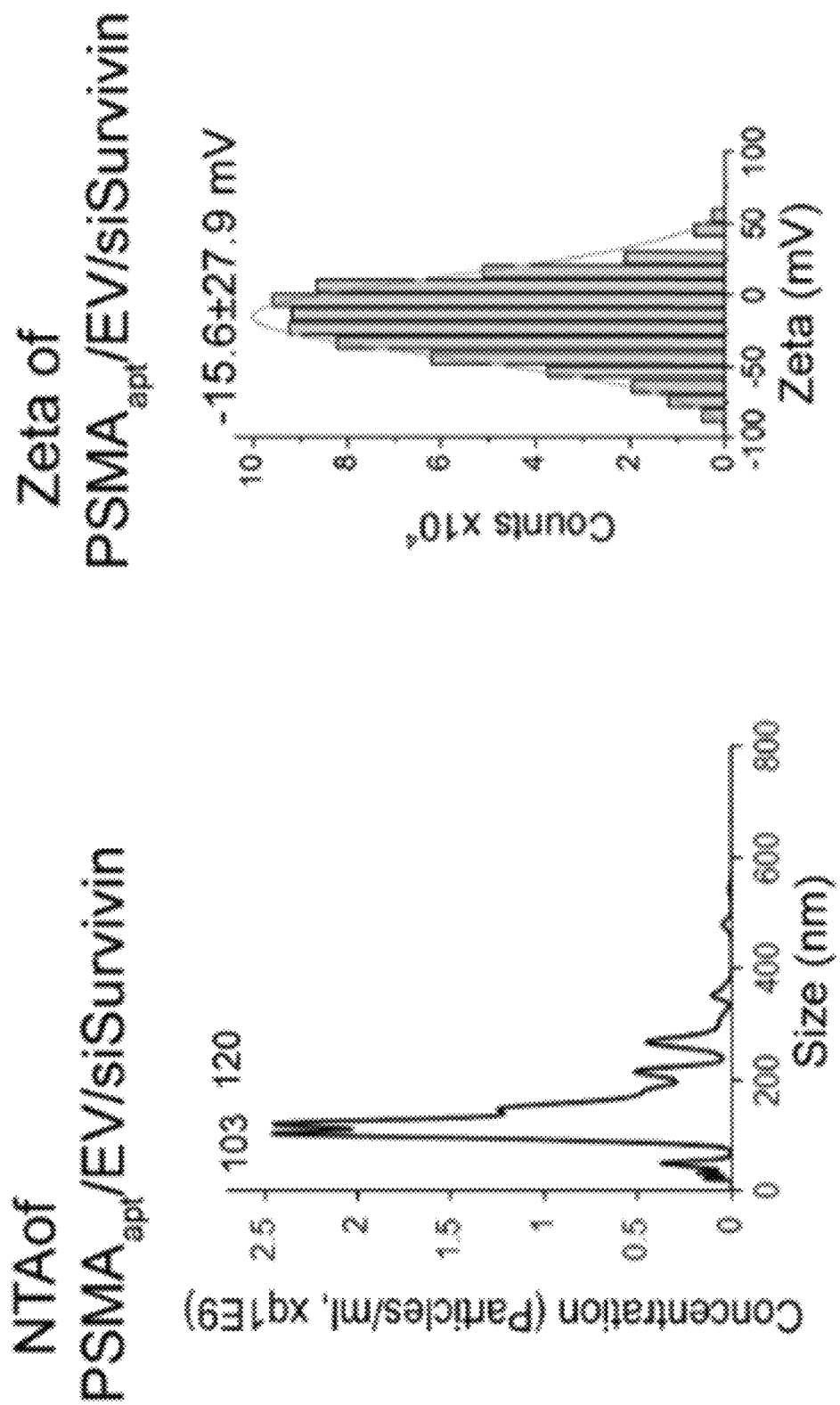
Figure 12H:
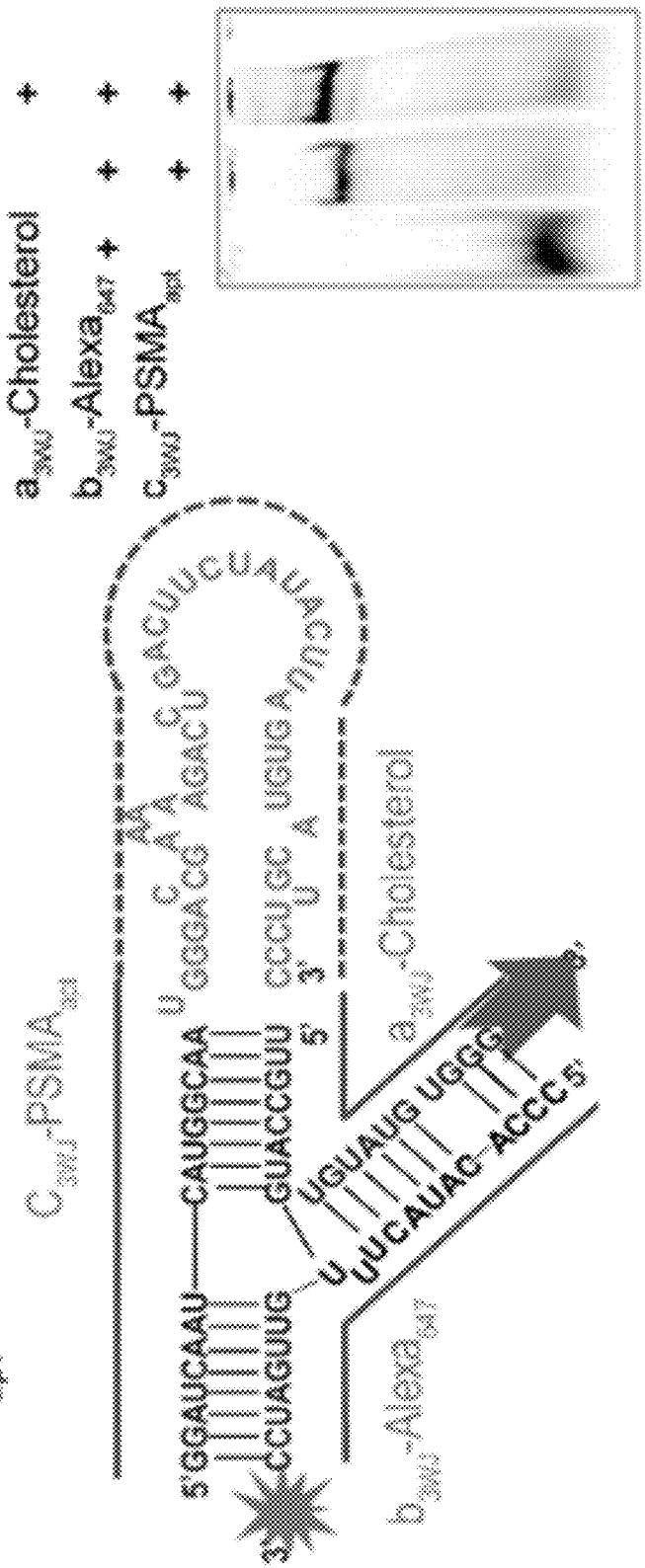

EVs hold great promise as emerging therapeutic carriers given their role in intercellular communication. They can enter cells through multiple routes including membrane fusion, tetraspanin and integrin receptor-mediated endocytosis, lipid raft mediated endocytosis, or micropinocytosis; but there is limited specificity regarding the recipient cells (Marcus, M. E., et al. Pharmaceuticals. (Basel) 6:659-680 (2013); van Dongen, H. M., et al. Microbiol. Mol. Biol. Rev. 80:369-386 (2016)). In order to confer specific targeting of EVs to cancer cells, three classes of targeting ligands, folate, PSMA RNA aptamer, or EGFR RNA aptamer was conjugated to the 3WJ for displaying on the EVs surface. Folate is an attractive targeting ligand since many cancers of epithelial origin, such as colorectal cancers, overexpress folate receptors (Parker, N., et al. Anal. Biochem. 338:284-293 (2005)). PSMA is expressed at an abnormally high level in prostate cancer cells, and its expression is also associated with more aggressive disease (Dassie, J. P., et al. Mol Ther. 22:1910-1922 (2014)). A PSMA-binding 2'-Fluoro (2'-F) modified RNA aptamer A9g (Rockey, W. M., et al. Nucleic Acid Ther. 21:299-314 (2011); Binzel, D., et al. Molecular Therapy 24, 1267-1277 (2016)) was displayed on EVs to enhance targeting efficiency to prostate cancer cells. The PSMA aptamer A9g is a 43-mer truncated version of A9, which binds PSMA specifically with $K_d$ 130 nM (Rockey, W. M., et al. Nucleic Acid Ther. 21:299-314 (2011)) and used as RNA based ligand. EGFR is highly overexpressed in triple negative breast cancer (TNBC) tumors and metastatic TNBC tumors (Hynes N. E., et al. Nat Rev. Cancer 5, 341-354 (2005)). An EGFR specific 2'F-RNA aptamer (Esposito, C. L., et al. PLoS ONE 6, e24071 (2011); Shu, D., et al. ACS Nano 9, 9731-9740 (2015)) was incorporated to one end of pRNA-3WJ and thereby displayed on EVs for enhanced targeting of breast cancer cells. For imaging, one of the pRNA-3WJ strands was end-labeled with a fluorescent dye $Alexa_{647}$ (FIG. 12h). The size distribution and zeta potential of RNA nanoparticle-decorated EVs did not change significantly compared with native EVs as measured by NTA and DLS (FIG. 12f-g).

Figure 12I:
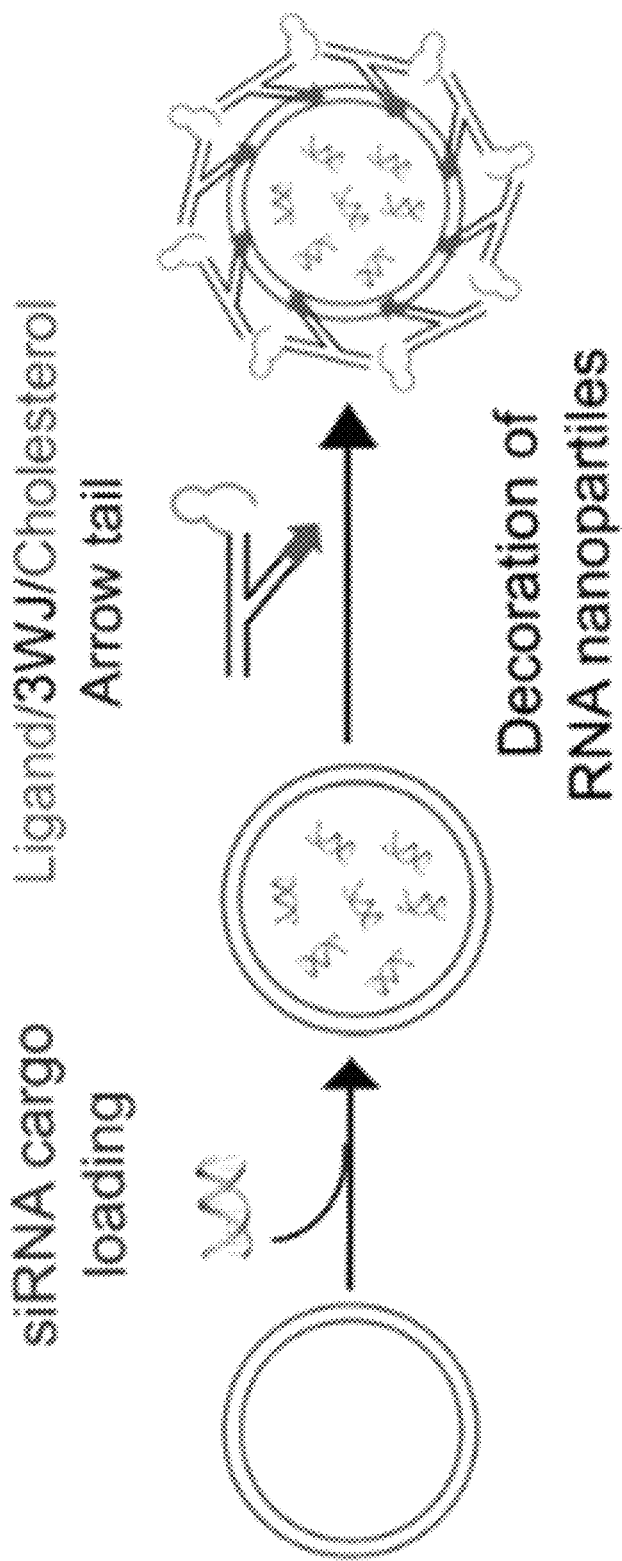
Figure 18B:
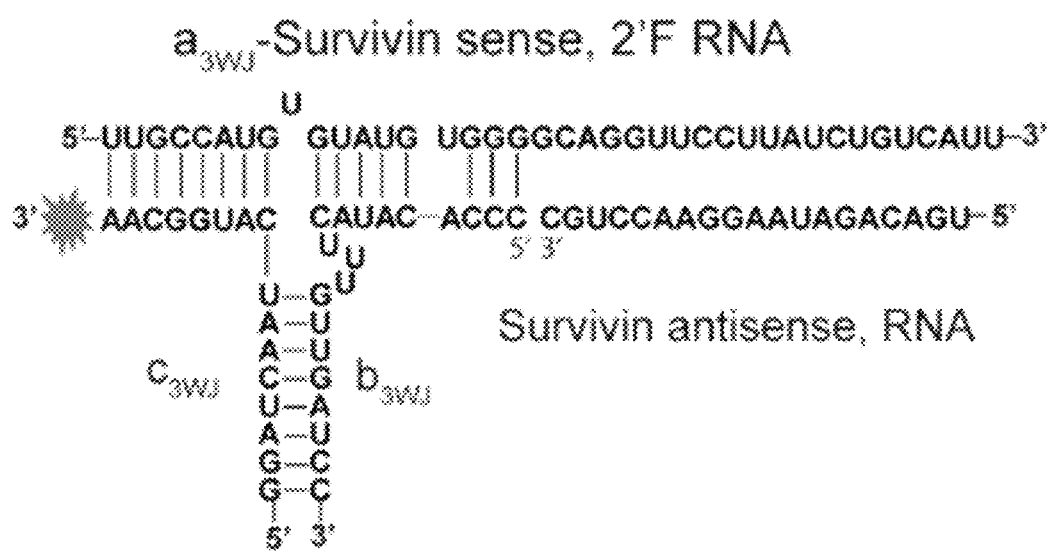
Figure 18D:
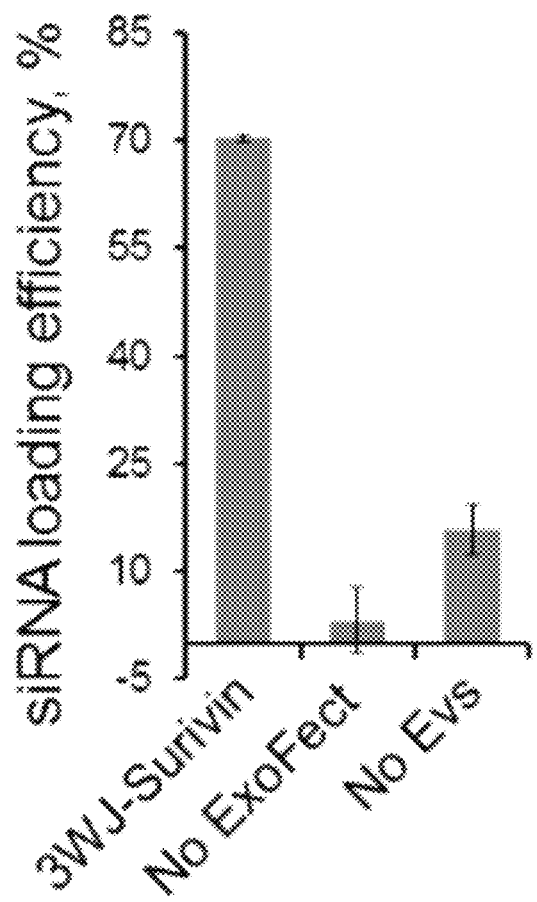
Figure 18E:
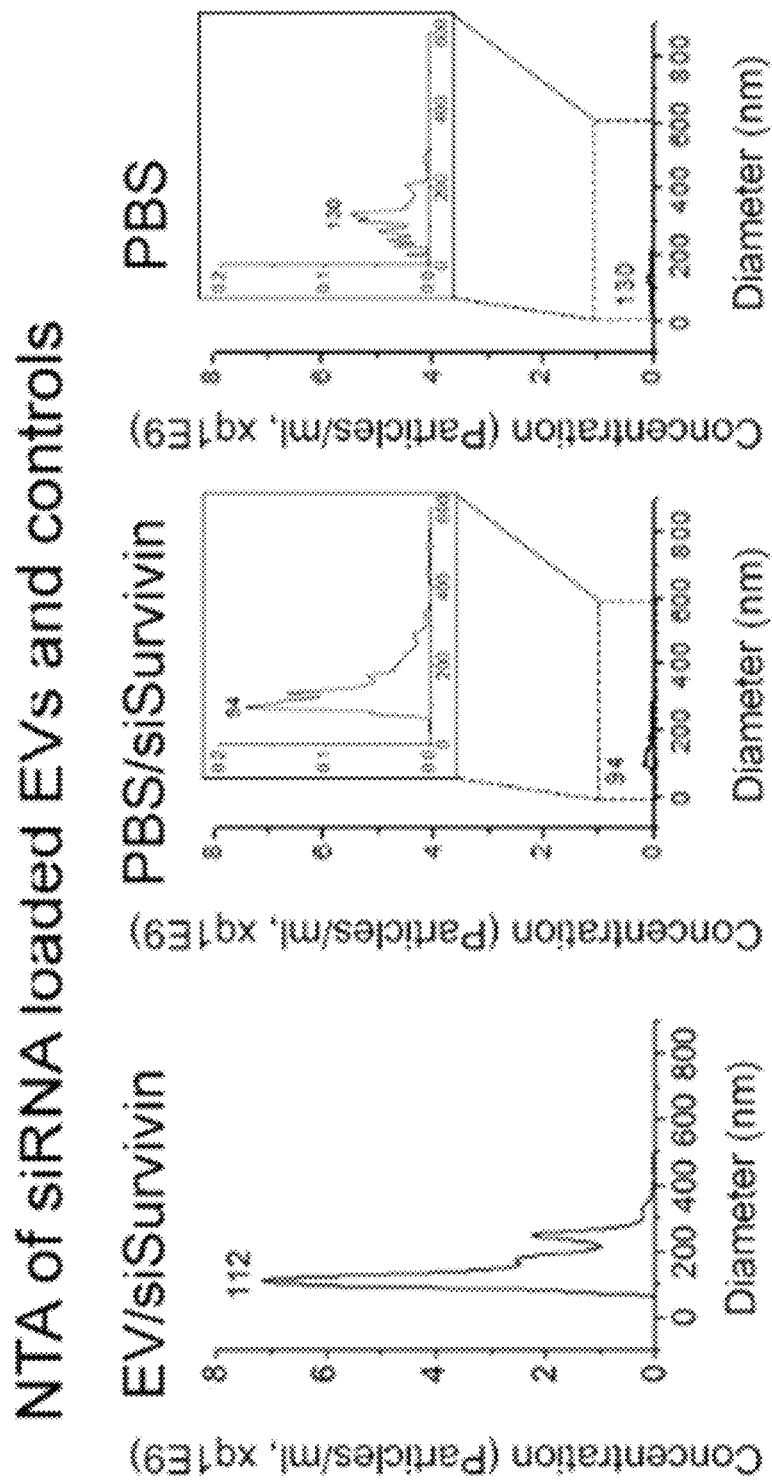

Survivin, an inhibitor of cell apoptosis, is an attractive target for cancer therapy, since its knockdown can decrease tumorigenicity and inhibit metastases (Paduano, F., et al. Molecular Cancer Therapeutics 5, 179-186 (2006); Khaled, A., et al. Nano Letters 5, 1797-1808 (2005)). In combination with the survivin siRNA loaded in the EVs (FIG. 12i), siRNA loaded EVs with targeting moieties were prepared to evaluate in vivo prostate, breast, and colon cancer inhibition efficacy. To improve the stability of siRNA in vivo, the passenger strand was 2'-F modified on pyrimidines to provide RNase resistance, while the guide strand was kept unmodified (Cui, D. et al. Scientific reports 5, 10726 (2015); Lee, T. J. et al. Oncotarget 6, 14766-14776 (2015)). For tracking siRNA loading efficiency in EVs, the survivin siRNA was fused to an $Alexa_{647}$-labeled 3WJ core and assembled into RNA nanoparticles (FIG. 18b). After loading siRNA into EVs and decorating EVs with $PSMA_{apt}$/3WJ/Cholesterol RNA nanoparticles, the size of EVs did not change significantly as measured by NTA with two peaks at 103 and 120 nm (FIG. 12f). Treating survivin-3WJ RNA nanoparticles in PBS with ExoFect but without EVs, showed a different particle size distribution profile (PBS/siSurvivin) and about 40-times lower particle concentration (FIG. 18e). The loading efficiency for siRNA-3WJ RNA nanoparticles was around 70% (FIG. 18d) as measured by fluorescent intensity of the free RNA nanoparticles. Controls without EVs or with only the ExoFect reagent showed as low as 15% pelleting.

2. Arrow-Head or Arrow-Tail Cholesterol Labeling of RNA Nanoparticles Results in EV Loading or Membrane Display, Respectively.

2.1. Differentiation Between Entry or Surface Display on EVs Using Serum Digestion Assay.

Figure 13C:
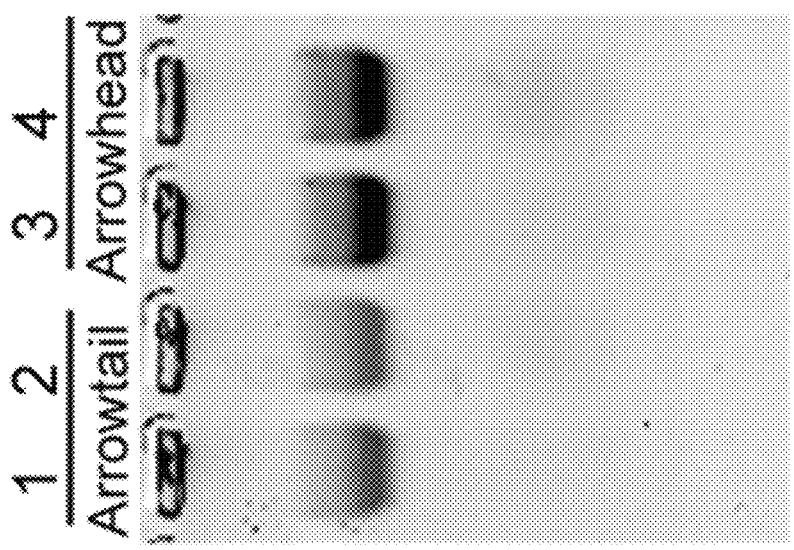
Figure 13D:
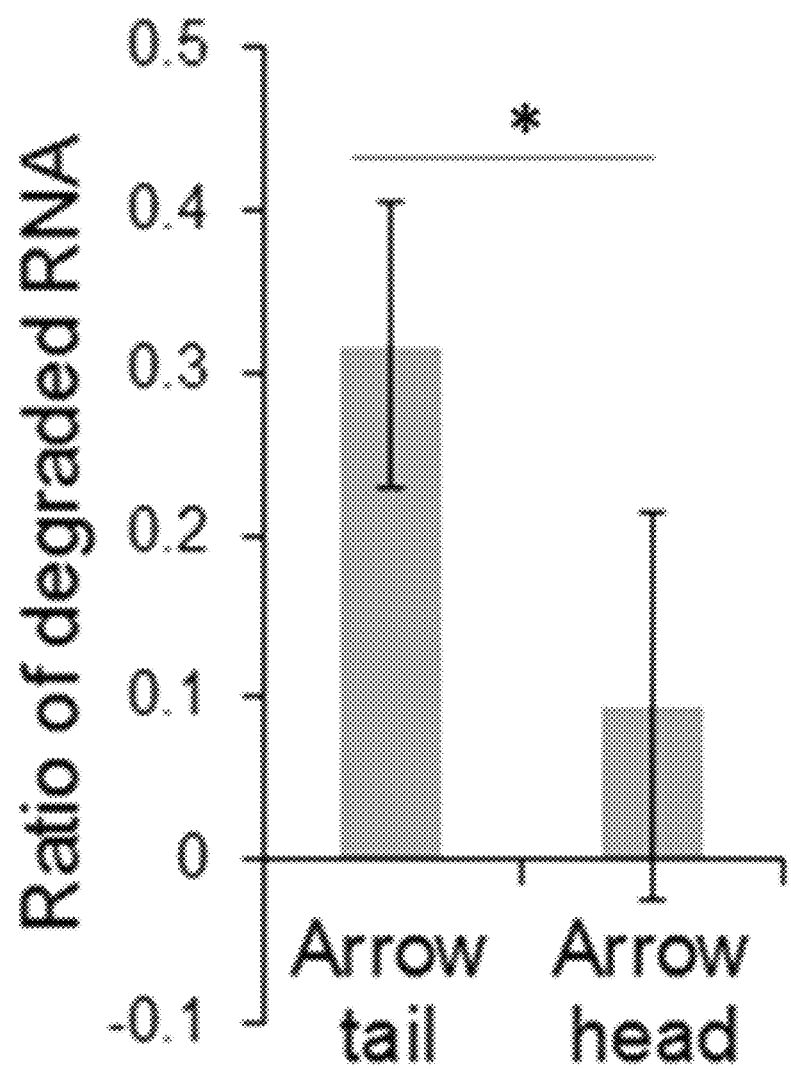

The orientation and angle of the arrow-shaped pRNA-3WJ nanostructure was used to control RNA loading or surface display of EVs. Serum digestion was performed to confirm the localization of 2'-F RNA nanoparticles with EVs. Although 2'-F 3WJ RNA nanoparticles are relatively resistant to RNaseA (FIG. 19a), they can be digested in 67% fetal bovine serum (FBS) and incubated at 37° C. for 2 hr (FIG. 19b). $Alexa_{647}$-2'F RNA nanoparticle-displaying EVs were purified from free RNA nanoparticles by ultracentrifugation, then subjected to serum digestion. $Alexa_{647}$-2'F RNA with cholesterol on the arrow-tail for EVs decoration were degraded (31.6±8.8%) much more than the arrow-head cholesterol-decorated counterparts (9.5±11.9%) after 37° C. FBS incubation (FIG. 13a-d). These results indicate that cholesterol on the arrow-tail promoted display of either folate-3WJ or RNA aptamers on the surface of the EVs and were therefore degraded; while cholesterol on the arrow-head promoted RNA nanoparticles entering EVs, as evidenced by the protection of the $Alexa_{647}$-2'F RNA nanoparticles against serum digestion. In the arrow-tail configuration, it seems as if the two arms that form a 60° angle can act as a hook to lock the RNA nanoparticle in place. If this was the case, the effect would prevent the hooked RNA from passing through the membrane (FIG. 13a).

The concentration of FBS used in the serum digestion experiment was kept extremely high purposefully to degrade the externally displayed RNA on EVs. The decorated $PSMA_{apt}$-3WJ 2'F RNA nanoparticles have been shown to remain stable and intact under physiological conditions (Binzel, D., et al. Molecular Therapy 24, 1267-1277 (2016); Shu, D., et al. ACS Nano 9, 9731-9740 (2015)).

Figure 13E:
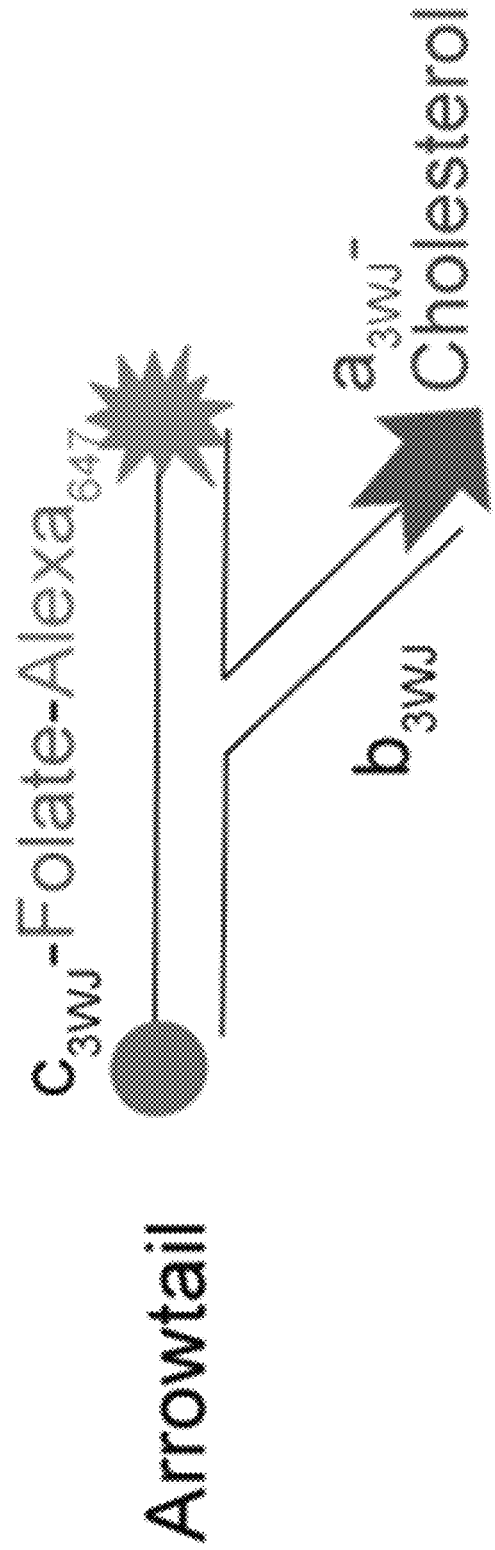
Figure 13F:
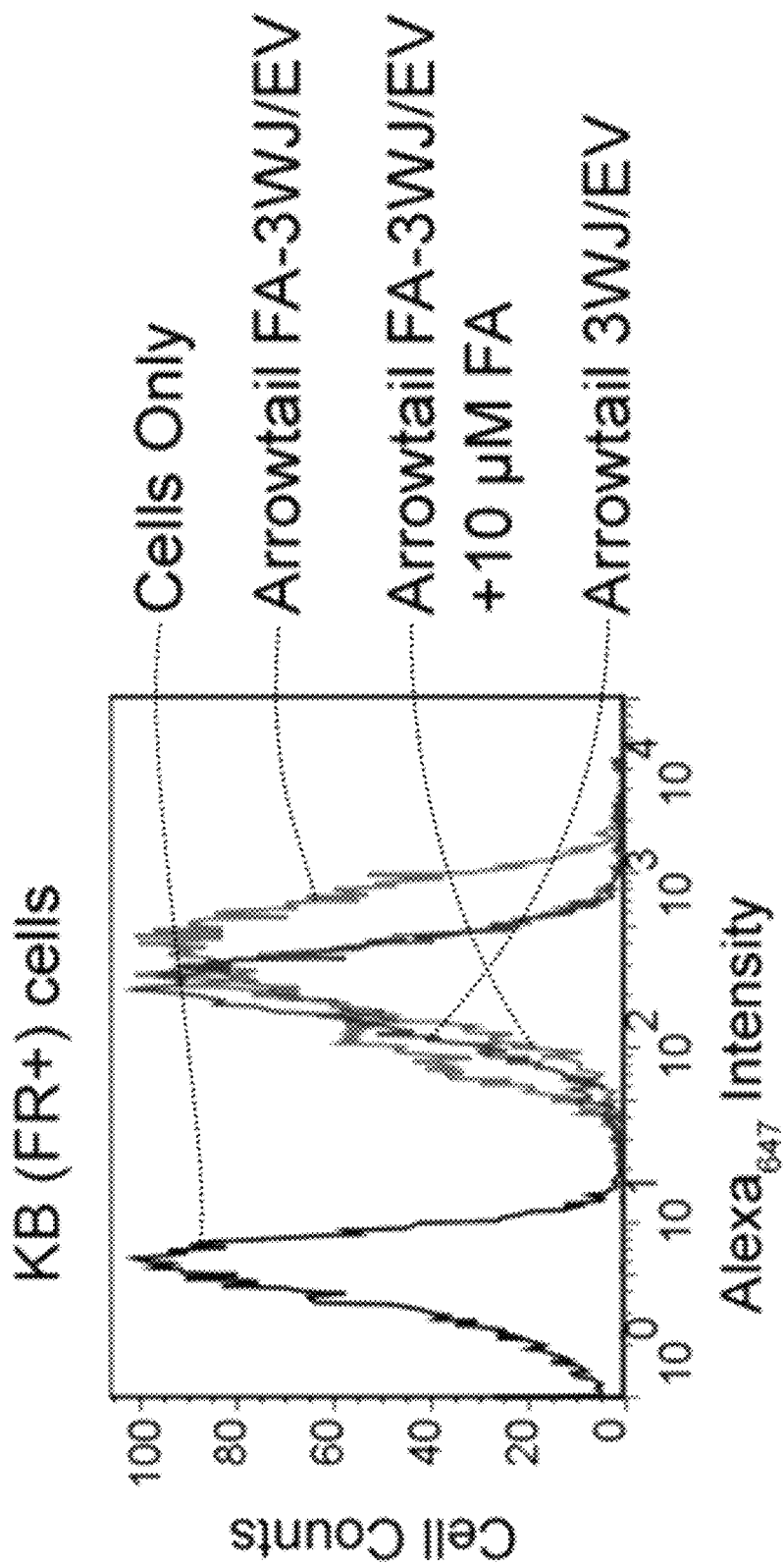
Figure 13G:
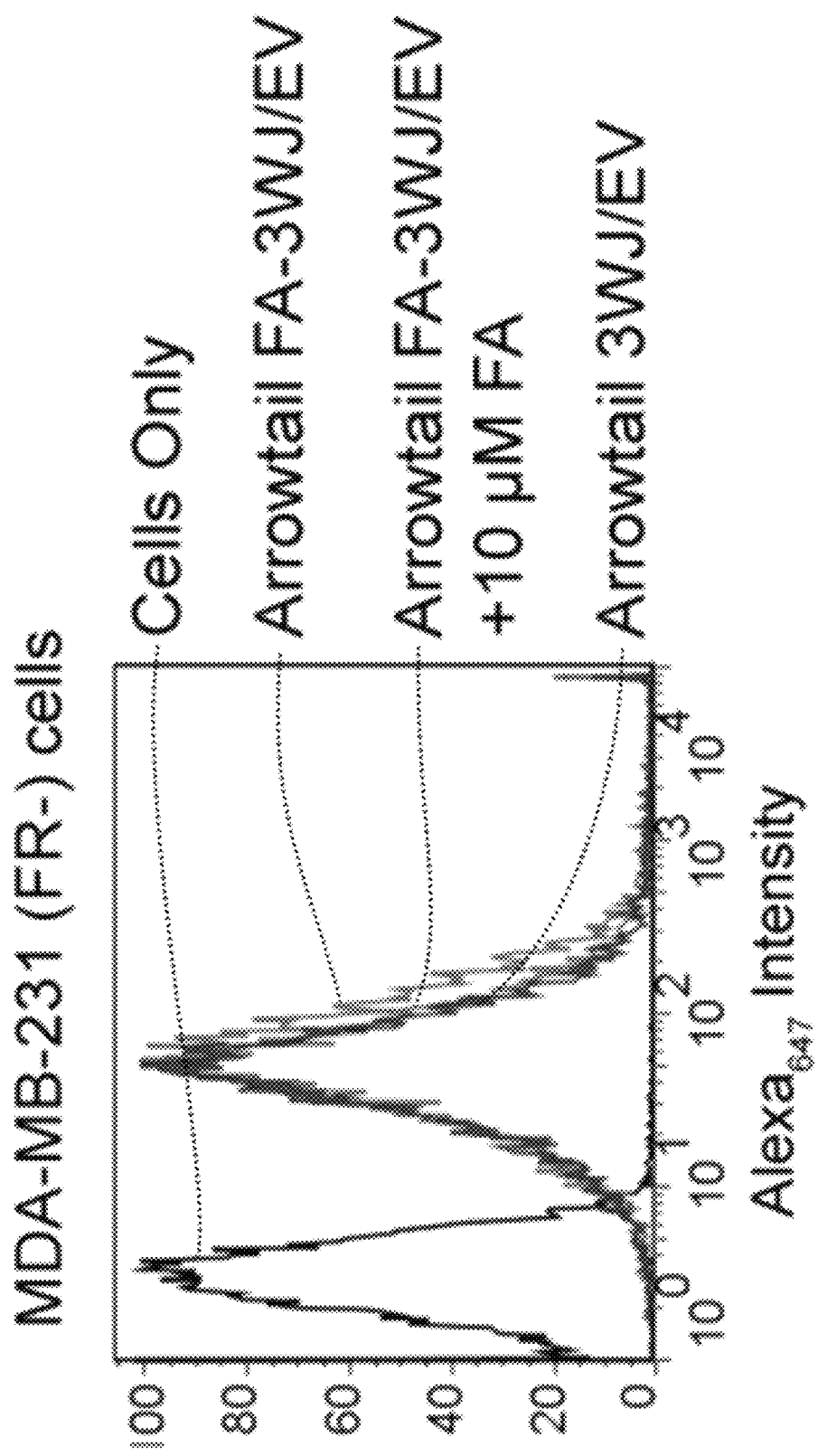

2.2. Differentiation Between Entry or Surface Display on EVs by Competition Assay As described above, when cholesterol was attached to the arrow-tail of pRNA-3WJ, the RNA nanoparticles were anchored on the membrane of EVs, and the incorporated ligands were displayed on the outer surface of the EVs (FIG. 13a). An increase in the binding of EVs to folate receptor-overexpressing KB cells was detected by displaying folate on the EV surface using arrow-tail cholesterol RNA nanoparticles (FIG. 13e, 13f). When incubating with low folate receptor-expressing MDA-MB-231 breast cancer cells, arrow-tail-shaped FA-3WJ/EV did not enhance its cell binding compared to arrow-tail ligand free 3WJ/EV (FIG. 13g). The surface display of folate was further confirmed by free folate competition assay, in which a baseline of binding by the cholesterol arrow-tail FA-3WJ/EVs to KB cells was established. A decrease (48.3±0.6%) in the cellular binding to KB cells was detected when 10 µM of free folate was added to compete with the cholesterol-arrow-tail FA-3WJ/EV for folate receptor binding (FIG. 13f). In contrast, competition by free folate in arrow-head FA-3WJ/EV (FIG. 13h) binding to KB cells was much lower (24.8±0.6%) (FIG. 13i), which is possibly due to partial internalization of the arrow-head-shaped FA-3WJ nanoparticle into the EVs, which resulted in a lower display intensity of folate on the surface of the EVs.

EVs can mediate intercellular communication by transporting mRNA, siRNA, miRNA or proteins and peptides between cells. They internalize into recipient cells through various pathways, including micropinocytosis, receptor-mediated endocytosis, or lipid raft-mediated endocytosis (Marcus, M. E., et al. Pharmaceuticals. (Basel) 6:659-680 (2013)). Although the natural process for the uptake of EVs is not ligand-dependent, the arrow-tail cholesterol RNA-3WJ allows for displaying ligand onto the surface of EVs, and increasing its targeting efficiency to the corresponding receptor overexpressing cancer cells.

Figure 14A:
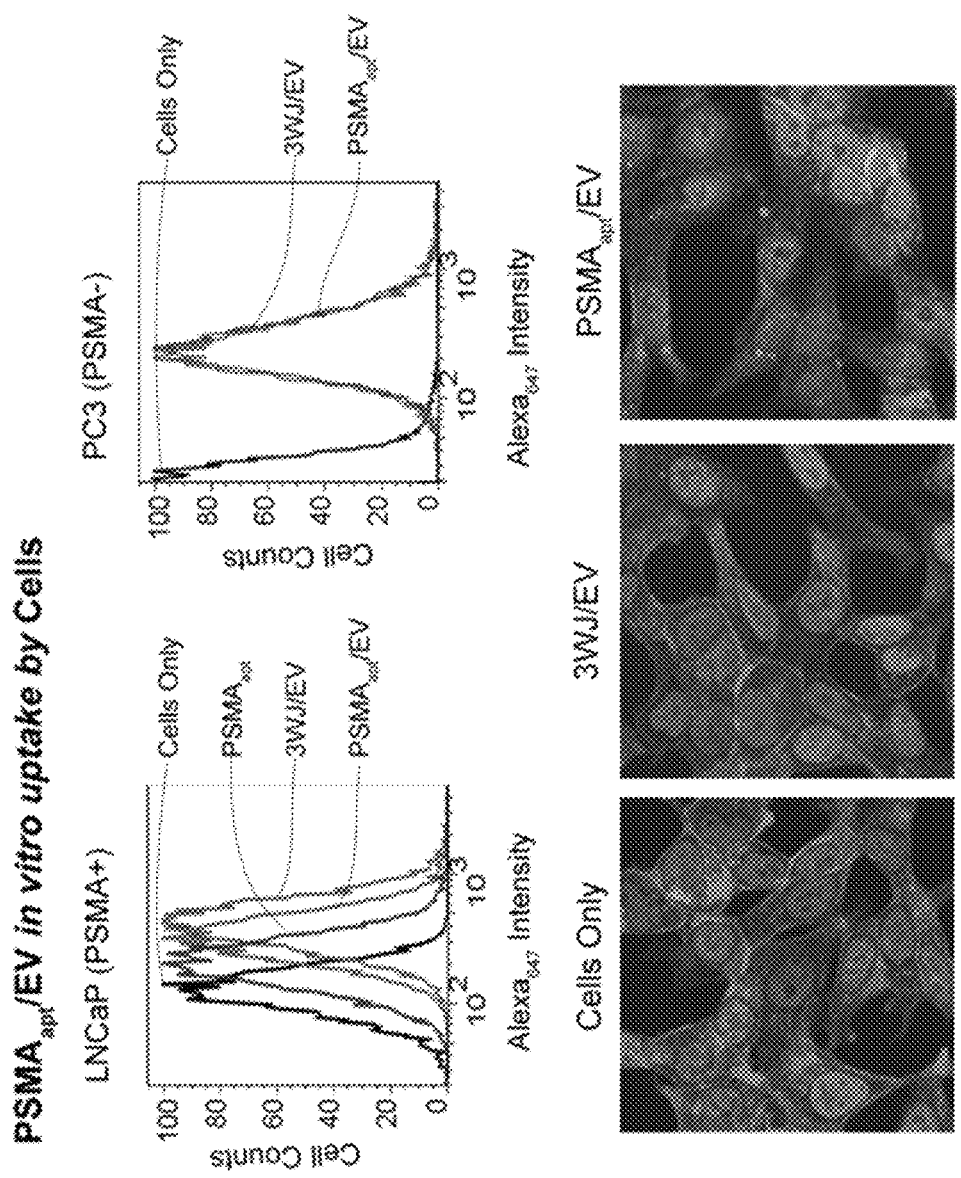
FIGS. 14A to 14C show specific binding and siRNA delivery to cells in vitro using PSMA aptamer-displaying EVs.
Figure 14B:
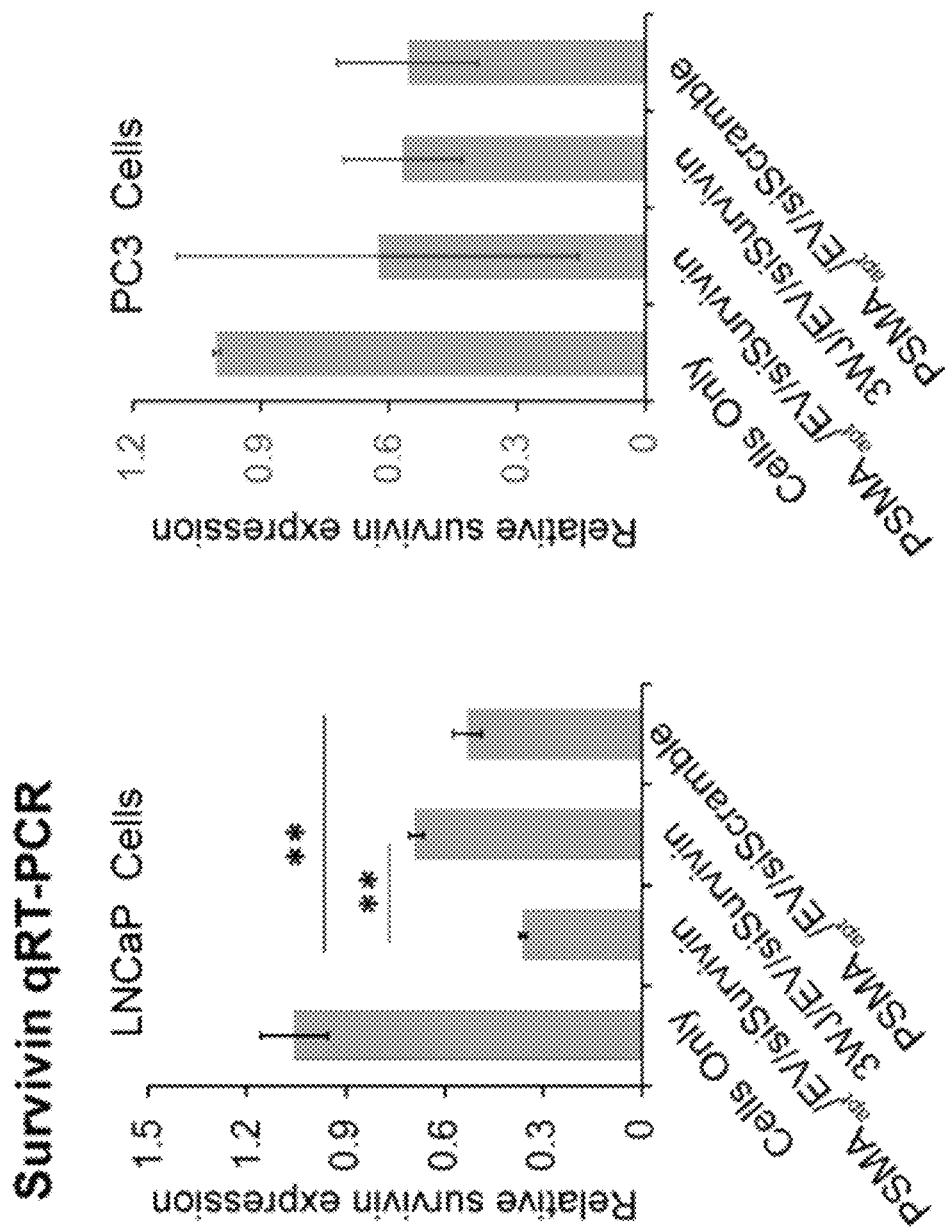
Figure 14C:
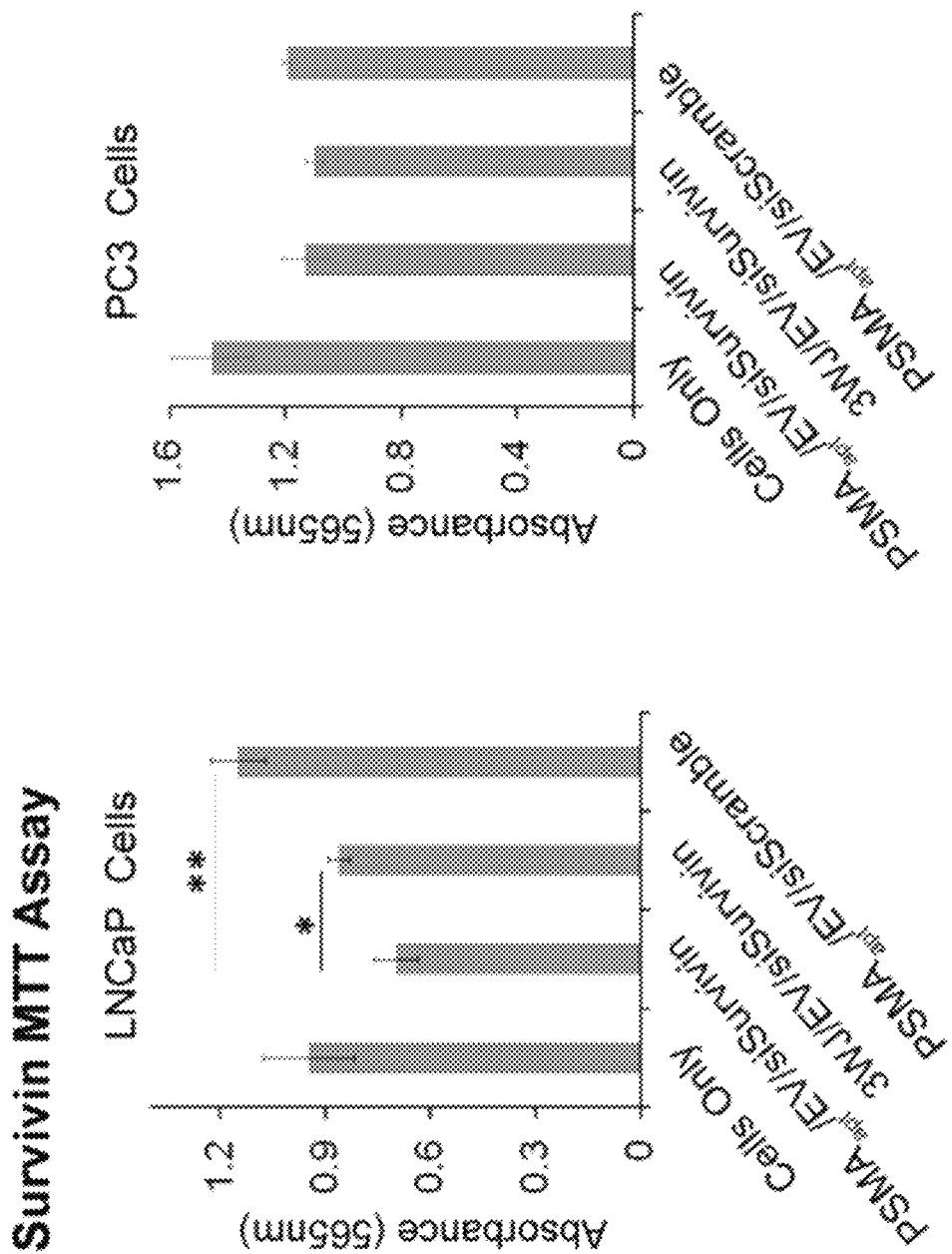
Figure 20D:
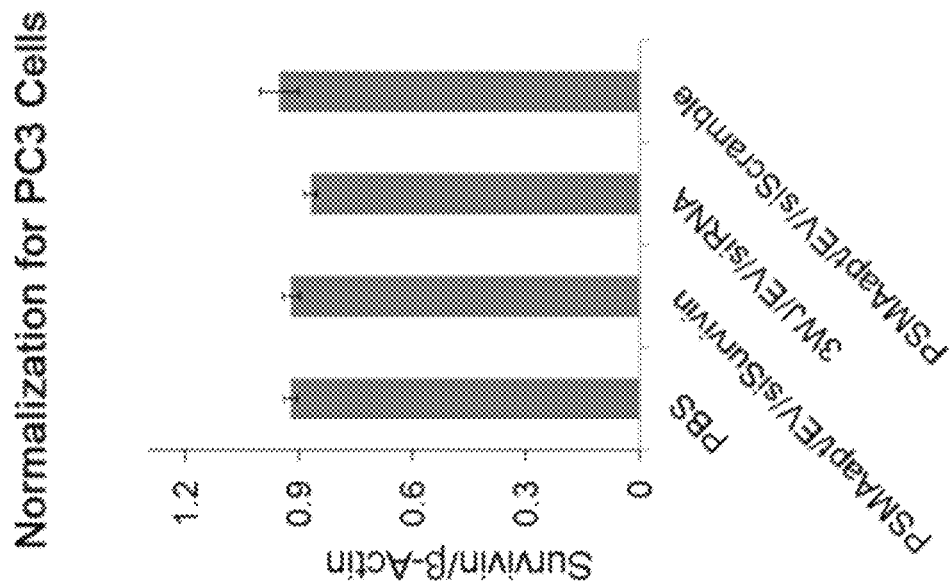
Figure 20C:
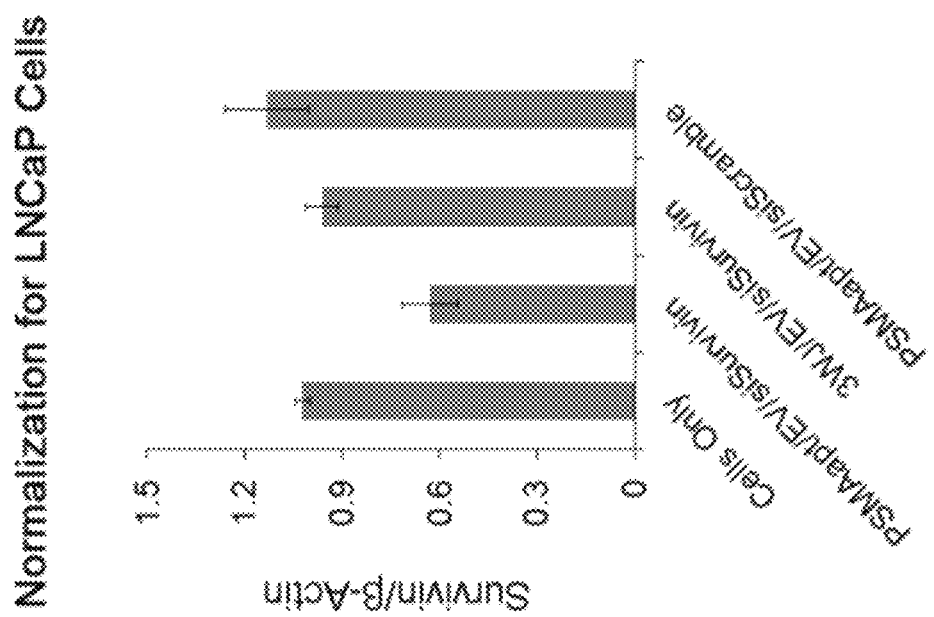

3. Cancer-Targeting and Gene Silencing of the RNA-Displaying EVs in Cell Cultures Specific cancer cell-targeting is one important prerequisite for applying nano-vesicles to cancer therapy. The targeting, delivery and gene silencing efficiency of the PSMA aptamer-displaying EVs were examined in PSMA-positive LNCaP prostate cancer cells. To confer RNase resistance, 2'-F modifications were applied to the RNA nanoparticles placed on the surface of EVs (Shu, D., et al. Nature Nanotechnology 6:658-667 (2011)), while the thermodynamic stability of pRNA-3WJ provided a rigid structure to ensure the correct folding of RNA aptamers (Shu, D., et al. Nature Nanotechnology 6:658-667 (2011); Binzel, D. W. et al. Biochemistry 53:2221-2231 (2014)). PSMA aptamer-displaying EVs showed enhanced binding and apparent uptake to PSMA(+) LNCaP cells compared to EVs without PSMA aptamer by flow cytometry and confocal microscopy analysis, but not to the PC-3 cells, which is a low PSMA receptor expressing cell line (FIG. 14a). Upon incubation with LNCaP cells, $PSMA_{apt}$/EV/siSurvivin was able to knock down survivin expression at the mRNA level as demonstrated by real-time PCR (69.8.1±9.37%, p<0.001) (FIG. 14b) and protein level as shown by Western Blot (62.89±8.5%, p<0.05) (FIG. 20). Cell viability by MTT assays indicated that the viability of LNCaP cells was decreased as a result of survivin siRNA delivery (69.6±6.4%, p<0.05) (FIG. 14c).

4. The Ligand Displaying EVs Target Tumors

Figure 15A:
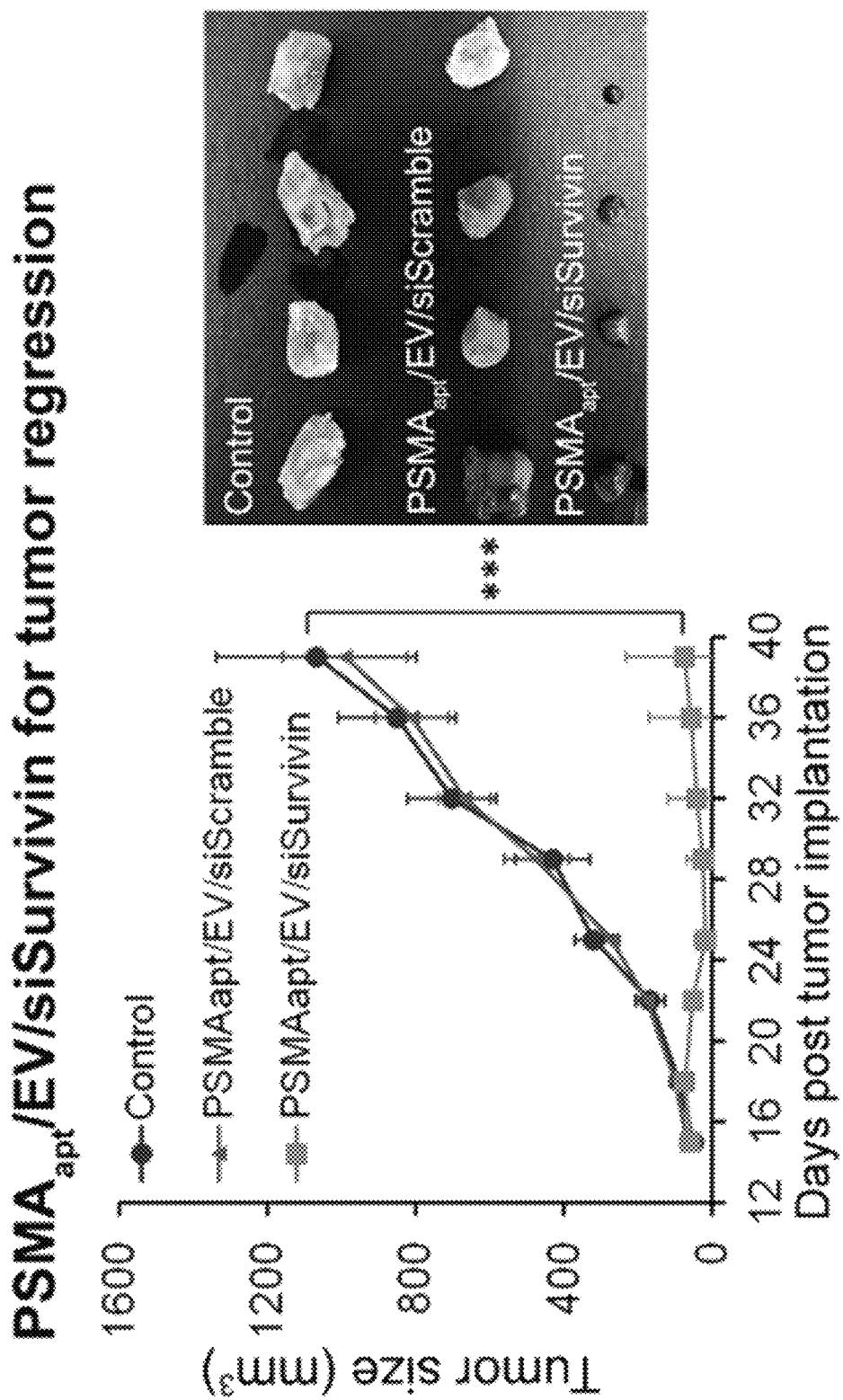
FIGS. 15A to 15C shows animal trials using ligands displaying EV for tumor inhibition.

The tumor targeting and biodistribution properties of ligand-displaying EVs were evaluated. FA-3WJ/EVs were systemically administered via the tail vein into KB subcutaneous xenograft mice model. 3WJ/EVs and PBS treated mice were tested as a control. Ex vivo images of mice healthy organ and tumors taken after 8 hr showed that the FA-3WJ/EVs mainly accumulated in tumors, with low accumulation in vital organs in comparison with PBS control mice, and with more accumulation in tumors in comparison with 3WJ/EVs control mice (FIG. 15a). Normal EVs without surface modification usually showed accumulation in liver after systemic delivery (Ohno, S., et al. Mol Ther. 21:185-191 (2013)). Both RNA and cell membranes are negatively charged. The electrostatic repulsion effect has been shown to play a role in reducing the accumulation of RNA nanoparticles in healthy organs (Binzel, D., et al. Molecular Therapy 24:1267-1277 (2016); Shu, D., et al. ACS Nano 9:9731-9740 (2015); Haque, F., et al. Nano Today 7:245-257 (2012)). It is hypothesized that displaying targeting RNAs on the EVs surface reduces their accumulation in normal organs, and the ideal nano-scale size of RNA displaying EVs facilitates tumor targeting via Enhance Permeability and Retention (EPR) effects, thereby avoiding toxicity and side effects.

5. Inhibition of Tumor Growth by Ligand-3WJ-Displaying EV as Demonstrated in Animal Trials

5.1. PSMA Aptamer Displaying EVs Completely Inhibits Prostate Cancer Growth in Mice.

Figures 15B, 15C:
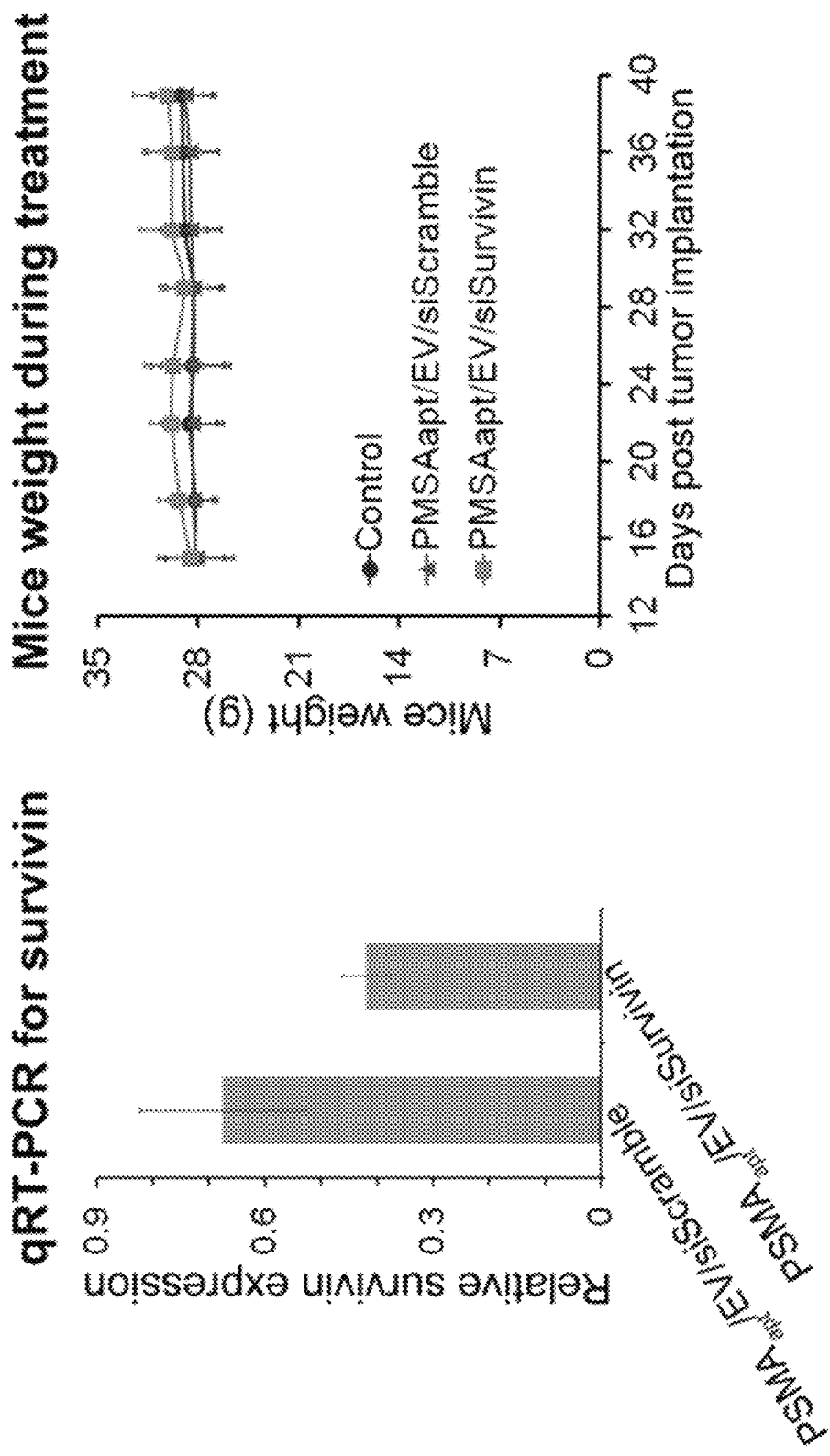

The therapeutic effect of PSMA aptamer-displaying EVs for prostate cancer treatment was evaluated using LNCaP-LN3 tumor xenografts (Li, Y., et al. Prostate Cancer Prostatic. Dis. 5:36-46 (2002); Pettaway, C. A., et al. Clin. Cancer Res 2:1627-1636 (1996)). Treatment with $PSMA_{apt}$/EV/siSurvivin (1 dose every 3 days; total 6 doses) completely suppressed in vivo tumor growth, compared to control groups (FIG. 15b). EVs are biocompatible and well tolerated in vivo as no significant toxicity was observed, as indicated by body weights of the mice, assessed over 40 days post-treatment (FIG. 15c). Analyzing the survivin mRNA expression levels in the tumor by real time PCR using GAPDH as internal control showed a trend of knocking down survivin by $PSMA_{apt}$/EV/siSurvivin (FIG. 15d). Taken together, PSMA aptamer displaying EVs is a promising vector for delivering survivin siRNA in vivo and systemic injection of $PSMA_{apt}$/EV/siSurvivin might achieve desired therapeutic efficacy.

The in vivo cancer growth inhibition effect was more pronounced than in vitro MTT assays in prostate cancer studies. The displaying of PSMA aptamer on the surface of EVs slightly enhanced its targeting to PSMA receptor overexpressing cancer cells in vitro, while the negatively charged RNA on EV surface might have minimized its nonspecific distribution to healthy cells as seen in the FA-3WJ/EVs biodistribution test. The EPR effect could also promote the homing of nanoscale EVs into tumors in vivo; although the biodistribution presented in FIG. 15a may not apply to the functional evaluation presented in FIG. 15b. All these results suggest that RNA aptamer displaying EVs are suitable for in vivo applications.

5.2. EGFR Aptamer Displaying EVs Inhibited Breast Cancer Growth in Mice.

Figure 16A:
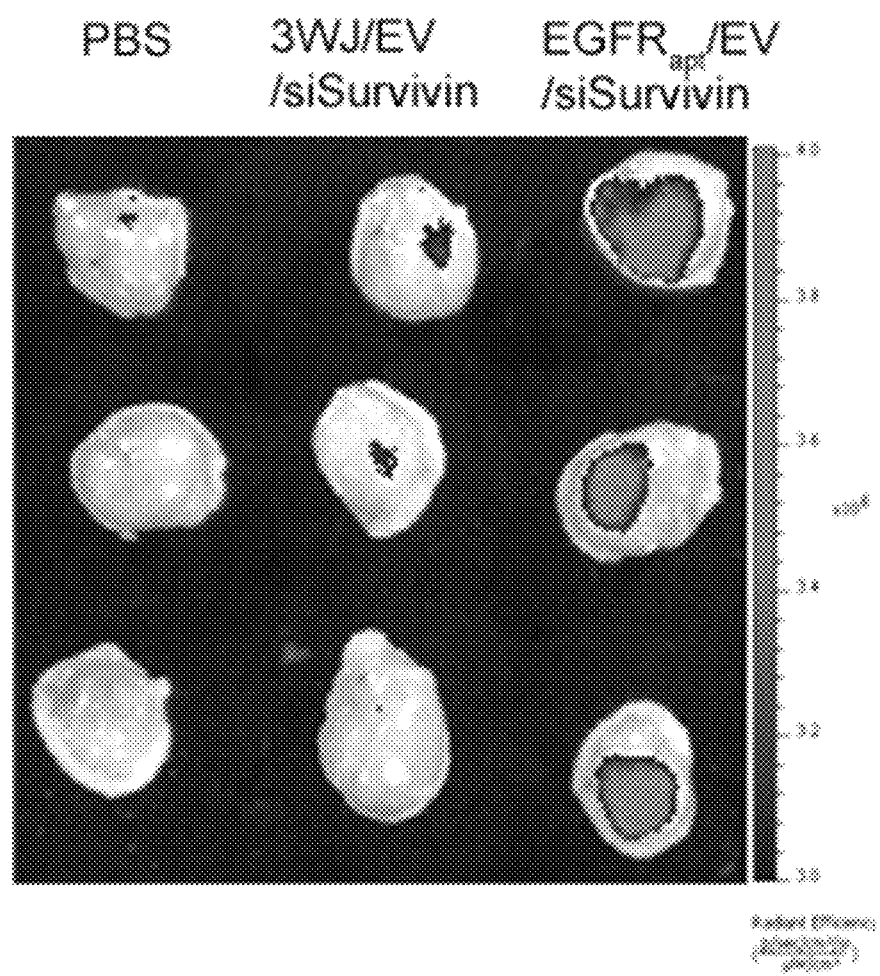
FIGS. 16A to 16D show EGFR aptamer displaying EVs can deliver survivin siRNA to breast cancer orthotopic xenograft mouse model.
Figure 16B:
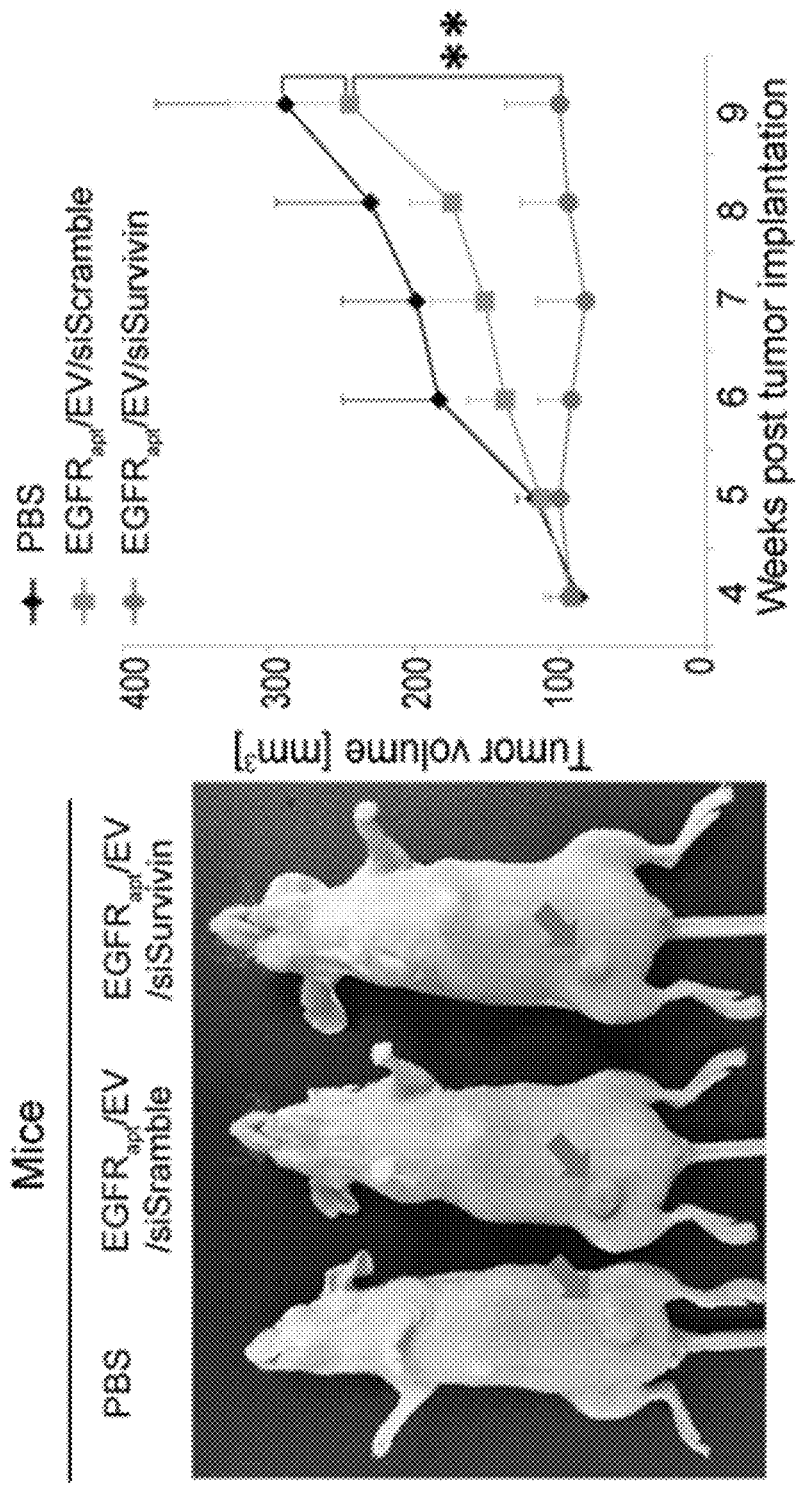
Figure 16D:
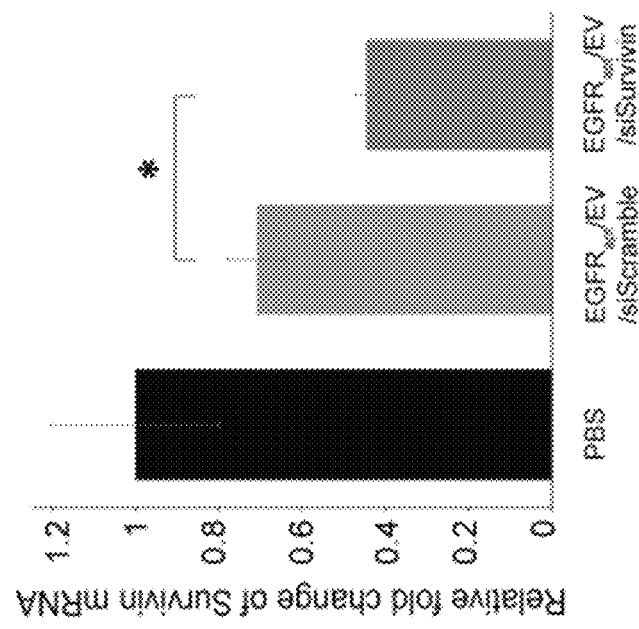
Figure 16C:
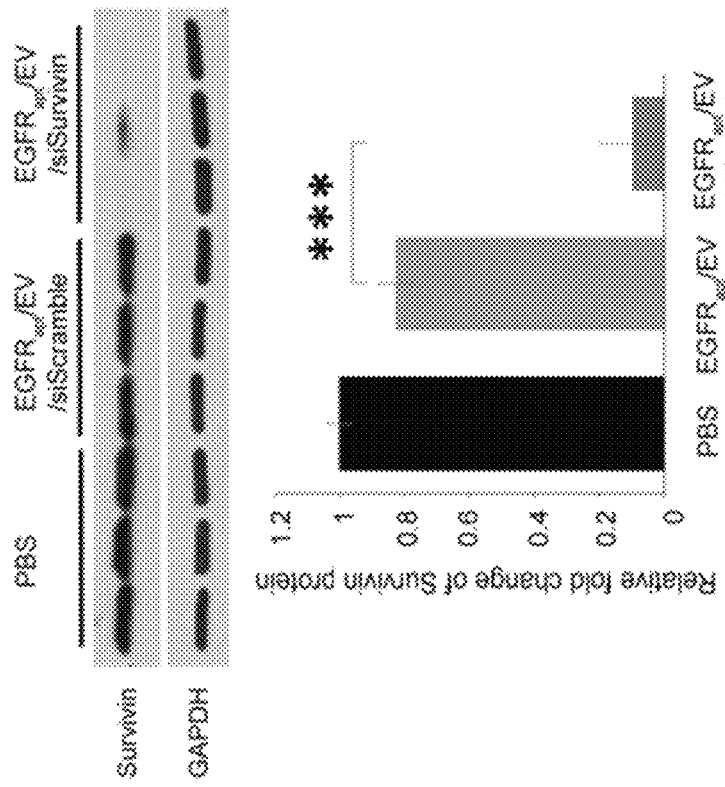
Figure 21B:
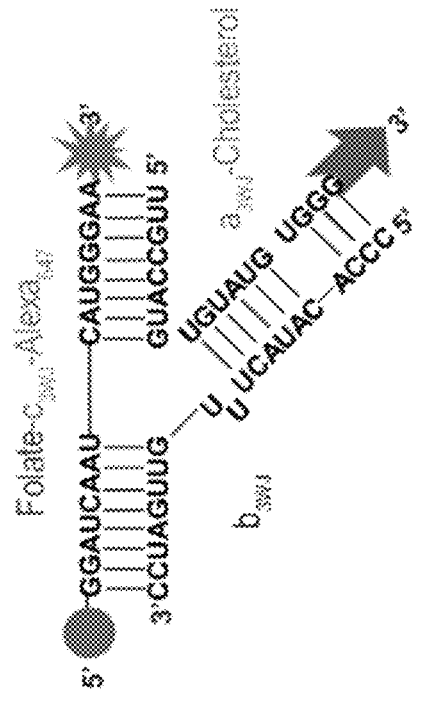
FIGS. 21A and 21B show primary sequence and secondary structure of RNA nanoparticles.
Figure 21A:
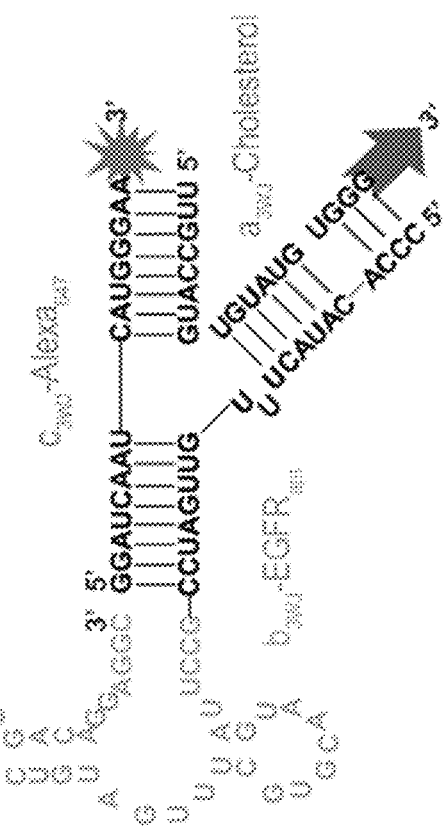

Overexpression of EGFR in breast cancer cells is associated with high proliferation, and risk of relapse in patients receiving treatment (Rimawi, M. F., et al. Cancer 116:1234-1242 (2010)). pRNA-3WJ nanoparticles harboring EGFR aptamer (FIG. 21a) were constructed for display on EV surface, and the EVs were loaded with survivin siRNA. The resulting $EGFR_{apt}$/EV/siSurvivin particles were administered via tail vein into the MDA-MB-468 orthotopic xenograft tumor bearing mice. 3WJ/EV/siSurvivin (without targeting ligand) and PBS treated mice served as controls. The analysis was done with three mice per group. Ex vivo images taken after 8 hrs showed that the EGFR$_{apt}$/EV/siSurvivin accumulated more in tumors than the control groups (FIG. 16a), indicating that displaying EGFR aptamer on the surface of EVs greatly enhanced its tumor targeting capabilities in vivo (Li, Y., et al. Prostate Cancer Prostatic. Dis. 5:36-46 (2002); Pettaway, C. A., et al. Clin. Cancer Res 2:1627-1636 (1996)). Treatment with EGFR$_{apt}$/EV/siSurvivin at a dose of 0.5 mg siRNA/kg of mice body weight (6 doses weekly) significantly suppressed in vivo tumor growth as monitored by tumor volume, compared to controls (FIG. 16b). The specific knockdown of survivin was validated from three representative tumors from each group by both Western blot (FIG. 16c) and quantitative real-time PCR (FIG. 16d), where GAPDH was used as an internal normalization control. The results indicate that successful delivery of survivin siRNA to breast tumor cells inhibited survivin expression at both protein and mRNA levels.

5.3. Folate Displaying EVs Inhibited Colorectal Cancer Growth in Mice.

Figure 17A:
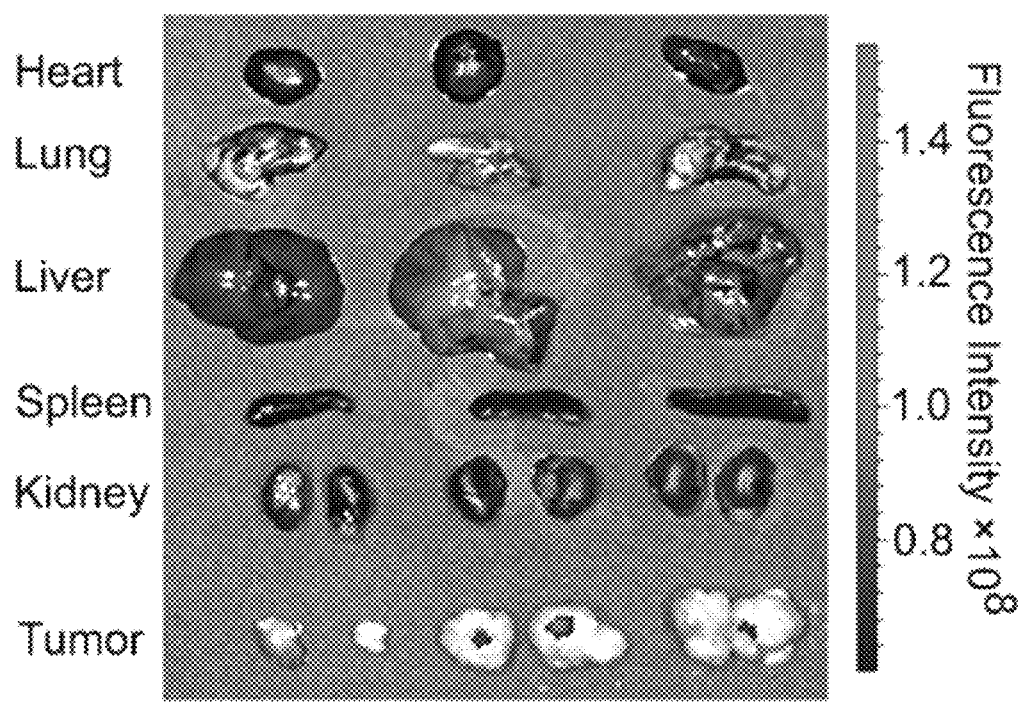
FIGS. 17A to 17C show folate displaying EVs can deliver survivin siRNA to patient derived colorectal cancer xenograft (PDX-CRC) mouse model.
Figure 17B:
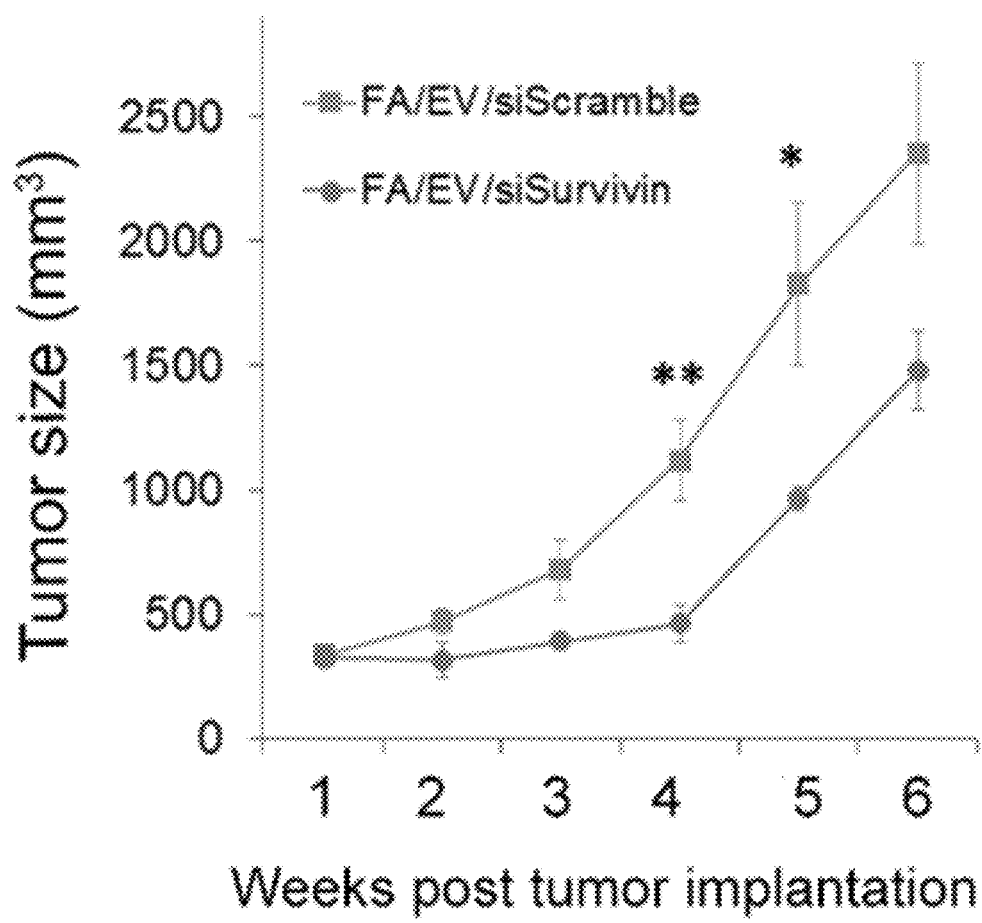
Figure 17C:
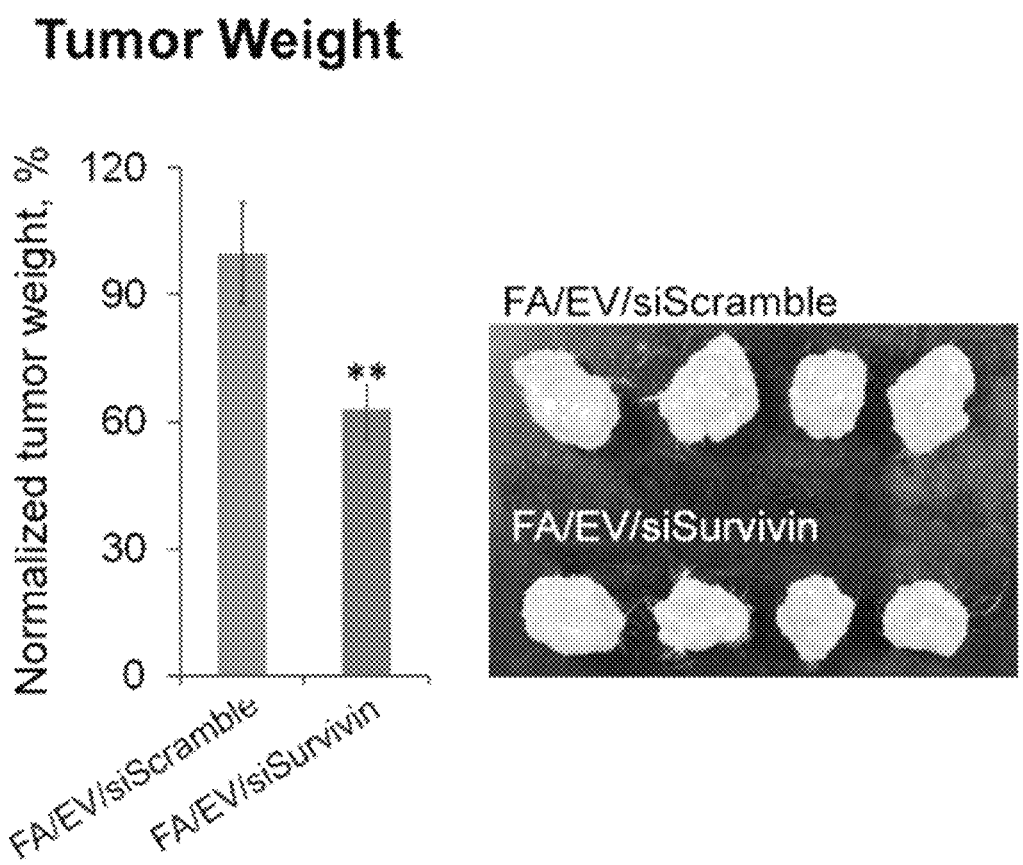
Figure 22:
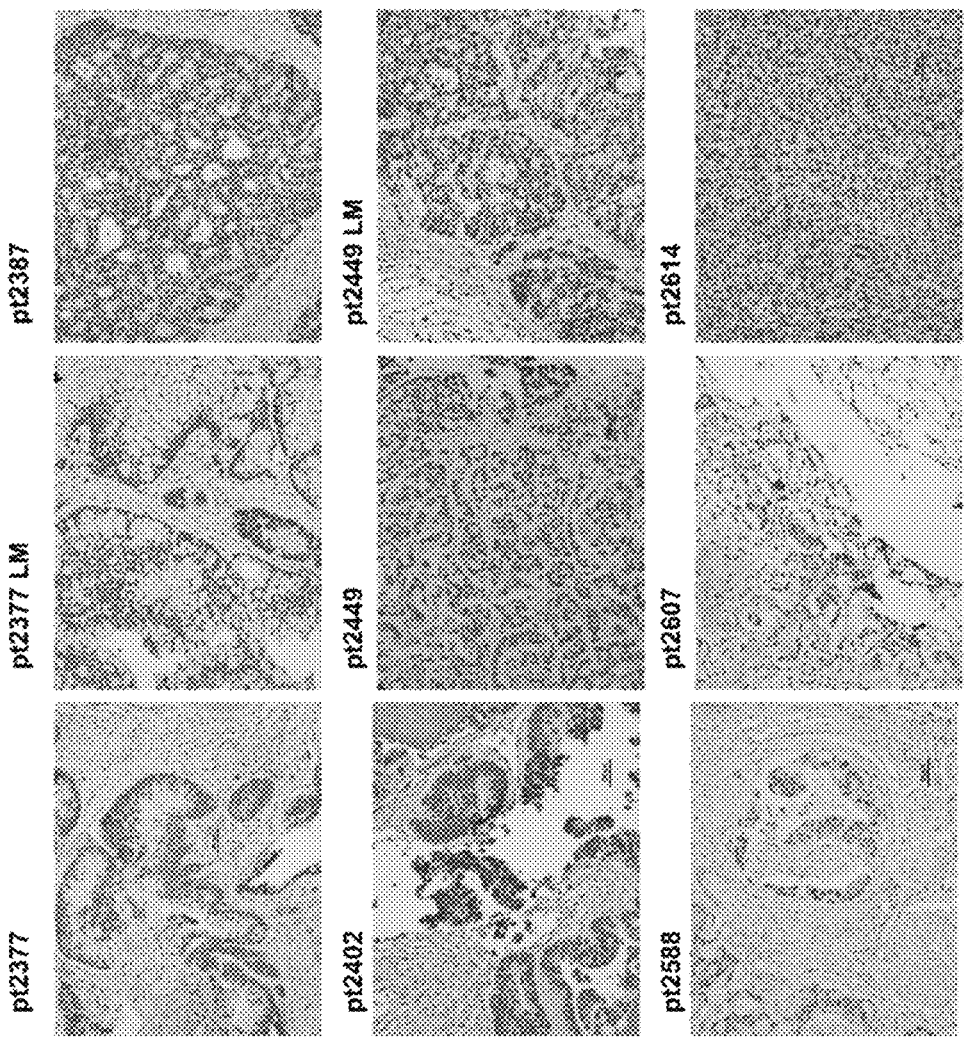
FIG. 22 shows analysis of survivin expression in CRC PDX tumors. Examples of immunohistochemical staining for survivin (Survivin (71G4B7) Rabbit mAb #2808; Cell Signaling, 1:500) (n=9 patient samples).

Survivin gene, the anti-apoptotic protein, is upregulated in most colorectal cancers, as tested by immunohistochemistry (IHC) imaging of tumor tissues from 9 colorectal cancer patients (FIG. 22). Utilizing a similar strategy, pRNA-3WJ nanoparticles harboring folate (FIG. 21b) were constructed for display on EV surface, and the EVs were loaded with survivin siRNA. The functionalized EVs were then evaluated in a clinically relevant patient derived CRC xenograft (PDX-CRC) mouse model. Treatment with FA/EV/siSurvivin at a dose of 0.5 mg siRNA/kg of mice body weight (6 doses weekly) significantly suppressed in vivo tumor growth as measured by tumor volume and tumor weight, compared to control group (FIG. 17a-b). The data suggests that folate displaying EVs can be used vector for delivering siRNA for colorectal cancer treatment.

Discussion

The application of RNA interference technology, such as siRNA, to knockdown gene expression has been of great interest (Pecot, C. V., et al. Nat Rev. Cancer 11:59-67 (2011)). The nanometer-scale EVs (EL-Andaloussi S., et al. Nat Rev. Drug Discov. 12:347-357 (2013); Valadi, H. et al. Nat Cell Biol 9:654-659 (2007); El-Andaloussi, S. et al. Adv. Drug Deliv. Rev. 65:391-397 (2013); van Dommelen, S. M., et al. J Control Release 161:635-644 (2012)) can deliver biomolecules into cells by direct fusion with the cell membrane through tetraspanin domains, or back-fusion with endosomal compartment membranes for endosome escape. Therapeutic payloads, such as siRNA, can fully function after delivery to cells by EVs (Pecot, C. V., et al. Nat Rev. Cancer 11:59-67 (2011)). The nanometer-scale EVs (EL-Andaloussi S., et al. Nat Rev. Drug Discov. 12:347-357 (2013); Valadi, H. et al. Nat Cell Biol 9:654-659 (2007); El-Andaloussi, S. et al. Adv. Drug Deliv. Rev. 65:391-397 (2013); van Dommelen, S. M., et al. J Control Release 161:635-644 (2012)). However, EVs lack selectivity and can also randomly fuse to healthy cells. To generate specific cell-targeting EVs, approaches by in vivo expression of cell specific peptide ligands on the surface of EVs have been explored (varez-Erviti, L., et al. Nat Biotechnol. 29:341-345 (2011); Ohno, S., et al. Mol Ther. 21:185-191 (2013)). However, in vivo expression of protein ligands is limited to the availability of ligands in their producing cell types (EL-Andaloussi S., et al. Nat Rev. Drug Discov. 12:347-357 (2013); van Dommelen, S. M., et al. J Control Release 161:635-644 (2012); Wiklander, O. P., et al. J Extracell. Vesicles. 4, 26316 (2015)). It would be desirable for in vivo cancer cell targeting using in vitro surface display technology to display nucleic acid-based or chemical targeting ligands on EVs.

Figure 13H:
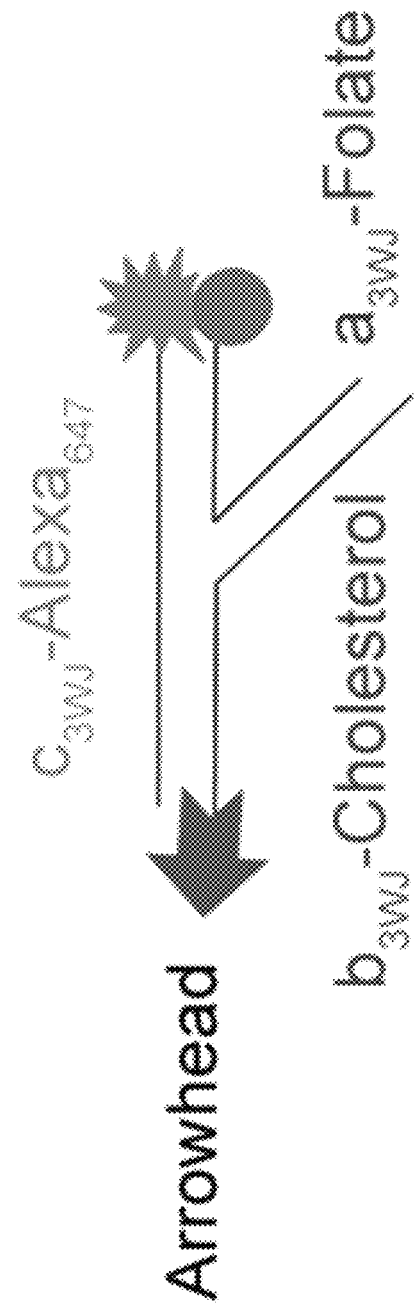
Figure 13I:
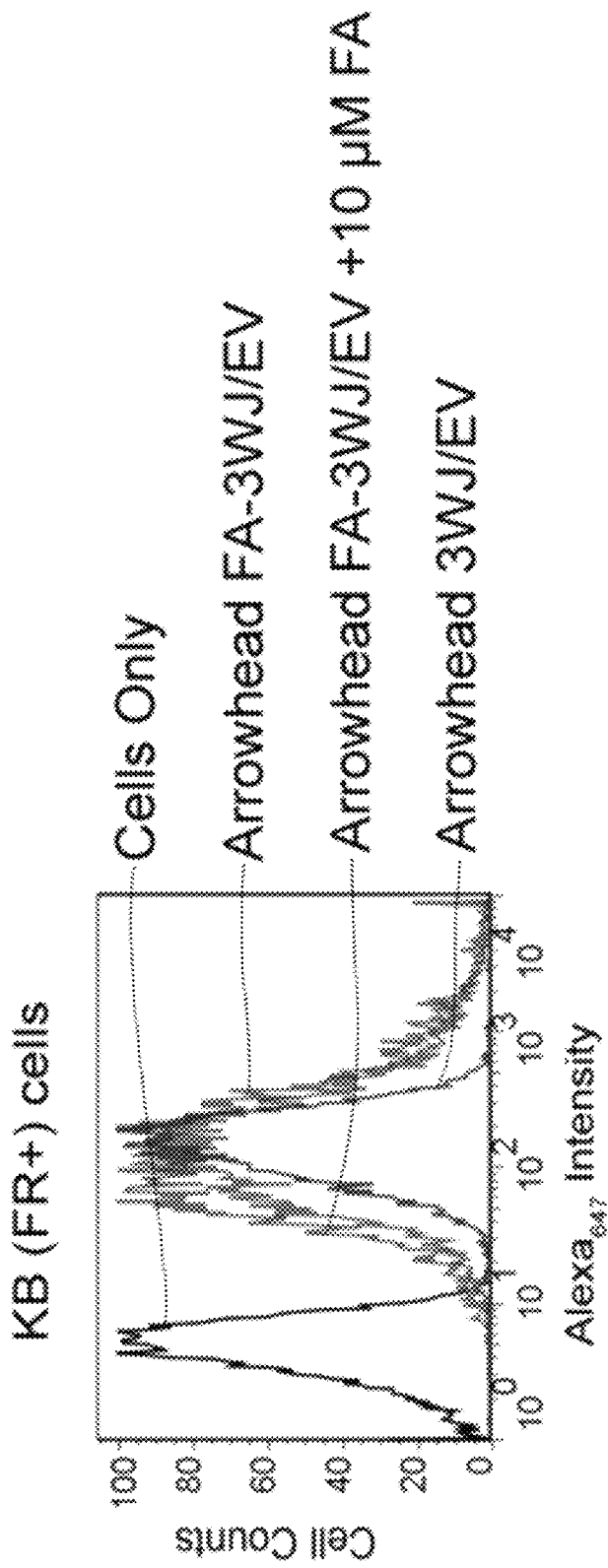

This example reports the in vitro application of RNA nanotechnology (Guo, P. Nature Nanotechnology 5:833-842 (2010)) to reprogram natural EVs for specific delivery of siRNA to cancer models in vitro and in animal models (FIG. 12a-12c). Taking advantage of the thermodynamically stable properties of pRNA-3WJ (Shu, D., et al. Nature Nanotechnology 6:658-667 (2011); Binzel, D. W. et al. Biochemistry 53:2221-2231 (2014); Shu, D., et al. Nucleic Acids Res. 42:e10 (2013)), multifunctional RNA nanoparticles harboring membrane-anchoring lipid domain, imaging modules and targeting modules were generated. The arrow-shaped pRNA-3WJ offered the opportunity to control either partial loading of RNA into EVs or decoration of ligands on the surface of EVs. With cholesterol placed on the arrow-tail of the 3WJ, the RNA-ligand was prevented from trafficking into EVs, ensuring oriented surface display of targeting modules for cancer receptor binding. This was explicitly demonstrated by serum digestion and folate competition assays (FIG. 13f), as well as by enhanced binding to LNCaP cells after PSMA aptamer display (FIG. 14a) and during in vivo breast cancer by the EGFR aptamer display (FIG. 16a). Additionally, the placement of cholesterol on the arrow-head allowed for partial internalization of the RNA nanoparticle within the EVs (FIG. 13b, 13h). The incorporation of arrow-tail 3WJ-RNA nanoparticles to the surface of the EVs not only provided a targeting ligand to the EVs, but also added a negative charge on the EVs surface. Displaying negatively charged RNA nanoparticles on EV surface might be able to reduce the non-specific binding of EV to normal cells, as negatively charged RNA nanoparticles with a proper ligand tend to accumulate into tumors specifically after systemic administration (Binzel, D., et al. Molecular Therapy 24: 1267-1277 (2016); Shu, D., et al. ACS Nano 9:9731-9740 (2015); Hague, F., et al. Nano Today 7:245-257 (2012)). The cholesterol-TEG-modified RNA nanoparticles should preferentially anchor onto the raft-forming domains of the lipid bilayer of EVs (Bunge, A., et al. J Phys Chem. B 113:16425-16434 (2009)), and further studies will be necessary to illustrate this process. EVs have the intrinsic ability to back-fuse with endosomal compartment membranes following receptor mediated endocytosis (EL-Andaloussi S., et al. Nat Rev. Drug Discov. 12:347-357 (2013); Valadi, H. et al. Nat Cell Biol 9:654-659 (2007); El-Andaloussi, S. et al. Adv. Drug Deliv. Rev. 65:391-397 (2013)). The disclosed in vitro decoration approach preserved the favorable endogenous composition of EVs as delivery vectors, thus eliminating the need of building artificial endosome-escape strategies into the EV vectors compared to using other synthetic nanovectors for siRNA delivery (Varkouhi, A. K. et al. J Control Release 151:220-228 (2011); Kilchrist, K. V. et al. Cell Mol Bioeng. 9:368-381 (2016)).

In summary, this example demonstrates the effective reprogramming of native EVs using RNA nanotechnology. Nanoparticle orientation controls RNA loading or surface display on EVs for efficient cell targeting, siRNA delivery and cancer regression. The reprogrammed EVs displayed robust physiochemical properties, enhanced cancer cell specific binding, and efficient intracellular release of siRNA to suppress tumor growth in animal models.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A composition comprising an RNA nanoparticle anchored on the surface of an extracellular vesicle membrane,
wherein the nanoparticle is assembled from one or more ribonucleic acid strands duplexed together to form a secondary structure with three or more projecting stem loops,
wherein at one of the three or more projecting stem loops is conjugated to a cholesterol moiety
wherein at one of the three or more projecting stem loops comprises one or more functional moieties, and
wherein at least one of the three or more projecting stem loops physically blocks encapsulation of the nanoparticle into the extracellular vesicle.

2. The composition of claim 1, wherein at least one of the three or more ribonucleic acid strands comprise a pRNA-3WJ core.

3. The composition of claim 1, wherein the RNA nanoparticle is assembled from three ribonucleic acid strands comprising the nucleic acid sequence SEQ ID NO:1, SEQ ID NO:2, and SEQ ID NO:3.

4. The composition of claim 1, wherein one or more of the functional moieties comprises a targeting moiety.

5. The composition of claim 4, wherein the targeting moiety directs the exosome to a cell of interest.

6. The composition of claim 4, wherein the targeting moiety is selected from an RNA aptamer, modified RNA aptamer, DNA aptamer, modified DNA aptamer, and chemical ligand.

7. The composition of claim 1, wherein one or more of the functional moieties comprises a therapeutic moiety or a diagnostic moiety.

8. The composition of claim 7, wherein the therapeutic moiety or a diagnostic moiety comprises an RNA aptamer, a ribozyme, siRNA, protein-binding RNA aptamer, or small molecule.

9. The composition of claim 1, wherein the extracellular vesicle comprises an exosome.

10. A method of targeting an extracellular vesicle to a cell of interest comprising: contacting the cell with a composition comprising an extracellular vesicle displaying an RNA nanoparticle on its surface,
wherein the nanoparticle is assembled from one or more ribonucleic acid strands duplexed together to form a secondary structure with three or more projecting stem loops,
wherein at one of the three or more projecting stem loops is conjugated to a cholesterol moiety, wherein at least one of the three or more projecting stem loops physically blocks encapsulation of the nanoparticle into the extracellular vesicle, and wherein at one of the three or more projecting stem loops comprises at least one targeting moiety that directs the extracellular vesicle to the cell of interest.

11. The method of claim 10, wherein the cell is in a subject.

12. The method of claim 10, wherein the cell is a cancer cell.

13. The method of claim 10, wherein the RNA nanoparticle further comprises a functional moiety.

14. A method of treating disease in a subject, comprising administering to the subject composition comprising an extracellular vesicle displaying an RNA nanoparticle on its surface, wherein the nanoparticle is assembled from one or more ribonucleic acid strands duplexed together to form a secondary structure with three or more projecting stem loops, wherein at one of the three or more projecting stem loops is conjugated to a cholesterol moiety, wherein at least one of the three or more projecting stem loops physically blocks encapsulation of the nanoparticle into the extracellular vesicle, and wherein at one of the three or more projecting stem loops comprises one or more functional moieties capable of treating the disease in the subject.

15. The method of claim 14, wherein the disease is an infection.

16. The method of claim 14, wherein the disease is cancer.

17. A method of imaging a cell, the method comprising contacting the cell with a composition comprising an extracellular vesicle displaying an RNA nanoparticle on its surface, wherein the nanoparticle is assembled from one or more ribonucleic acid strands duplexed together to form a secondary structure with three or more projecting stem loops, wherein at one of the three or more projecting stem loops is conjugated to a cholesterol moiety wherein at least one of the three or more projecting stem loops physically blocks encapsulation of the nanoparticle into the extracellular vesicle, and wherein at one of the three or more projecting stem loops comprises one or more diagnostic moieties.

18. The method of claim 17, wherein the cell is in a subject.

* * * * *

UNITED STATES PATENT AND TRADEMARK OFFICE
CERTIFICATE OF CORRECTION

PATENT NO. : 10,590,417 B2
APPLICATION NO. : 16/152911
DATED : March 17, 2020
INVENTOR(S) : Guo et al.

Page 1 of 1

It is certified that error appears in the above-identified patent and that said Letters Patent is hereby corrected as shown below:

In the Specification

Please replace the paragraph in Column 1, Lines 20-25 with the following:
This invention was made with government support under grant numbers EB019036, EB012135, CA151648, EB003730, and TR000875 awarded by the National Institutes of Health. The government has certain rights in the invention.

Signed and Sealed this
Sixth Day of October, 2020

Andrei Iancu
*Director of the United States Patent and Trademark Office*

SEQUENCE LISTING

<160> NUMBER OF SEQ ID NOS: 10

<210> SEQ ID NO 1
<211> LENGTH: 18
<212> TYPE: RNA
<213> ORGANISM: Artificial Sequence
<220> FEATURE:
<223> OTHER INFORMATION: Synthetic Construct

<400> SEQUENCE: 1
uugccaugug uauguggg                                                        18

<210> SEQ ID NO 2
<211> LENGTH: 21
<212> TYPE: RNA
<213> ORGANISM: Artificial Sequence
<220> FEATURE:
<223> OTHER INFORMATION: Synthetic Construct

<400> SEQUENCE: 2
cccacauacu uuguugaucc c                                                    21

<210> SEQ ID NO 3
<211> LENGTH: 16
<212> TYPE: RNA
<213> ORGANISM: Artificial Sequence
<220> FEATURE:
<223> OTHER INFORMATION: Synthetic Construct

<400> SEQUENCE: 3
ggaucaauca uggcaa                                                          16

<210> SEQ ID NO 4
<211> LENGTH: 41
<212> TYPE: RNA
<213> ORGANISM: Artificial Sequence
<220> FEATURE:
<223> OTHER INFORMATION: Synthetic Construct

<400> SEQUENCE: 4
uugccaugug uaugugggaa ucccgcggcc auggccggga g                              41

<210> SEQ ID NO 5
<211> LENGTH: 39
<212> TYPE: RNA
<213> ORGANISM: Artificial Sequence
<220> FEATURE:
<223> OTHER INFORMATION: Synthetic Construct

<400> SEQUENCE: 5
uugccaugug uauguggggc agguuccuua ucugucauu                                 39

<210> SEQ ID NO 6
<211> LENGTH: 41
<212> TYPE: RNA
<213> ORGANISM: Artificial Sequence
<220> FEATURE:
<223> OTHER INFORMATION: Synthetic Construct

<400> SEQUENCE: 6
uugccaugug uaugugggaa ucccgcggcc auggccggga g                              41

```
<210> SEQ ID NO 7
<211> LENGTH: 60
<212> TYPE: RNA
<213> ORGANISM: Artificial Sequence
<220> FEATURE:
<223> OTHER INFORMATION: Synthetic Construct

<400> SEQUENCE: 7
ggaucaauca uggcaauggg accgaaaaag accugacuuc uauacuaagu cuacguuccc      60

<210> SEQ ID NO 8
<211> LENGTH: 19
<212> TYPE: RNA
<213> ORGANISM: Artificial Sequence
<220> FEATURE:
<223> OTHER INFORMATION: Synthetic Construct

<400> SEQUENCE: 8
ugacagauaa ggaaccugc                                                  19

<210> SEQ ID NO 9
<211> LENGTH: 23
<212> TYPE: RNA
<213> ORGANISM: Artificial Sequence
<220> FEATURE:
<223> OTHER INFORMATION: Synthetic Construct

<400> SEQUENCE: 9
cucccggcca uggccgcggg auu                                             23

<210> SEQ ID NO 10
<211> LENGTH: 60
<212> TYPE: RNA
<213> ORGANISM: Artificial Sequence
<220> FEATURE:
<223> OTHER INFORMATION: Synthetic Construct

<400> SEQUENCE: 10
cccacauacu uuguugaucc cgccuuagua acgugcuuug augucgauuc gacaggaggc     60
```